(12) United States Patent
Boyden et al.

(10) Patent No.: US 8,280,484 B2
(45) Date of Patent: Oct. 2, 2012

(54) SYSTEM, DEVICES, AND METHODS FOR DETECTING OCCLUSIONS IN A BIOLOGICAL SUBJECT

(75) Inventors: Edward S. Boyden, Cambridge, MA (US); Eric C. Leuthardt, St. Louis, MO (US)

(73) Assignee: The Invention Science Fund I, LLC

( * ) Notice: Subject to any disclaimer, the term of this patent is extended or adjusted under 35 U.S.C. 154(b) by 377 days.

(21) Appl. No.: 12/387,459

(22) Filed: Apr. 30, 2009

(65) Prior Publication Data

US 2009/0318802 A1     Dec. 24, 2009

Related U.S. Application Data

(63) Continuation-in-part of application No. 12/004,107, filed on Dec. 18, 2007, and a continuation-in-part of application No. 12/004,453, filed on Dec. 19, 2007, and a continuation-in-part of application No. 12/005,122, filed on Dec. 20, 2007, and a continuation-in-part of application No. 12/005,154, filed on Dec. 21, 2007, and a continuation-in-part of application No. 12/152,265, filed on May 13, 2008, and a continuation-in-part of application No. 12/152,294, filed on May 13, 2008, and a continuation-in-part of application No. 12/152,639, filed on May 14, 2008, and a continuation-in-part of application No. 12/152,669, filed on May 14, 2008, and a continuation-in-part of application No. 12/152,846, filed on May 15, 2008, and a continuation-in-part of application No. 12/152,864, filed on May 15, 2008, and a continuation-in-part of application No. 12/152,868, filed on May 15, 2008, and a continuation-in-part of application No. 12/152,905, filed on May 15, 2008, and a continuation-in-part of application No. 12/154,138, filed on May 19, 2008, and a continuation-in-part of application No. 12/154,140, filed on May 19, 2008, (Continued)

(51) Int. Cl.
    *A61B 5/05* (2006.01)
(52) U.S. Cl. ........ 600/407; 600/473; 600/476; 600/310; 356/432; 356/433; 607/88; 607/89
(58) Field of Classification Search .................. 600/407, 600/409–410, 437, 473, 476, 480–485; 382/128, 382/224–225
    See application file for complete search history.

(56) References Cited

U.S. PATENT DOCUMENTS 3,409,008 A    11/1966   Mortensen et al.
(Continued)

FOREIGN PATENT DOCUMENTS

JP           7059754 A        3/1995
(Continued)

OTHER PUBLICATIONS

Merli, Geno, "Diagnostic assessment of deep vein thrombosis and pulmonary embolism", The American Journal of Medicine, 2005, pp. 3S-12S, vol. 118 (8A), Elsevier.

(Continued)

*Primary Examiner* — Tse Chen
*Assistant Examiner* — Joel F Brutus

(57) ABSTRACT

Systems, devices, and methods are described for detecting an embolus, thrombus, or a deep vein thrombus in a biological subject.

32 Claims, 24 Drawing Sheets

Related U.S. Application Data and a continuation-in-part of application No. 12/154,162, filed on May 19, 2008, and a continuation-in-part of application No. 12/154,277, filed on May 20, 2008, and a continuation-in-part of application No. 12/154,420, filed on May 21, 2008, and a continuation-in-part of application No. 12/154,422, filed on May 21, 2008, and a continuation-in-part of application No. 12/154,652, filed on May 22, 2008, and a continuation-in-part of application No. 12/154,654, filed on May 22, 2008, and a continuation-in-part of application No. 12/228,141, filed on Aug. 7, 2008, and a continuation-in-part of application No. 12/228,151, filed on Aug. 7, 2008, and a continuation-in-part of application No. 12/228,155, filed on Aug. 7, 2008, and a continuation-in-part of application No. 12/228,156, filed on Aug. 7, 2008.

(56) References Cited

U.S. PATENT DOCUMENTS

| | | | |
|---|---|---|---|
| 4,138,156 | A | 2/1979 | Bonner |
| 4,303,984 | A | 12/1981 | Houvig |
| 4,379,461 | A | 4/1983 | Nilsson et al. |
| 4,569,355 | A | 2/1986 | Bitterly |
| 4,629,336 | A | 12/1986 | Ishizaka |
| 4,689,041 | A | 8/1987 | Corday et al. |
| 4,804,054 | A | 2/1989 | Howson et al. |
| 4,820,261 | A | 4/1989 | Schmoll et al. |
| 4,981,596 | A | 1/1991 | Shiino et al. |
| 5,012,411 | A | 4/1991 | Policastro et al. |
| 5,153,827 | A | 10/1992 | Coutré et al. |
| 5,201,318 | A | 4/1993 | Rava et al. |
| 5,242,382 | A | 9/1993 | Gorsuch et al. |
| 5,243,998 | A | 9/1993 | Silverman et al. |
| 5,282,467 | A | 2/1994 | Piantadosi et al. |
| 5,305,745 | A | 4/1994 | Zacouto |
| 5,348,002 | A | 9/1994 | Caro |
| 5,348,015 | A * | 9/1994 | Moehring et al. ............ 600/453 |
| 5,429,137 | A | 7/1995 | Phelps et al. |
| 5,438,983 | A | 8/1995 | Falcone |
| 5,441,051 | A * | 8/1995 | Hileman et al. ............ 600/454 |
| 5,445,616 | A | 8/1995 | Kratoska et al. |
| 5,474,574 | A | 12/1995 | Payne et al. |
| 5,508,203 | A | 4/1996 | Fuller et al. |
| 5,524,636 | A | 6/1996 | Sarvazyan et al. |
| 5,546,955 | A | 8/1996 | Wilk |
| 5,620,475 | A | 4/1997 | Magnusson |
| 5,699,934 | A | 12/1997 | Kolcun et al. |
| 5,725,492 | A | 3/1998 | Igo et al. |
| 5,795,327 | A | 8/1998 | Wilson et al. |
| 5,807,261 | A * | 9/1998 | Benaron et al. ............ 600/473 |
| 5,832,182 | A | 11/1998 | Zhang et al. |
| 5,857,998 | A | 1/1999 | Barry |
| 5,916,817 | A | 6/1999 | Taheri |
| 5,925,016 | A | 7/1999 | Chornenky et al. |
| 5,991,654 | A | 11/1999 | Tumey et al. |
| 6,019,729 | A | 2/2000 | Itoigawa et al. |
| 6,064,770 | A | 5/2000 | Scarth et al. |
| 6,071,956 | A | 6/2000 | Slepian et al. |
| 6,124,597 | A | 9/2000 | Shehada et al. |
| 6,160,656 | A | 12/2000 | Mossberg et al. |
| 6,179,786 | B1 | 1/2001 | Young |
| 6,216,066 | B1 | 4/2001 | Goebel et al. |
| 6,238,354 | B1 | 5/2001 | Alvarez |
| 6,269,376 | B1 | 7/2001 | Dhillon et al. |
| 6,270,463 | B1 | 8/2001 | Morris, Sr. et al. |
| 6,280,390 | B1 | 8/2001 | Akselrod et al. |
| 6,282,448 | B1 | 8/2001 | Katz et al. |
| 6,358,201 | B1 | 3/2002 | Childre et al. |
| 6,384,627 | B1 | 5/2002 | Fross et al. |
| 6,385,332 | B1 | 5/2002 | Zahalka et al. |
| 6,387,059 | B1 | 5/2002 | Marchitto et al. |
| 6,409,662 | B1 | 6/2002 | Lloyd et al. |
| 6,447,460 | B1 | 9/2002 | Zheng et al. |
| 6,459,929 | B1 | 10/2002 | Hopper et al. |
| 6,478,757 | B1 | 11/2002 | Barak |
| 6,487,507 | B1 | 11/2002 | Mansfield et al. |
| 6,509,747 | B2 | 1/2003 | Nagai et al. |
| 6,529,751 | B1 | 3/2003 | Van Driel et al. |
| 6,547,736 | B1 | 4/2003 | Moehring et al. |
| 6,561,996 | B1 | 5/2003 | Gorsuch |
| 6,567,705 | B1 | 5/2003 | Stokes et al. |
| 6,580,016 | B2 | 6/2003 | Teirstein et al. |
| 6,585,763 | B1 | 7/2003 | Keilman et al. |
| 6,591,182 | B1 | 7/2003 | Cece et al. |
| 6,594,518 | B1 | 7/2003 | Benaron et al. |
| 6,600,947 | B2 | 7/2003 | Averback et al. |
| 6,610,024 | B1 | 8/2003 | Benatti |
| 6,629,937 | B2 | 10/2003 | Watrous |
| 6,635,027 | B1 | 10/2003 | Cragg et al. |
| 6,682,483 | B1 | 1/2004 | Abend et al. |
| 6,689,612 | B2 | 2/2004 | Samsoondar |
| 6,709,444 | B1 | 3/2004 | Makower |
| 6,763,261 | B2 | 7/2004 | Casscells, III et al. |
| 6,852,132 | B1 | 2/2005 | Houser et al. |
| 6,916,424 | B2 | 7/2005 | Collins et al. |
| 6,925,621 | B2 | 8/2005 | Mielke et al. |
| 6,957,094 | B2 | 10/2005 | Chance et al. |
| 6,969,345 | B2 | 11/2005 | Jassawalla et al. |
| 6,980,852 | B2 | 12/2005 | Jersey-Willuhn et al. |
| 6,985,294 | B1 | 1/2006 | Rosenthal et al. |
| 7,139,603 | B2 | 11/2006 | Chance |
| 7,167,734 | B2 | 1/2007 | Khalil et al. |
| 7,190,522 | B2 | 3/2007 | Moon et al. |
| 7,192,783 | B2 | 3/2007 | Alfano et al. |
| 7,196,620 | B2 | 3/2007 | Nanba |
| 7,233,739 | B2 | 6/2007 | Patel et al. |
| 7,236,821 | B2 | 6/2007 | Cates et al. |
| 7,291,497 | B2 | 11/2007 | Holmes et al. |
| 7,365,859 | B2 | 4/2008 | Yun et al. |
| 7,389,142 | B2 | 6/2008 | Holmström |
| 7,412,429 | B1 | 8/2008 | Syeda-Mahmood et al. |
| 7,430,455 | B2 | 9/2008 | Casey et al. |
| 7,461,073 | B2 | 12/2008 | Gao et al. |
| 7,489,825 | B2 | 2/2009 | Sirohey et al. |
| 7,531,133 | B2 | 5/2009 | Hole et al. |
| 7,603,166 | B2 | 10/2009 | Casscells, III et al. |
| 7,623,908 | B2 | 11/2009 | Boppart et al. |
| 7,664,548 | B2 | 2/2010 | Amurthur et al. |
| 7,666,151 | B2 | 2/2010 | Sullivan et al. |
| 7,729,747 | B2 | 6/2010 | Stranc et al. |
| 7,740,612 | B2 | 6/2010 | Hochman |
| 7,780,623 | B2 | 8/2010 | Soltanpour |
| 7,785,258 | B2 | 8/2010 | Braig et al. |
| 7,789,830 | B2 | 9/2010 | Ishida et al. |
| 7,828,739 | B2 | 11/2010 | Arnold |
| 7,833,239 | B2 | 11/2010 | Nash |
| 7,894,874 | B2 | 2/2011 | Lynch et al. |
| 7,931,600 | B2 | 4/2011 | Hatlestad et al. |
| 8,005,686 | B2 | 8/2011 | Smith |
| 2001/0031920 | A1 * | 10/2001 | Kaufman et al. ............ 600/431 |
| 2001/0044588 | A1 | 11/2001 | Mault |
| 2001/0047137 | A1 | 11/2001 | Moreno et al. |
| 2002/0099286 | A1 | 7/2002 | Sandler et al. |
| 2002/0107504 | A1 | 8/2002 | Gordon |
| 2002/0128545 | A1 | 9/2002 | Steuer et al. |
| 2003/0065536 | A1 | 4/2003 | Hansen et al. |
| 2003/0069481 | A1 | 4/2003 | Hervy et al. |
| 2003/0139778 | A1 | 7/2003 | Fischell et al. |
| 2003/0149997 | A1 | 8/2003 | Hageman |
| 2003/0195401 | A1 | 10/2003 | Tian et al. |
| 2003/0208116 | A1 * | 11/2003 | Liang et al. ............ 600/407 |
| 2004/0019278 | A1 | 1/2004 | Abend |
| 2004/0034284 | A1 | 2/2004 | Aversano et al. |
| 2004/0039268 | A1 | 2/2004 | Barbour et al. |
| 2004/0091933 | A1 | 5/2004 | Stoughton et al. |
| 2004/0133081 | A1 | 7/2004 | Teller et al. |
| 2004/0138562 | A1 | 7/2004 | Makower et al. |
| 2004/0143401 | A1 * | 7/2004 | Elling ............ 702/19 |
| 2004/0147837 | A1 | 7/2004 | Macaulay et al. |
| 2004/0176668 | A1 | 9/2004 | Goldstein |
| 2004/0186383 | A1 | 9/2004 | Rava et al. |
| 2004/0236225 | A1 | 11/2004 | Murphy et al. |

| | | |
|---|---|---|
| 2004/0249293 A1 | 12/2004 | Sandler et al. |
| 2004/0260346 A1 | 12/2004 | Overall et al. |
| 2005/0004461 A1 | 1/2005 | Abend |
| 2005/0027184 A1 | 2/2005 | Saldivar et al. |
| 2005/0033154 A1 | 2/2005 | deCharms |
| 2005/0034485 A1 | 2/2005 | Klefstad-Sillonville et al. |
| 2005/0085769 A1 | 4/2005 | MacMahon et al. |
| 2005/0096528 A1 | 5/2005 | Fritz et al. |
| 2005/0124969 A1 | 6/2005 | Fitzgerald et al. |
| 2005/0148899 A1 | 7/2005 | Walker et al. |
| 2005/0171434 A1 | 8/2005 | Madden et al. |
| 2005/0175665 A1 | 8/2005 | Hunter et al. |
| 2005/0186245 A1 | 8/2005 | Hunter et al. |
| 2006/0010012 A1 | 1/2006 | Franzblau et al. |
| 2006/0047301 A1 | 3/2006 | Ogle |
| 2006/0089556 A1 | 4/2006 | Bambot et al. |
| 2006/0100530 A1 | 5/2006 | Kliot et al. |
| 2006/0135940 A1 | 6/2006 | Joshi |
| 2006/0149313 A1 | 7/2006 | Arguello et al. |
| 2006/0184280 A1 | 8/2006 | Oddsson et al. |
| 2006/0241521 A1 | 10/2006 | Cohen |
| 2006/0253301 A1 | 11/2006 | Simms et al. |
| 2006/0290516 A1 | 12/2006 | Muehlsteff et al. |
| 2006/0293572 A1 | 12/2006 | Bulat |
| 2007/0021774 A1 | 1/2007 | Hogendijk |
| 2007/0043308 A1 | 2/2007 | Lee |
| 2007/0054266 A1 | 3/2007 | Sato et al. |
| 2007/0060811 A1 | 3/2007 | Roberts |
| 2007/0078500 A1 | 4/2007 | Ryan et al. |
| 2007/0083090 A1 | 4/2007 | Sterling et al. |
| 2007/0166707 A1 | 7/2007 | Schadt et al. |
| 2007/0167836 A1* | 7/2007 | Scepanovic et al. .......... 600/476 |
| 2007/0200085 A1 | 8/2007 | Matsui et al. |
| 2007/0213600 A1 | 9/2007 | John et al. |
| 2007/0213613 A1 | 9/2007 | Ishida et al. |
| 2007/0232940 A1 | 10/2007 | Fine et al. |
| 2007/0232958 A1 | 10/2007 | Donofrio et al. |
| 2007/0233019 A1 | 10/2007 | Forsell |
| 2007/0255199 A1 | 11/2007 | Dewey |
| 2008/0004550 A1 | 1/2008 | Einav et al. |
| 2008/0044072 A1* | 2/2008 | Kiraly et al. ................. 382/128 |
| 2008/0058758 A1 | 3/2008 | Ranchod et al. |
| 2008/0071185 A1 | 3/2008 | Beck et al. |
| 2008/0077019 A1 | 3/2008 | Xiao et al. |
| 2008/0132976 A1 | 6/2008 | Kane et al. |
| 2008/0146970 A1 | 6/2008 | Litman et al. |
| 2008/0161698 A1 | 7/2008 | Sum et al. |
| 2008/0208011 A1 | 8/2008 | Shuler |
| 2008/0221457 A1 | 9/2008 | Zeng et al. |
| 2008/0242952 A1 | 10/2008 | Jung et al. |
| 2008/0262344 A1 | 10/2008 | Brummett |
| 2008/0275393 A1 | 11/2008 | Bonnette et al. |
| 2008/0294019 A1 | 11/2008 | Tran |
| 2008/0300493 A1 | 12/2008 | Gatto et al. |
| 2008/0320098 A1 | 12/2008 | Jung et al. |
| 2009/0012382 A1 | 1/2009 | Dutta et al. |
| 2009/0048577 A1 | 2/2009 | Gillies et al. |
| 2009/0063518 A1 | 3/2009 | Jung et al. |
| 2009/0198129 A1 | 8/2009 | Varghese et al. |
| 2009/0227997 A1 | 9/2009 | Wang et al. |
| 2009/0234672 A1 | 9/2009 | Dicks et al. |
| 2009/0287093 A1 | 11/2009 | Ferren et al. |
| 2009/0287101 A1 | 11/2009 | Ferren et al. |
| 2009/0306484 A1 | 12/2009 | Kurtz et al. |
| 2009/0324608 A1 | 12/2009 | Meyers et al. |
| 2010/0016733 A1 | 1/2010 | Smith et al. |
| 2010/0063365 A1 | 3/2010 | Pisani et al. |
| 2010/0234714 A1 | 9/2010 | Mercier et al. |
| 2010/0268112 A1 | 10/2010 | Short et al. |
| 2011/0087113 A1 | 4/2011 | Mack et al. |
| 2011/0112416 A1 | 5/2011 | Myr |
| 2011/0160549 A1 | 6/2011 | Saroka et al. |
| 2011/0201955 A1 | 8/2011 | Hatlestad et al. |
| 2011/0257577 A1 | 10/2011 | Lane et al. |

FOREIGN PATENT DOCUMENTS

| | | | |
|---|---|---|---|
| WO | WO 94/14487 | | 7/1994 |
| WO | WO 2005/046482 | A1 | 5/2005 |
| WO | WO 2006/109072 | A2 | 10/2006 |
| WO | WO 2007/015094 | A2 | 2/2007 |
| WO | WO 2007/067952 | A2 | 6/2007 |
| WO | WO 2007/093804 | A2 | 8/2007 |
| WO | WO 2008/024080 | A1 | 2/2008 |
| WO | WO 2008/039212 | A2 | 4/2008 |

OTHER PUBLICATIONS

Apple et al.; "Future Biomarkers for Detection of Ischeima and Risk Stratification in Acute Coronary Syndrome"; Clinical Chemistry; bearing a date of 2005; pp. 810-824; vol. 51, No. 5; American Association for Clinical Chemistry.

Bain, B. J., Dr.; "Review: The Haematological Features of HIV Infection"; British Journal of Haematology; bearing a date of 1997; pp. 1-8; vol. 99; Blackwell Science Ltd.

Baranoski et al.; "An Introduction to Light Interaction with Human Skin"; RITA; bearing a date of 2004; pp. 33-62; vol. XI, No. 1.

Barnes et al.; "Novel Biomarkers Associated with Deep Venous Thrombosis: A Comprehensive Review"; Biomarker Insights; bearing a date of 2007; pp. 93-100; vol. 2; Creative Commons Attribution.

Becker et al.; "Advanced Time-Correlated Single Photon Counting Technique for Spectroscopy and Imaging in Biomedical Systems"; Proc. SPIE; bearing a date of 2004; pp. 1-9; vol. 5340.

Bitigen et al.; "Acute Anterior Myocardial Infarction Due to Aortosaphenous Vein Graft Occlusion with very Large Thrombus Burden"; Clinical Cardiology: Case Reports; bearing a date of 2007; pp. 203-205; vol. 12, No. 4; Pulsus Group Inc.

Black et al.; "Cooperative Phenomena in Two-Pulse, Two-Color Laser Photocoagulation of Cutaneous Blood Vessels"; bearing dates of 1995-2008; 12 pages.

"Blood Clot Prevention: Battling a Dangerous Condition"; Life Extension; bearing a date of Jan. 19, 2006; 11 pages; Life Extension Foundation; located at: http://www.lef.org/.

Callum et al.; "ABC of Arterial and Venous Disease: Acute Limb Ischaemia"; BMJ; bearing a date of Mar. 18, 2000; pp. 764-767; vol. 320; located at: www.bmj.com.

Chance et al.; "A Novel Method for Fast Imaging of Brain Function, Non-Invasively, with Light"; Optics Express; bearing a date of May 11, 1998; pp. 411-423; vol. 2, No. 10; OSA.

Dauksaite et al.; "Antibody-Based Protein Detection Using Piezoresistive Cantilever Arrays"; Nanotechnology; bearing a date of 2007; pp. 1-5; vol. 18; IOP Publishing Ltd.

De Grand et al.; "An Operational Near-Infrared Fluorescence Imaging System Prototype for Large Animal Surgery"; Technology in Cancer Research & Treatment; bearing a date of Dec. 2003; pp. 1-10; vol. 2, No. 6; Adenine Press.

Farokhzad et al.; "Review: Drug Delivery Systems in Urology-Getting "Smarter""; Elsevier: Urology; bearing a date of 2006; pp. 463-469; vol. 68; Elsevier Inc.

Fenart et al.; "Evaluation of Effect of Charge and Lipid Coating on Ability of 60-nm Nanoparticles to Cross an In Vitro Model of the Blood-Brain Barrier"; The Journal of Pharmacology and Experimental Therapeutics; bearing a date of 1999; pp. 1017-1022; vol. 291, No. 3; The American Society for Pharmacology and Experimental Therapeutics.

Ferreira et al.; "Muscle Capillary Blood Flow Kinetics Estimated from Pulmonary $O_2$ Uptake and Near-Infrared Spectroscopy"; Journal of Applied Physiology; bearing a date of 2005; pp. 1820-1828; vol. 98; The American Physiological Society; located at: http://www.jap.org.

Flaumenhaft et al.; "Localization and Quantification of Platelet-Rich Thrombi in Large Blood Vessels with Near-Infrared Fluorescence Imaging"; Circulation- Journal of the American Heart Association; bearing a date of 2007; pp. 84-93; vol. 115; American Heart Association; located at: http://www.circulation.org.

Gatto et al.; "Optical Microprobe for Blood Clot Detection"; 3 pages.

Giannitsis et al.; "Risk Stratification in Pulmonary Embolism Based on Biomarkers and Echocardiography"; Circulation- Journal of the American Heart Association; bearing a date of 2005; pp. 1520-1521; vol. 112; American Heart Association; located at: http://www.circulation.org.

Greco, Frank A.; "Reflectance Spectroscopy of Clotting Blood"; Arch Pathol Lab Med; bearing a date of Feb. 2004; pp. 173-180; vol. 128.

Heron et al.; "Deaths: Preliminary Data for 2006"; National Vital Statistics Reports; bearing a date of Jun. 11, 2008; pp. 1-52; vol. 56, No. 16.

Hoff, Janet.; "Methods of Blood Collection in the Mouse"; Lab Animal; bearing a date of Nov. 2000; pp. 47-53; vol. 29, No. 10.

Horecker, B.L.; "The Absorption Spectra of Hemoglobin and its Derivatives in the Visible and Near Infra-Red Regions"; The Journal of Biological Chemistry; bearing a date of Dec. 3, 1942; pp. 173-183; located at: www.jbc.org.

Huang et al.; "Assessment of Blood Coagulation Under Various Flow Conditions with Ultrasound Backscattering"; IEEE Transactions on Biomedical Engineering; bearing a date of Dec. 2007; pp. 2223-2230; vol. 54, No. 12; IEEE.

Huang et al.; "Detection of Blood Coagulation and Clot Formation Using Quantitative Ultrasonic Parameters"; Elsevier- Ultrasound in Med. & Biol.; bearing a date of 2005; pp. 1567-1573; vol. 31, No. 11; World Federation for Ultrasound in Medicine and Biology.

Huarng et al.; "A Multivariate Heuristic Model for Fuzzy Time-Series Forecasting"; IEEE Transactions on Systems, Man, and Cybernetics-Part B: Cybernetics; bearing a date of Aug. 2007; pp. 836-846; vol. 37, No. 4; IEEE.

InfraScan: "Near Infrared Technology" website, no article provided; located at: http://www.infrascanner.com/p_infrared.html.

Imam et al.; "Radiotracers for Imaging of Infection and Inflammation- A Review"; World Journal of Nuclear Medicine; bearing a date of Jan. 2006; pp. 40-55; vol. 5, No. 1.

"International HIV/AIDS Trial Finds"; National Institute of Allergy and Infectious Diseases (NIAID); bearing a date of Jan. 18, 2006; pp. 1-3; located at: http://www.niaid.nih.gov/.

Jacques, Steven L.; "Time-Resolved Reflectance Spectroscopy in Turbid Tissues"; IEEE Transactions on Biomedical Engineering; bearing a date of Dec. 1989; pp. 1155-1161; vol. 36, No. 12; IEEE.

Jaffer et al.; "In Vivo Imaging of Thrombin Activity in Experimental Thrombi with Thrombin-Sensitive Near-Infrared Molecular Probe"; American Heart Association: Arteriosclerosis, Thrombosis, and Vascular Biology, Journal of the American Heart Association; bearing a date of 2002; pp. 1929-1935; American Heart Association, Inc.; located at: atvb.ahajournals.org.

Jilani et al.; "Fuzzy Metric Approach for Fuzzy Time Series Forecasting Based on Frequency Density Based Partitioning"; Proceedings of World Academy of Science, Engineering and Technology; bearing a date of Aug. 2007; pp. 333-338; vol. 23; waset.org.

Jaiswal et al.; "Research Article- Long-Term Multiple Color Imaging of Live Cells Using Quantum Dot Bioconjugates"; Nature Biotechnology; bearing a date of Jan. 2003; pp. 47-51; vol. 21; Nature Publishing Group; located at: www.nature.com/naturebiotechnology.

Kalchenko et al.; "Use of Lipophilic Near-Infrared Dye in Whole-Body Optical Imaging of Hematopoietic Cell Homing"; JBO Letters, Journal of Biomedical Optics; bearing dates of Sep./Oct. 2006; pp. 050507-1 through 050507-3; vol. 11, No. 5; SPIE.

Kamphuisen et al.; "Can Anticoagulant Treatment be Tailored with Biomarkers in Patients with Venous Thromboembolism?"; Journal of Thrombosis and Haemostasis; bearing a date of 2006; pp. 1206-1207; vol. 4; International Society on Thrombosis and Haemostasis.

Keymeulen et al.; "On-Line Model-Based Learning Using Evolvable Hardware for a Robotics Tracking System"; Genetic Programming; Proceedings of the Third Annual Conference; bearing dates of Jul. 22-25, 1998; pp. 1-8.

Lewis et al.; "Metabolite Profiling of Blood from Individuals Undergoing Planned Myocardial Infarction Reveals Early Markers of Myocardial Injury"; The Journal of Clinical Investigation: Technical advance; pp. 1-10; located at: http://www.jci.org.

Li et al.; "Feasibility of Interstitial Doppler Optical Coherence Tomography for In Vivo Detection of Microvascular Changes During Photodynamic Therapy"; Lasers in Surgery and Medicine; bearing a date of 2006; pp. 754-761; vol. 38; Wiley-Liss, Inc.

Lim et al.; "Wavelength-Band Selection Filter Based on Surface Plasmon Resonance and Phase Conjugation Holography"; IEEE Photonics Technology Letters; bearing a date of Dec. 1, 2006; pp. 2532-2534; vol. 18, No. 23; IEEE.

Luxburg, Ulrike Von; "Technical Report No. TR-149: A Tutorial on Spectral Clustering"; Max Planck Institute for Biological Cybernetics; bearing a date of Aug. 2006; pp. 1-25 plus cover sheet.

"Making Tissue Temporarily Transparent for Better Diagnosis and Treatment" website, article not provided; located at: http://www.medscape.com/viewarticle/412068.

Mariampillai et al.; "Speckle Variance Detection of Microvasculature Using Swept-Source Optical Coherence Tomography"; Optics Letters; bearing a date of Jul. 1, 2008; pp. 1530-1532; vol. 33, No. 13; Optical Society of America.

Massoud et al.; "Review: Molecular Imaging in Living Subjects: Seeing Fundamental biological Processes in a New Light"; Genes and Development; bearing a date of 2003; pp. 545-580; vol. 17; Cold Spring Harbor Laboratory Press.

"Mining Whole-Sample Mass-Spectrometry Proteomics Data for Biomarkers-An Overview"; bearing a date of Oct. 12, 2007; 15 pages; Elsevier Science.

Myers et al.; "Basic Research Studies: P-Selectin and Leukocyte Microparticles are Associated with Venous Thrombogenesis"; From the American Venous Forum: Journal of Vascular Surgery; bearing a date of Nov. 2003; pp. 1075-1089; vol. 38, No. 5; The Society for Vascular Surgery.

Nadeau et al.; "High-Q Whispering-Gallery Mode Sensor in Liquids"; pp. 1-8; Oewaves, Inc.

"New Sensor Developed at UCSB can Detect DNA in One Step"; Science Daily website, article not provided; located at: http://www.sciencedaily.com/releases/2003/07/030718084533.htm.

Nissl, Jan; Information and Resources: Complete Blood Count (CBC); WebMD; bearing a date of Dec. 4, 2006; pp. 1-9; Healthwise, Incorporated; located at: http://www.webmd.com/a-to-z-guides/complete-blood-count-cbc; printed on Aug. 25, 2008.

Novo et al.; "Letters: Direct Observation of Chemical Reactions on Single Gold Nanocrystals Using Surface Plasmon Spectroscopy"; Nature Nanotechnology; bearing a date of Oct. 2008; pp. 598-602; vol. 3; Macmillan Publishers Limited; located at: www.nature.com/naturenanotechnology.

"Optical Absorption of Hemoglobin" website, no article provided; located at: http://omlc.ogi.edu/spectra/hemoglobin/index.html.

Parrish et al.; "Laser Photomedicine"; IEEE Journal of Quantum Electronics; bearing a date of Dec. 1984; pp. 1386-1396; vol. QE-20, No. 12; IEEE.

"Porous Carbon Sponges Prepared by Aerosol Technique"; News Bureau University of Illinois at Urbana-Champaign; bearing a date of Oct. 2, 2006; pp. 1-2; located at: http://news.illinois.edu/news/06/1002carbon.html; printed on Apr. 16, 2009.

Ramzi et al.; "DVT and Pulmonary Embolism: Part II. Treatment and Prevention"; Practical Therapeutics; bearing a date of Jun. 15, 2004; pp. 2841-2848; vol. 69, No. 12; American Family Physician; located at: www.aafp.org/afp.

Reynolds et al.; "Oak Ridge Conference- Early Biomarkers of Stroke"; Clinical Chemistry; bearing a date of 2003; pp. 1733-1739; vol. 49, No. 10.

Rhinelander et al.; "A Single-Class Support Vector Machine Translation Algorithm to Compensate for Non-Stationary Data in Heterogeneous Vision-Based Sensor Networks"; IEEE International Instrumentation and Measurement Technology Conference; bearing dates of May 12-15, 2008; 5 pages; IEEE.

Rosalki et al.; "History- Cardiac Biomarkers for Detection of Myocardial Infarction: Perspectives from Past to Present"; American Association of Clinical Chemistry; bearing a date of 2004; pp. 2205-2213, vol. 50, No. 11.

Savchenkov et al.; "Tunable Optical Frequency Comb with a Crystalline Whispering Gallery Mode Resonator"; Physical Review Letters; bearing a date of Aug. 29, 2008; pp. 093902-1 to 093902-4; vol. 101; The American Physical Society.

Schaffer et al.; "Real-Time Two-Photon Fluorescence Microscopy of Blood Flow Dynamics Following Photothrombotic Stroke in Rat Neocortex"; 2 pages.

Schmidt et al.; "Resolving pm Wavelength Shifts in Optical Sensing"; Applied Physics B, Lasers and Optics; bearing a date of 2007; 1 page; vol. 86; printed on Apr. 13, 2009.

"SPY: A Spectrophotometric Study of Hemoglobin" website, no article provided; located at: http://www.biochem.wisc.edu/courses/biochem651/labs/spy.aspx.

Steenbergen et al.; "Light-Scattering Properties of Undiluted Human Blood Subjected to Simple Shear"; J. Opt. Soc. Am. A; bearing a date of Dec. 1999; pp. 2959-2967; vol. 16, No. 12; Optical Society of America.

Stenstrom et al.; "Ultra-Violet Absorption Spectra of Blood Serum and Certain Amino Acids"; The Journal of Biological Chemistry; bearing dates of Sep. 26, 1925 and Feb. 6, 2009; pp. 819-827; located at: www.jbc.org.

Suman et al.; "Abstract: Cavitand-Based Supramolecular Sensors for the Detection of Acetates"; Science Direct; only Abstract provided; bearing a date of 2003; Elsevier Ltd.; located at: http://www.sciencedirect.com/science?_ob=ArticleURL&_udi=B6W8P-48170YV-5&_user=10&_rdoc=1&_fmt=&_orig=search&_sort=d&view=c&_acct=C000050221&_version=1&_urlVersion=0&_userid=10&md5=76b6b766f900e51061f8a3c7789f42d3.

Tabor et al.; "Patient-Specific Arterial Flow Simulation with Additional Geometric Elements"; European Conference on Computational Fluid Dynamics; bearing a date of 2006; pp. 1-12; TU Delft.

Tamura et al.; "Extended Summary: Application to Noninvasive Measurement of Blood Components Based on Infrared Spectroscopy"; p. 2.

"Tech Tip #6: Extinction Coefficients"; Thermo Scientific; pp. 1-3; Pierce Biotechnology.

The Hong Kong Association of Blood Transfusion and Haemotology website, no article provided; located at: http://www.fmshk.com.hk/hkabth/home.htm.

Veiseh et al.; "Research Article: Tumor Paint: A Cholorotoxin:Cy5.5 Bioconjugate for Intraoperative Visualization of Cancer Foci"; Cancer Research; bearing a date of Jul. 15, 2007; pp. 6882-6888; vol. 67, No. 14; American Association for Cancer Research; located at: www.aacrjournals.org.

Vellekoop et al.; "Universal Optimal Transmission of Light Through Disordered Materials"; bearing a date of Aug. 13, 2008; pp. 1-4.

Wang et al.; "Detection of the Process of Blood coagulation and Clot Formation Using Quantitative Ultrasonic Parameters"; IEEE Ultrasonics Symposium; bearing a date of 2002; pp. 1653-1656; IEEE.

"Whispering Gallery Mode (WGM) Based Micro-Optical Sensor Technology" website, no article provided; located at: http://engr.smu.edu/me/microsensor/Projects/WGM%20General.htm.

Wieringa et al.; "Remote Non-Invasive Stereoscopic Imaging of Blood Vessels: First In-Vivo Results of a New Multispectral Contrast Enhancement Technology"; Annals of Biomedical Engineering; bearing a date of Dec. 2006; pp. 1870-1878; vol. 34, No. 12; Biomedical Engineering Society.

Zwaginga et al.; "Thrombus Formation and Platelet-Vessel Wall Interaction in the Nephrotic Syndrome Under Flow Conditions"; J. Clin. Invest.; bearing a date of Jan. 1994; pp. 204-211; vol. 93; The American Society for Clinical Investigation, Inc.

Agen Biomedical (division of Agenix) (http://www.agenix.com/agenix/); visited May 17, 2010.

American College of Chest Physicians (http://www.chestnet.org/accp/); visited May 17, 2010.

American Thrombosis Association (http://www.bloodclot.org); visited May 17, 2010.

Center for Disease Control and Prevention (CDC) (http://www.cdc.gov/features/thrombosis/); visited May 17, 2010.

Clinical Trial to Evaluate the Accuracy of [99mTc] ThromboView in the Detection of Deep Vein Thrombosis (http://www.clinicaltrials.gov/ct2/show/NCT00123734?tem=dvt&rank=5); visited May 17, 2010.

Curriculum vitae of Molly Rossow; (http://www.lfd.uci.edu/~rossow/); visited May 17, 2010.

"Deep-Vein Thrombosis: Advancing Awareness to Protect Patient Lives"; White Paper, Public Health Leadership Conference on Deep-Vein Thrombosis; bearing a date of Feb. 26, 2003; cover page and pp. 1-12; American Public Health Association.

"Deep Venous Thrombosis (DVT)"; merck.com; printed on Jun. 15, 2010; pp. 1-10; located at http://www.merck.com/mmpe/print/sec07/ch081/ch081b.html.

Deep Vein Thrombosis Symptoms.com (http://www.deep-vein-thrombosis-symptoms.com/); visited May 17, 2010.

"Diagnostic Workup of Patients Presenting With Signs and Symptoms of DVT"; UWMC VTE Tool Kit; bearing a date of Sep. 23, 2009; 1 page; University of Washington Medical Center (UWMC).

Elixa Light Therapy Overview (http://www.elixa.com/light/healing.htm); visited May 17, 2010.

Gibbs, Harry; "Diagnostic tests: The diagnosis of recurrent deep venous thrombosis"; Australian Prescriber; bearing a date of Apr. 2007; pp. 38-40; vol. 30, No. 2.

"Guidelines for Prevention of Venous Thromboembolism"; UW Medicine VTE Tool Kit; bearing a date of May 17, 2010; pp. 1-3; UW Medicine.

International Society of Thrombosis & Haemostasis (http://www.isth.org/Default.aspx); visited May 17, 2010.

Journal of Thrombosis and Haemostasis (http://www.isth.org/Publications/JTH/tabid/88/Default.aspx); visited May 17, 2010.

Karpiouk, A.B. et al.; "Combined Ultrasonic and Photoacoustic Imaging to Age Deep Vein Thrombosis: Preliminary Studies"; 2005 IEEE Ultrasonics Symposium; bearing a date of 2005; pp. 399-402; IEEE.

Karpiouk, Andrei B. et al.; "Combined ultrasound and photoacoustic imaging to detect and stage deep vein thrombosis: phantom and ex vivo studies"; Journal of Biomedical Optics; bearing a date of Sep./Oct. 2008; pp. 054061-1-054061-8; vol. 13, Issue 5; SPIE.

Kierkegaard, A.; "Size of the thrombus in acute deep vein thrombosis and the significance of patients' age and sex"; Acta Chir Scand; bearing a date of 1981; pp. 259-261 (abstract only—1 pg.); vol. 147, No. 4; U.S. National Library of Medicine, National Institutes of Health.

Kim, Young-Hoo et al.; "Incidence and natural history of deep-vein thrombosis after total hip arthroplasty"; The Journal of Bone & Joint Surgery (Br); bearing a date of Jul. 2003; pp. 661-665; vol. 85-B, No. 5; British Editorial Society of Bone and Joint Surgery.

LED Therapy Center (http://www.ledtherapycenter.com/conditions-heiped-by-led/); visited May 17, 2010.

MedLightPro.com (http://www.calldoctorpaul.com/MLPtechnology.html); visited May 17, 2010.

Merck Manual Regarding Deep Venous Thrombosis (DVT) (http://www.merck.com/mmpe/sec07/ch081/ch081b.html); visited May 17, 2010.

National Alliance for Thrombosis and Thrombophilia (http://www.stoptheclot.org/); visited May 17, 2010.

OSA (http://www.osa.org/); visited May 17, 2010.

Rolfe, Peter; "In Vivo Near-Infrared Spectroscopy"; Annual Review of Biomedical Engineering; bearing a date of Aug. 2000; pp. 715-754 (abstract only—2 pg.); vol. 2; Annual Reviews.

Seyahi, Nurhan et al.; "Ultrasound imaging findings of femoral veins in patients with renal failure and its impact on vascular access"; Nephrology Dialysis Transplantation; bearing a date of 2005; pp. 1864-1867; vol. 20; Oxford University Press.

U of WA VTE Venous Thromboembolism (http://vte.son.washington.edu/) visited May 17, 2010.

Dieter, Robert S. et al.; "Prosthetic Heart Valve Thrombosis: An Overview"; Wisconsin Medical Journal; Bearing a date of 2002; pp. 67-68; vol. 101, No. 7.

Landry, Anthony et al.; "Theoretical and experimental quantification of carotid plaque volume measurements made by three-dimensional ultrasound using test phantoms"; Medical Physics; bearing a date of Oct. 2002; pp. 2319-2327; vol. 29, No. 10; American Association Physical Medicine.

Mackinnon, Andrew D. et al.; "Long-Term Ambulatory Monitoring for Cerebral Emboli Using Transcranial Doppler Ultrasound"; STROKE; Journal of the American Heart Association; originally published Dec. 18, 2003; pp. 73-78; American Heart Association.

Abita, Joseph L. et al.; "Transdermal Optical Communications"; Johns Hopkins APL Technical Digest; bearing a date of 2004; pp. 261-268; vol. 25, No. 3.

Blair, H. A.; "On the Excitation of Tissue by Means of Condenser Discharges"; The Journal of General Physiology; bearing a date of Aug. 29, 1932; pp. 177-189.

Izzetoglu, Meltem et al.; "Single Trial Hemodynamic Response Estimation in Event Related fNIR Spectroscopy"; bearing a date of 2003; 3 pages total; Optical Society of America.

Kraitl, Jens et al.; "Optical non-invasive methods for characterization of the human health status"; 1st International Conference on Sensing Technology; bearing dates of Nov. 21-23, 2005; pp. 466-470; Palmerston North; New Zealand.

Nath, Pulak et al.; "A System for Micro/Nano Fluidic Flow Diagnostics"; BioMedical Microdevices; bearing a date of 2005; pp. 169-177; Springer Science + Business Media, Inc.; The Netherlands.

Weil, M. H.; "Defining Hemodynamic Instability"; Update in Intensive Care and Emergency Medicine; 2005; pp. 9-17, (2 page abstract printed on Aug. 16, 2011); vol. 42, part 2; (abstract located at : http://www.springerlink.com/content/1h3g72p32621125j/).

Baumgartner et al.; "Factors Controlling Thrombus Formation on Arterial Lesions"; Annals New York Academy of Sciences; Oct. 1985; pp. 162-177; vol. 454; Issue 1.

Smith et al.; "A Comparison of Four Methods for Distinguishing Doppler Signals From Gaseous and Particulate Emboli"; Journal of the American Heart Association; Jun. 1998; pp. 1133-1138; vol. 29; No. 6; American Heart Association; Dallas, TX.

Carter, J. Stein; "Circulatory System"; bearing a date of Nov. 13, 2006; pp. 1-5; http://biology.clc.uc.edu/courses/bio105/circulat.htm.

Thefreedictionary.com; "Tonometer"; bearing a date of 2012, printed on Jun. 13, 2012; pp. 1-4; Farlex, Inc.; http://medical-dictionary.thefreedictionary.com/tonometer.

* cited by examiner

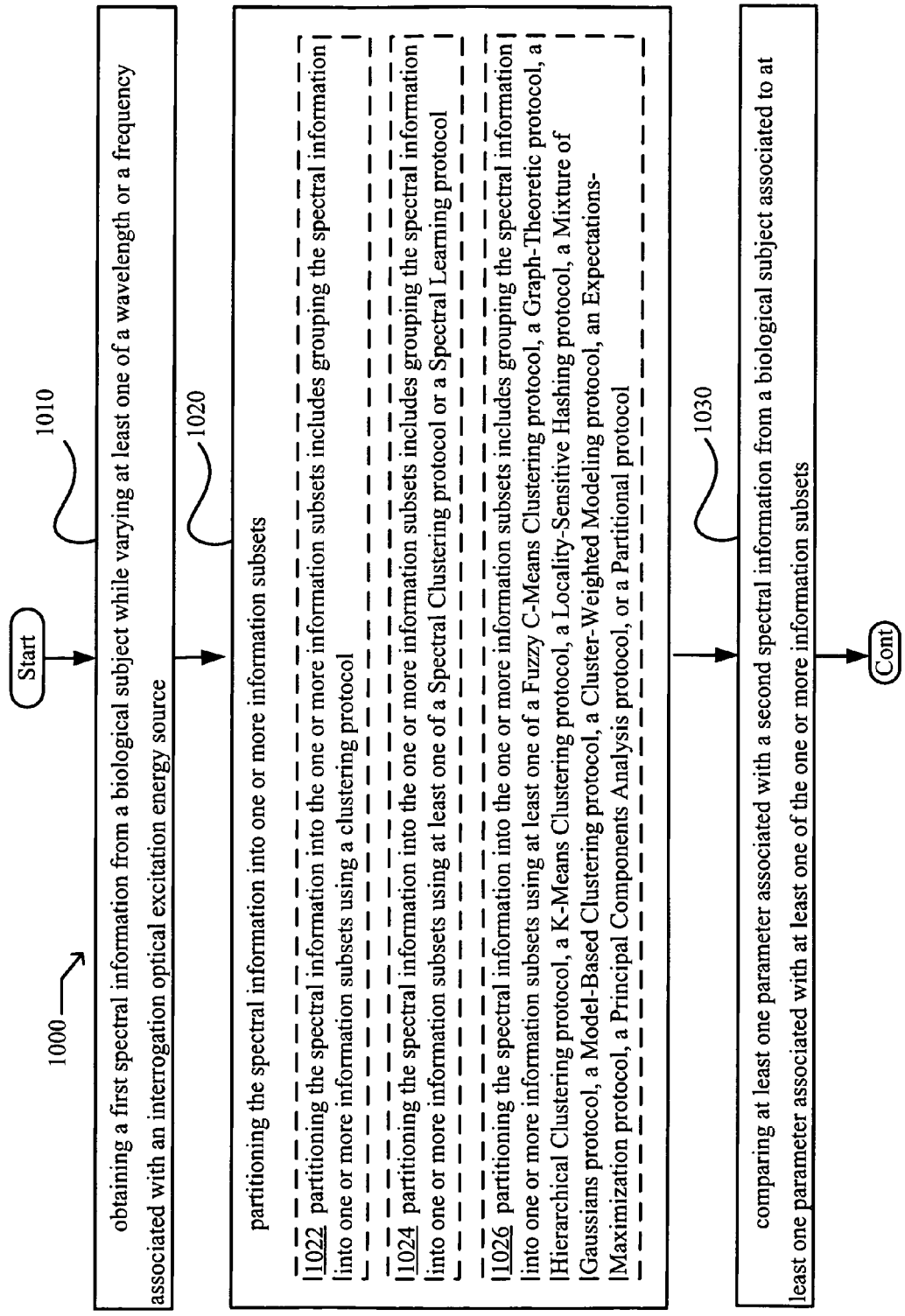

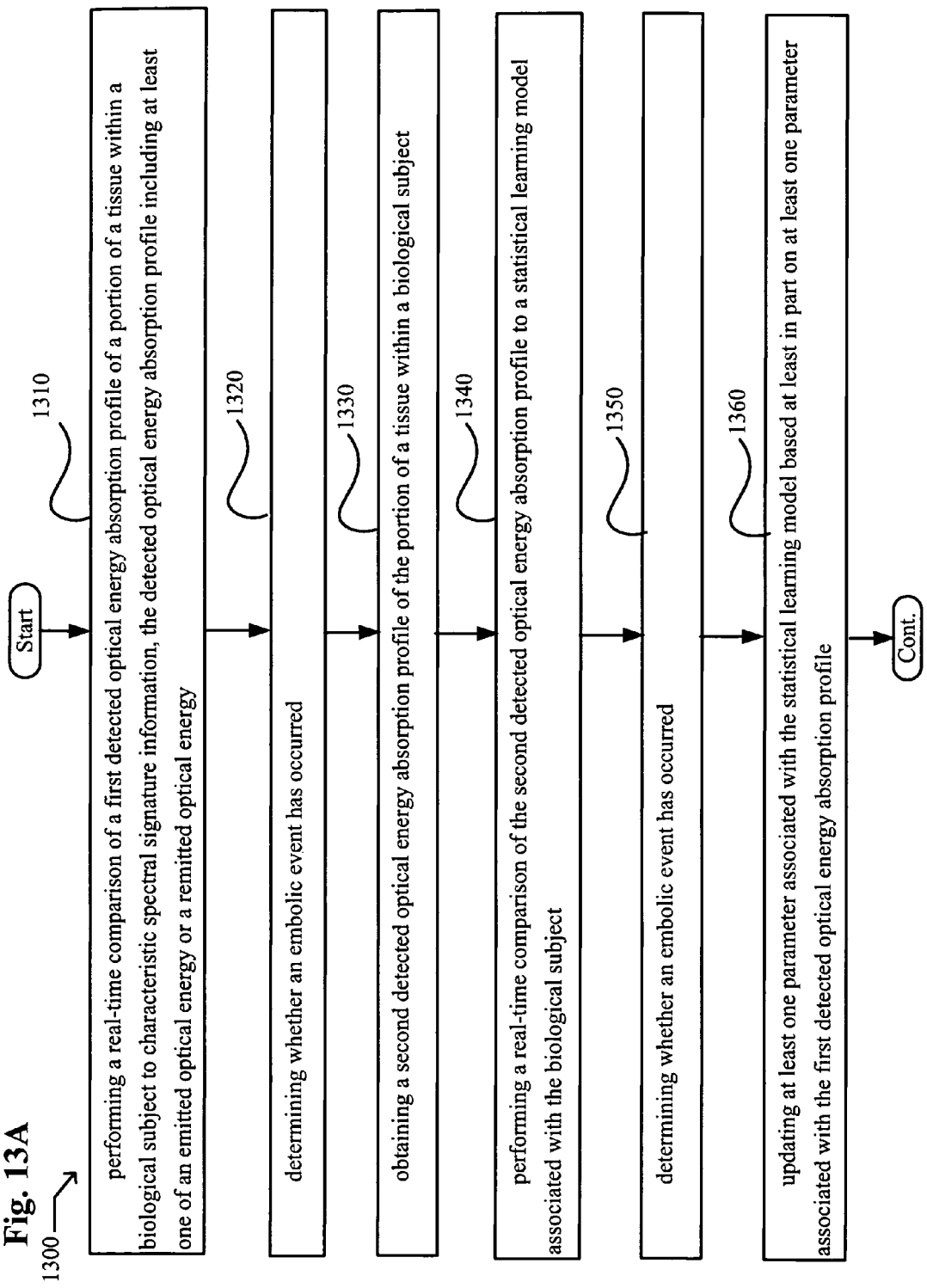

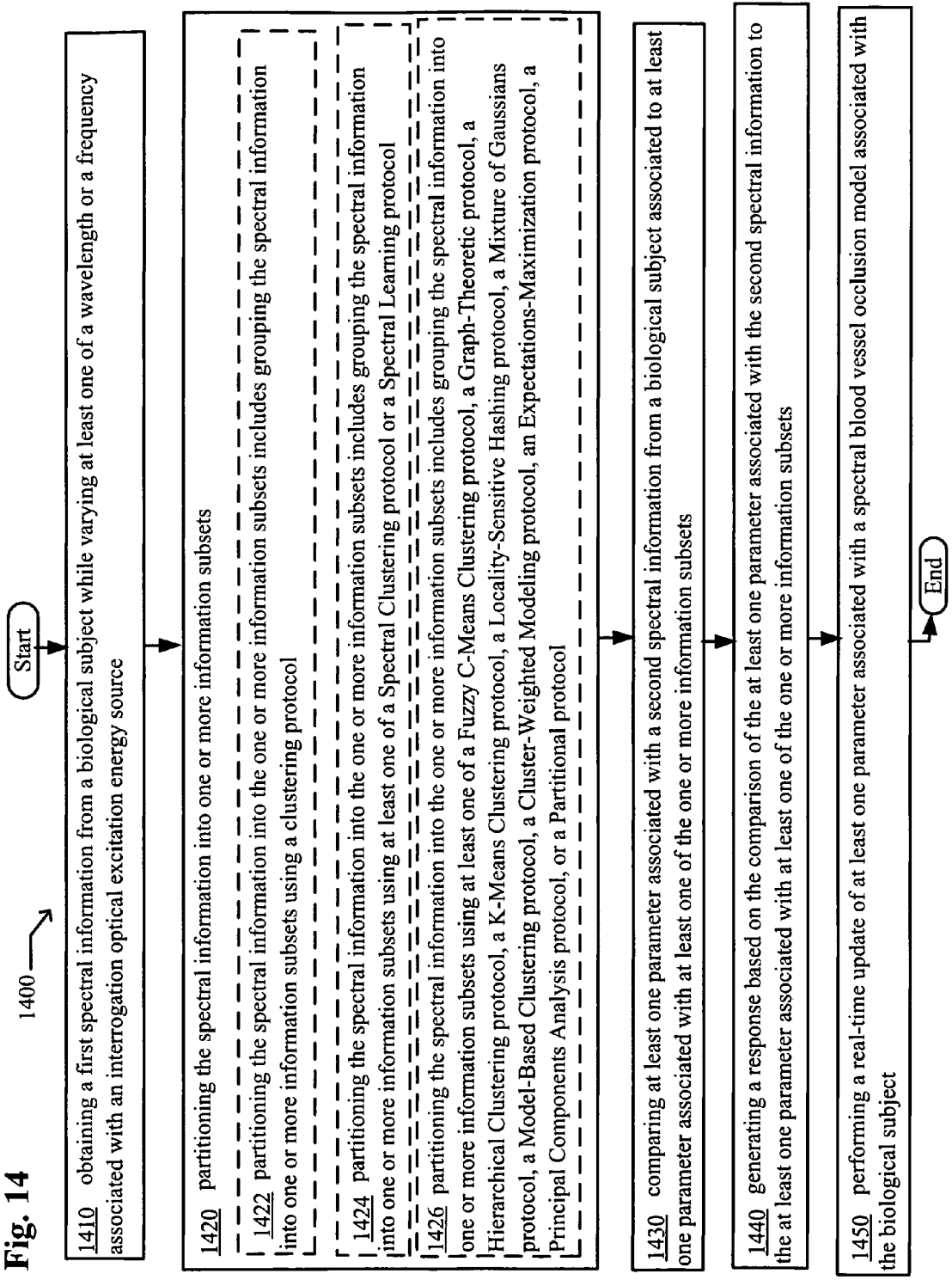

SYSTEM, DEVICES, AND METHODS FOR DETECTING OCCLUSIONS IN A BIOLOGICAL SUBJECT

CROSS-REFERENCE TO RELATED APPLICATIONS

The present application is related to and claims the benefit of the earliest available effective filing dates from the following listed applications (the "Related Applications") (e.g., claims earliest available priority dates for other than provisional patent applications or claims benefits under 35 U.S.C. §116(e) for provisional patent applications, for any and all parent, grandparent, great-grandparent, etc. applications of the Related Applications). All subject matter of the Related Applications and of any and all parent, grandparent, great-grandparent, etc. applications of the Related Applications is incorporated herein by reference to the extent such subject matter is not inconsistent herewith.

RELATED APPLICATIONS

For purposes of the United States Patent and Trademark Office (USPTO) extra-statutory requirements, the present application constitutes a continuation-in-part of U.S. patent application Ser. No. 12/004,107, entitled TREATMENT INDICATIONS INFORMED BY A PRIORI IMPLANT INFORMATION, naming Bran Ferren; Roderick A. Hyde; Muriel Y. Ishikawa; Eric C. Leuthardt; Dennis J. Rivet; Lowell L. Wood, Jr.; and Victoria Y. H. Wood as inventors, filed 18 Dec. 2007, which is currently co-pending, or is an application of which a currently co-pending application is entitled to the benefit of the filing date.

For purposes of the United States Patent and Trademark Office (USPTO) extra-statutory requirements, the present application constitutes a continuation-in-part of U.S. patent application Ser. No. 12/004,453, entitled TREATMENT INDICATIONS INFORMED BY A PRIORI IMPLANT INFORMATION, naming Bran Ferren; Roderick A. Hyde; Muriel Y. Ishikawa; Eric C. Leuthardt; Dennis J. Rivet; Lowell L. Wood, Jr.; and Victoria Y. H. Wood as inventors, filed 19 Dec. 2007, which is currently co-pending, or is an application of which a currently co-pending application is entitled to the benefit of the filing date.

For purposes of the United States Patent and Trademark Office (USPTO) extra-statutory requirements, the present application constitutes a continuation-in-part of U.S. patent application Ser. No. 12/005,122, entitled TREATMENT INDICATIONS INFORMED BY A PRIORI IMPLANT INFORMATION, naming Bran Ferren; Roderick A. Hyde; Muriel Y. Ishikawa; Eric C. Leuthardt; Dennis J. Rivet; Lowell L. Wood, Jr.; and Victoria Y. H. Wood as inventors, filed 20 Dec. 2007, which is currently co-pending, or is an application of which a currently co-pending application is entitled to the benefit of the filing date.

For purposes of the United States Patent and Trademark Office (USPTO) extra-statutory requirements, the present application constitutes a continuation-in-part of U.S. patent application Ser. No. 12/005,154, entitled TREATMENT INDICATIONS INFORMED BY A PRIORI IMPLANT INFORMATION, naming Bran Ferren; Roderick A. Hyde; Muriel Y. Ishikawa; Eric C. Leuthardt; Dennis J. Rivet; Lowell L. Wood, Jr.; and Victoria Y. H. Wood as inventors, filed 21 Dec. 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/152,265, entitled CIRCULATORY MONITORING SYSTEMS AND METHODS, naming Bran Ferren; Jeffrey John Hagen; Roderick A. Hyde; Muriel Y. Ishikawa; Eric C. Leuthardt; Dennis J. Rivet; Lowell L. Wood, Jr.; and Victoria Y. H. Wood as inventors, filed 13 May 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/152,294, entitled CIRCULATORY MONITORING SYSTEMS AND METHODS, naming Bran Ferren; Jeffrey John Hagen; Roderick A. Hyde; Muriel Y. Ishikawa; Eric C. Leuthardt; Dennis J. Rivet; Lowell L. Wood, Jr.; and Victoria Y. H. Wood as inventors, filed 13 May 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/152,639, entitled CIRCULATORY MONITORING SYSTEMS AND METHODS, naming Bran Ferren; Jeffrey John Hagen; Roderick A. Hyde; Muriel Y. Ishikawa; Eric C. Leuthardt; Dennis J. Rivet; Lowell L. Wood, Jr.; and Victoria Y. H. Wood as inventors, filed 14 May 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/152,669, entitled CIRCULATORY MONITORING SYSTEMS AND METHODS, naming Bran Ferren; Jeffrey John Hagen; Roderick A. Hyde; Muriel Y. Ishikawa; Eric C. Leuthardt; Dennis J. Rivet; Lowell L. Wood, Jr.; and Victoria Y. H. Wood as inventors, filed 14 May 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/152,846, entitled CIRCULATORY MONITORING SYSTEMS AND METHODS, naming Bran Ferren; Jeffrey John Hagen; Roderick A. Hyde; Muriel Y. Ishikawa; Eric C. Leuthardt; Dennis J. Rivet; Lowell L. Wood, Jr.; and Victoria Y. H. Wood as inventors, filed 15 May 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/152,864, entitled CIRCULATORY MONITORING SYSTEMS AND METHODS, naming Bran Ferren; Jeffrey John Hagen; Roderick A. Hyde; Muriel Y. Ishikawa; Eric C. Leuthardt; Dennis J. Rivet; Lowell L. Wood, Jr.; and Victoria Y. H. Wood as inventors, filed 15 May 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/152,868, entitled CIRCULATORY MONITORING SYSTEMS AND METHODS, naming Bran Ferren; Jeffrey John Hagen; Roderick A. Hyde; Muriel Y. Ishikawa; Eric C. Leuthardt; Dennis J. Rivet; Lowell L. Wood, Jr.; and Victoria Y. H. Wood as inventors, filed 15

May 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/152,905, entitled CIRCULATORY MONITORING SYSTEMS AND METHODS, naming Bran Ferren; Jeffrey John Hagen; Roderick A. Hyde; Muriel Y. Ishikawa; Eric C. Leuthardt; Dennis J. Rivet; Lowell L. Wood, Jr.; and Victoria Y. H. Wood as inventors, filed 15 May 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/154,138, entitled CIRCULATORY MONITORING SYSTEMS AND METHODS, naming Bran Ferren; Jeffrey John Hagen; Roderick A. Hyde; Muriel Y. Ishikawa; Eric C. Leuthardt; Dennis J. Rivet; Lowell L. Wood, Jr.; and Victoria Y. H. Wood as inventors, filed 19 May 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/154,140, entitled CIRCULATORY MONITORING SYSTEMS AND METHODS, naming Bran Ferren; Jeffrey John Hagen; Roderick A. Hyde; Muriel Y. Ishikawa; Eric C. Leuthardt; Dennis J. Rivet; Lowell L. Wood, Jr.; and Victoria Y. H. Wood as inventors, filed 19 May 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/154,162, entitled CIRCULATORY MONITORING SYSTEMS AND METHODS, naming Bran Ferren; Jeffrey John Hagen; Roderick A. Hyde; Muriel Y. Ishikawa; Eric C. Leuthardt; Dennis J. Rivet; Lowell L. Wood, Jr.; and Victoria Y. H. Wood as inventors, filed 19 May 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/154,277, entitled CIRCULATORY MONITORING SYSTEMS AND METHODS, naming Bran Ferren; Jeffrey John Hagen; Roderick A. Hyde; Muriel Y. Ishikawa; Eric C. Leuthardt; Dennis J. Rivet; Lowell L. Wood, Jr.; and Victoria Y. H. Wood as inventors, filed 20 May 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/154,420, entitled CIRCULATORY MONITORING SYSTEMS AND METHODS, naming Bran Ferren; Jeffrey John Hagen; Roderick A. Hyde; Muriel Y. Ishikawa; Eric C. Leuthardt; Dennis J. Rivet; Lowell L. Wood, Jr.; and Victoria Y. H. Wood as inventors, filed 21 May 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/154,422, entitled CIRCULATORY MONITORING SYSTEMS AND METHODS, naming Bran Ferren; Jeffrey John Hagen; Roderick A. Hyde; Muriel Y. Ishikawa; Eric C. Leuthardt; Dennis J. Rivet; Lowell L. Wood, Jr.; and Victoria Y. H. Wood as inventors, filed 21 May 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/154,652, entitled CIRCULATORY MONITORING SYSTEMS AND METHODS, naming Bran Ferren; Jeffrey John Hagen; Roderick A. Hyde; Muriel Y. Ishikawa; Eric C. Leuthardt; Dennis J. Rivet; Lowell L. Wood, Jr.; and Victoria Y. H. Wood as inventors, filed 22 May 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/154,654, entitled CIRCULATORY MONITORING SYSTEMS AND METHODS, naming Bran Ferren; Jeffrey John Hagen; Roderick A. Hyde; Muriel Y. Ishikawa; Eric C. Leuthardt; Dennis J. Rivet; Lowell L. Wood, Jr.; and Victoria Y. H. Wood as inventors, filed 22 May 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/228,141, entitled CIRCULATORY MONITORING SYSTEMS AND METHODS, naming Bran Ferren; Jeffrey John Hagen; Roderick A. Hyde; Muriel Y. Ishikawa; Eric C. Leuthardt; Dennis J. Rivet; Lowell L. Wood, Jr.; and Victoria Y. H. Wood as inventors, filed 7 Aug. 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/228,151, entitled CIRCULATORY MONITORING SYSTEMS AND METHODS, naming Bran Ferren; Jeffrey John Hagen; Roderick A. Hyde; Muriel Y. Ishikawa; Eric C. Leuthardt; Dennis J. Rivet; Lowell L. Wood, Jr.; and Victoria Y. H. Wood as inventors, filed 7 Aug. 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/228,155, entitled CIRCULATORY MONITORING SYSTEMS AND METHODS, naming Bran Ferren; Jeffrey John Hagen; Roderick A. Hyde; Muriel Y. Ishikawa; Eric C. Leuthardt; Dennis J. Rivet; Lowell L. Wood, Jr.; and Victoria Y. H. Wood as inventors, filed 7 Aug. 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/228,156, entitled CIRCULATORY MONITORING SYSTEMS AND METHODS, naming Bran Ferren; Jeffrey John Hagen; Roderick A. Hyde; Muriel Y. Ishikawa; Eric C. Leuthardt; Dennis J. Rivet; Lowell L. Wood, Jr.; and Victoria Y. H. Wood as inventors, filed 7 Aug. 2008, which is currently co-pending, or is an application of which a currently co-pending application is entitled to the benefit of the filing date.

The present application is related to U.S. patent application Ser. No. 12/387,466, entitled SYSTEM, DEVICES, AND METHODS FOR DETECTING OCCLUSIONS IN A BIOLOGICAL SUBJECT, naming Edward S. Boyden and Eric C. Leuthardt as inventors, filed 30 Apr. 2009.

The present application is related to U.S. patent application Ser. No. 12/387,458, entitled SYSTEM, DEVICES, AND METHODS FOR DETECTING OCCLUSIONS IN A BIOLOGICAL SUBJECT Including Spectral Learning, naming Edward S. Boyden and Eric C. Leuthardt as inventors, filed 30 Apr. 2009.

The present application is related to U.S. patent application Ser. No. 12/387,453, entitled SYSTEM, DEVICES, AND METHODS FOR DETECTING OCCLUSIONS IN A BIOLOGICAL SUBJECT Including Differential Spectroscopy, naming Edward S. Boyden and Eric C. Leuthardt as inventors, filed 30 Apr. 2009.

The present application is related to U.S. patent application Ser. No. 12/387,452, entitled SYSTEM, DEVICES, AND METHODS FOR DETECTING OCCLUSIONS IN A BIOLOGICAL SUBJECT, naming Edward S. Boyden and Eric C. Leuthardt as inventors, filed 30 Apr. 2009.

The USPTO has published a notice to the effect that the USPTO's computer programs require that patent applicants reference both a serial number and indicate whether an application is a continuation or continuation-in-part. Stephen G. Kunin, *Benefit of Prior-Filed Application*, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

SUMMARY

In one aspect, the present disclosure is directed to, among other things, an occlusion-monitoring system. The occlusion-monitoring system includes, but is not limited to, a body structure configured for wear by a user. In an embodiment, the body structure includes an optical energy emitter component. In an embodiment, the optical energy emitter component is configured to direct an ex vivo generated pulsed optical energy stimulus along an optical path for a time sufficient to interact with one or more regions within the biological subject. In an embodiment, the optical energy emitter component is configured to direct a pulsed optical energy stimulus along an optical path in an amount and for a time sufficient to elicit the formation of acoustic waves associated with changes in a biological mass present along the optical path.

In an embodiment, the body can include, but is not limited to, an optical energy sensor component. In an embodiment, the optical energy sensor component is configured to detect (e.g., assess, calculate, evaluate, determine, gauge, measure, monitor, quantify, resolve, sense, or the like) at least one of an emitted optical energy or a remitted optical energy and to generate a first response based on the detected at least one of the emitted optical energy or the remitted optical energy.

The occlusion-monitoring system can include, but is not limited to, one or more computer-readable memory media having blood vessel occlusion information configured as a data structure. In an embodiment, the data structure includes, but is not limited to, a characteristic spectral signature information section. In an embodiment, the characteristic spectral signature information includes at least one of characteristic embolus spectral signature information representative of the presence of at least a partial occlusion in a blood vessel, characteristic arterial embolus spectral signature information representative of the presence of at least a partial occlusion in an artery, characteristic thrombus spectral signature information representative of at least a partial blood clot formation in a blood vessel, or characteristic deep vein thrombus spectral signature information representative of at least a partial blood clot formation in a deep vein. In an embodiment, the characteristic spectral signature information can include, but is not limited to, at least one of characteristic blood component spectral signature information or tissue spectral signature information. The occlusion-monitoring system can include, but is not limited to, one or more controllers configured to compare the generated first response to the blood vessel occlusion information, and to generate a second response based on the comparison.

In an aspect, the present disclosure is directed to, among other things described herein, a method for optically detecting an embolus, thrombus, or a deep vein thrombus in a biological subject. In an embodiment, the method includes comparing a detected optical energy absorption profile of a portion of a tissue within a biological subject to characteristic spectral signature information. In an embodiment, comparing the detected optical energy absorption profile includes, but is not limited to, executing at least one of a Spectral Clustering protocol or a Spectral Learning protocol operable to compare one or more parameters associated with the detected optical energy absorption profile to one or more information subsets associated with the characteristic spectral signature information. The method can include, but is not limited to, generating a response based on the comparison of the detected optical energy absorption profile to the characteristic spectral signature information.

In an aspect, a method includes, but is not limited to, performing a real-time comparison of a first detected optical energy absorption profile of a portion of a tissue within a biological subject to characteristic spectral signature information. In an embodiment, the detected optical energy absorption profile includes at least one of an emitted optical energy or a remitted optical energy. The method can include, but is not limited to, determining whether an embolic event has occurred. The method can include, but is not limited to, obtaining a second detected optical energy absorption profile of the portion of a tissue within a biological subject. The method can include, but is not limited to, performing a real-time comparison of the second detected optical energy absorption profile to a statistical learning model associated with the biological subject. The method can include, but is not limited to, determining whether an embolic event has occurred. The method can include, but is not limited to, updating at least one parameter associated with the statistical learning model based at least in part on a parameter associated with the first detected optical energy absorption profile. The method can include, but is not limited to, activating at least one of a statistical leaning modeling protocol or a heuristic trend analysis protocol based on a result of the real-time comparison of the second detected optical energy absorption profile to at least one parameter associated with the statistical learning model.

In an aspect, a method includes, but is not limited to, comparing an optical energy spectral image profile of an anastomosed blood vessel, a bypassed blood vessel, a widened blood vessel, or an endarterectomized blood vessel to characteristic blood vessel spectral signature data. The method can include, but is not limited to, generating a response based at least in part on the comparison of the optical energy spectral image profile to the characteristic spectral signature data.

In an aspect, the present disclosure is directed to, among other things, a method for monitoring a biological subject for a condition associated with an obstructed blood vessel. The method includes, but is not limited to, automatically generating an optical energy spectral image profile of a region including a blood vessel. The method can include, but is not limited to, comparing a value associated with the generated optical energy spectral image profile to characteristic spectral signature data. The method can include, but is not limited to, automatically generating a response based at least in part on the comparison of the value associated with the generated optical energy spectral image profile to the characteristic spectral signature data.

In an aspect, the present disclosure is directed to, among other things, an article of manufacture. The article of manufacture includes, but is not limited to, a computer-readable memory medium including characteristic spectral signature information configured as a physical data structure for use in analyzing or modeling a detected optical energy spectral image profile for a biological subject. In an embodiment, the data structure includes a characteristic spectral signature data section having at least one machine-readable storage medium. In an embodiment, the at least one machine-readable storage medium includes instructions encoded thereon for enabling a processor to perform the method of determining an optical energy spectral image profile of a region within a biological subject, and comparing a value associated with the determined optical energy spectral image profile to optical energy spectral image information. In an embodiment, the at least one machine-readable storage medium includes, but is not limited to, instructions encoded thereon for enabling a processor to perform the method of generating a response based on the comparison.

In an aspect, the present disclosure is directed to, among other things, an ex vivo system. The ex vivo system includes, but is not limited to, circuitry for obtaining spectral information from a biological subject while varying at least one of a wavelength or a frequency associated with an interrogation optical excitation energy source. The ex vivo system can include, but is not limited to, circuitry for generating a response based at least in part on a comparison of at least one parameter associated with the obtained spectral information to one or more information subsets derived from partitioning spectral information associated with the biological subject.

In an aspect, the present disclosure is directed to, among other things, a hemodynamics monitoring method. The hemodynamics monitoring method includes, but is not limited to, obtaining a first spectral information from a biological subject while varying at least one of a wavelength or a frequency associated with an interrogation optical excitation energy source. The hemodynamics monitoring method can include, but is not limited to, partitioning the spectral information into one or more information subsets. The hemodynamics monitoring method can include, but is not limited to, comparing at least one parameter associated with a second spectral information from a biological subject to at least one parameter associated with at least one of the one or more information subsets. The hemodynamics monitoring method can include, but is not limited to, generating a response based on the comparison of the at least one parameter associated with the second spectral information to the at least one parameter associated with at least one of the one or more information subsets.

In an aspect, the present disclosure is directed to, among other things, a computer program product. The computer program product includes, but is not limited to, one or more signal-bearing media containing computer instructions which, when run on a computing device, cause the computing device to implement a method including obtaining a first spectral information from a biological subject while varying at least one of a wavelength or a frequency associated with an interrogation optical excitation energy source. The computer program product can include, but is not limited to, one or more signal-bearing media containing computer instructions which, when run on a computing device, cause the computing device to implement a method including partitioning the spectral information into one or more information subsets. The computer program product can include, but is not limited to, one or more signal-bearing media containing computer instructions which, when run on a computing device, cause the computing device to implement a method including comparing at least one parameter associated with a second spectral information from a biological subject to at least one parameter associated with at least one of the one or more information subsets.

In an aspect, the present disclosure is directed to, among other things, an occlusion monitoring method. The method includes obtaining spectral information from a biological subject while varying at least one of a wavelength or a frequency associated with an interrogation optical excitation energy source. The method can include, but is not limited to, comparing at least one parameter associated with the obtained spectral information to one or more information subsets derived from partitioning spectral information associated with the biological subject. The method can include, but is not limited to, generating a response based on the comparison of the at least one parameter associated with the obtained spectral information to the one or more information subsets derived from partitioning spectral information associated with the biological subject.

In an aspect, a method includes, but is not limited to, performing a real-time comparison of a first detected optical energy absorption profile of a portion of a tissue within a biological subject to characteristic spectral signature information. In an embodiment, the detected optical energy absorption profile includes at least one of an emitted optical energy or a remitted optical energy. The method can include, but is not limited to, determining whether an embolic event has occurred. The method can include, but is not limited to, obtaining a second detected optical energy absorption profile of the portion of a tissue within a biological subject. The method can include, but is not limited to, performing a real-time comparison of the second detected optical energy absorption profile to a statistical learning model associated with the biological subject. The method can include, but is not limited to, determining whether an embolic event has occurred.

In an aspect, the present disclosure is directed to, among other things, a computer system. The computer system includes, but is not limited to, a signal-bearing medium comprising spectral information associated with at least one of characteristic spectral signature information or detected optical energy absorption information associated with a portion of a tissue within a biological subject. In an embodiment, the spectral information is configured as a data structure. The computer system can include, but is not limited to, a shift register structure including a first set of shift registers having a first plurality of shift registers interconnected in series, at least one of the first plurality of registers configured to receive a clock signal having a shift frequency. In an embodiment, the first set of shift registers are configured to shift characteristic spectral signature information loaded into at least one shift register in the first set of shift registers to a next one of a shift register in the first set of shift registers according to the shift frequency. In an embodiment, the shift register structure includes a second set of shift registers having a second plurality of shift registers interconnected in series, the second set of shift registers having one or more shift register loaded with the detected optical energy absorption information. In an embodiment, the shift register structure is configured to generate a comparison of the characteristic spectral signature information loaded in one or more shift register in the first set of shift registers to the detected optical energy absorption information loaded in one or more shift register in the second set of shift registers.

In an aspect, the present disclosure is directed to, among other things, a computing device. The computing device includes, but is not limited to, an integrated circuit having a plurality of logic components. The computing device can include, but is not limited to, an input device coupled to the integrated circuit. In an embodiment, the input device is operable to provide data indicative of one or more spectral events associated with a detected at least one of a transmitted optical energy or a remitted optical energy. The computing device can include, but is not limited to, a controller coupled to the integrated circuit. In an embodiment, the controller is operable to analyze an output of one or more of the plurality of logic components and to determine at least one parameter associated with a cluster centroid deviation derived from a comparison of at least one parameter associated with the detect at least one of the transmitted optical energy or the remitted optical energy to a threshold diameter of at least one cluster associated with a set of reference cluster information.

In an aspect, a system includes, but is not limited to, a computer-readable memory medium having biological tissue information configured as a data structure. In an embodiment, the data structure can include but is not limited to a tissue spectral model having at least one of a blood spectral component, a fat spectral component, a muscle spectral component, or a bone spectral component. The system can include, but is not limited to, a controller configured to compare a measurand associated with the biological subject to a threshold value associated with the tissue spectral model and to generate a response based on the comparison.

In an aspect, a system includes, but is not limited to a computer program product. The computer program product includes, but is not limited to, one or more signal-bearing media containing computer instructions which, when run on a computing device, cause the computing device to implement a method including comparing a detected optical energy absorption profile of a portion of a tissue within a biological subject to characteristic spectral signature information, the detected optical energy absorption profile including at least one of an emitted optical energy or a remitted optical energy.

The computer program product can include, but is not limited to, signal-bearing media containing computer instructions which, when run on a computing device, cause the computing device to implement a method including generating a response based on the comparison of the detected optical energy absorption profile to the characteristic spectral signature information.

In an aspect, a system includes, but is not limited to, a computer program product, including one or more signal-bearing media containing computer instructions which, when run on a computing device, cause the computing device to implement a method including obtaining a first spectral information from a biological subject while varying at least one of a wavelength or a frequency associated with an interrogation optical excitation energy source. The computer program product can include, but is not limited to, one or more signal-bearing media containing computer instructions which, when run on a computing device, cause the computing device to implement a method including automatically partitioning the spectral information into one or more information subsets. The computer program product can include, but is not limited to, one or more signal-bearing media containing computer instructions which, when run on a computing device, cause the computing device to implement a method including comparing at least one parameter associated with a second spectral information from a biological subject to at least one parameter associated with at least one of the one or more information subsets.

In an aspect, a monitoring device includes, but is not limited to, means for emitting an interrogation energy to at least one blood vessel. The monitoring device can include, but is not limited to, means for detecting at least one of an emitted interrogation energy or a remitted interrogation energy. In an embodiment, the monitoring device can include, but is not limited to, means for detecting at least one of an emitted interrogation energy or a remitted interrogation energy associated with a blood vessel occlusion in the at least one blood vessel. The monitoring device can include, but is not limited to, means for generating one or more heuristically determined parameters associated with at least one in vivo or in vitro determined metric. In an embodiment, the monitoring device includes, but is not limited to, means for generating a response based on a comparison of a detected at least one of an emitted interrogation energy or a remitted interrogation energy to at least one heuristically determined parameter.

In an aspect, an occlusion monitoring device, device includes, but is not limited to, an interrogation energy emitter component, a sensor component, and one or more computer-readable memory media.

In an embodiment, the interrogation energy emitter component is configured to deliver at least one of an electromagnetic interrogation energy, an electrical interrogation energy, an ultrasonic interrogation energy, or a thermal interrogation energy to at least one region within the biological subject. In an embodiment, the sensor component is configured to detect at least one of an emitted energy or a remitted energy, and to generate a first response based on a detected at least one of the emitted energy or the remitted energy. In an embodiment, the one or more computer-readable memory media include blood vessel spectral occlusion information configured as a data structure, the data structure including a spectral signature information section having at least one of embolus spectral information, arterial embolus spectral information, thrombus spectral information, deep vein thrombus spectral information, blood component spectral information, or tissue spectral information.

In an aspect, a method includes, but is not limited to, comparing an optical energy spectral image profile of a revascularized region of a biological subject to characteristic blood vessel spectral signature data. The method can include, but is not limited to, generating a response based at least in part on the comparison of the optical energy spectral image profile to the characteristic spectral signature data.

In an aspect, a method includes, but is not limited to, performing a real-time comparison of a first detected optical energy absorption profile of a first region within a biological subject to characteristic spectral signature information, the detected optical energy absorption profile including at least one of an emitted optical energy or a remitted optical energy. The method can include, but is not limited to, determining whether an occlusion event has occurred. The method can include, but is not limited to, obtaining a second detected optical energy absorption profile of a second region within a biological subject, the second region having a different location from the first region. The method can include, but is not limited to, performing a real-time comparison of the second detected optical energy absorption profile to characteristic spectral signature information. The method can include, but is not limited to, determining whether an occlusion event has occurred.

In an aspect, a method includes, but is not limited to, performing a real-time comparison of at least a first detected optical energy absorption profile of a first location within a biological subject to a second detected optical energy absorption profile of a second location within a biological subject. The method can include, but is not limited to, determining whether an embolic event has occurred. The method can include, but is not limited to, performing a real-time comparison of at least one of the first detected optical energy absorption profile of the first location within a biological subject, the second detected optical energy absorption profile of the second location within the biological subject, or a difference of at least one spectral component thereof to a statistical learning model associated with the biological subject. The method can include, but is not limited to, determining whether an embolic event has occurred.

In an aspect, a method includes, but is not limited to, performing a real-time comparison of at least a first detected optical energy absorption profile of a first location within a biological subject to a second detected optical energy absorption profile of a second location within a biological subject. The method can include, but is not limited to, determining whether an embolic event has occurred. The method can include, but is not limited to, performing a real-time comparison of at least one of the first detected optical energy absorption profile, the second detected optical energy absorption profile, or a difference of at least one spectral component thereof to characteristic spectral signature information. The method can include, but is not limited to, generating a response based at least in part on the comparison.

In an aspect, a method includes, but is not limited to, performing a real-time comparison of at least a first detected optical energy absorption profile and a second detected optical energy absorption profile of a region within a biological subject. The method can include, but is not limited to, determining whether an embolic event has occurred. The method can include, but is not limited to, performing a real-time comparison of at least one of the first detected optical energy absorption profile, the second detected optical energy absorption profile, or a difference of at least one spectral component thereof to characteristic spectral signature information. The method can include, but is not limited to, generating a response based at least in part on the comparison.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIGS. 10A and 10B are flow diagrams of a method according to one illustrated embodiment.

FIGS. 13A and 13B are flow diagrams of a method according to one illustrated embodiment.

FIG. 14 is a flow diagram of a method according to one illustrated embodiment.

DETAILED DESCRIPTION

Figure 1:
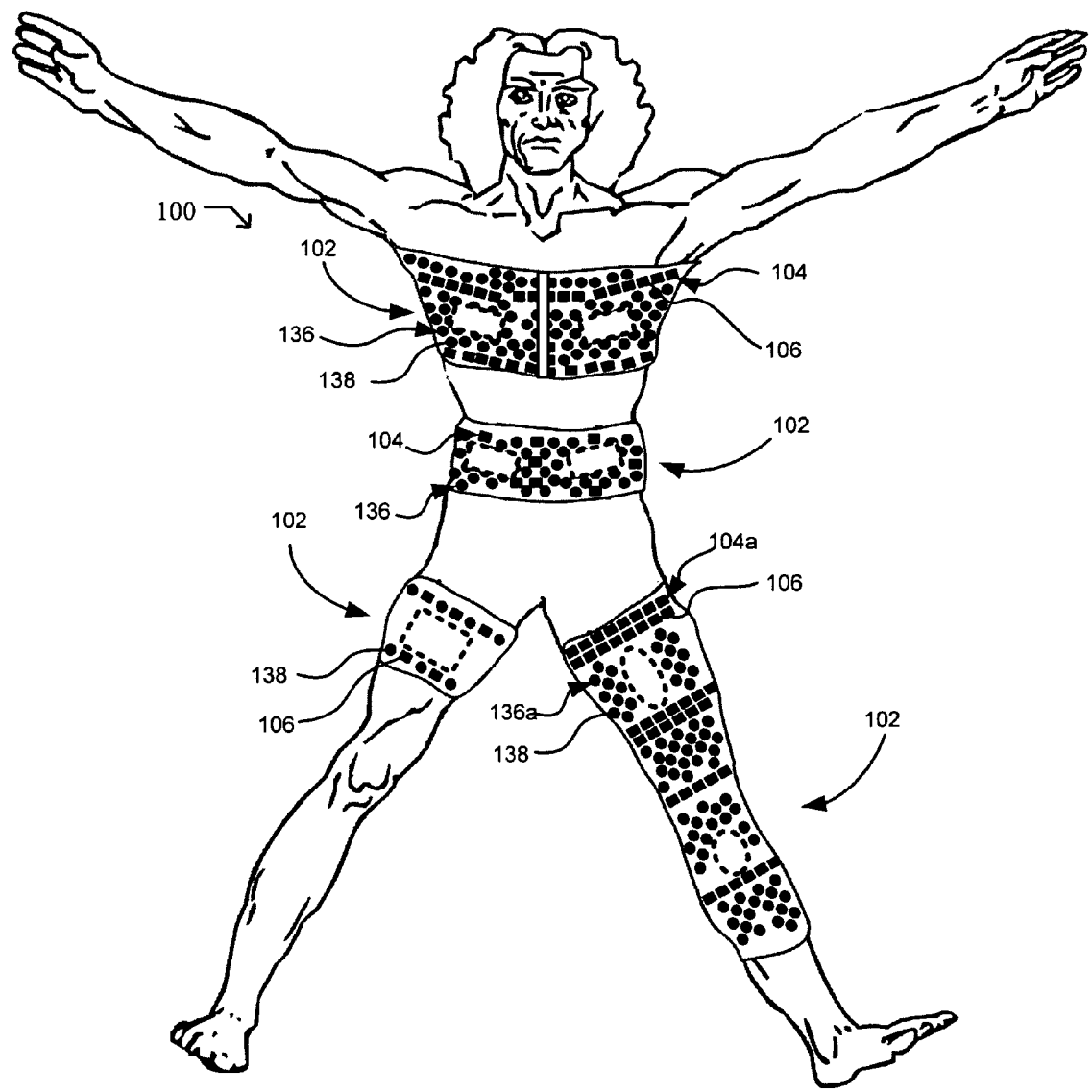
FIG. 1 is a perspective view of a system including one or more monitoring devices according to one illustrated embodiment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Cardiovascular disorders are a leading cause of death and disability in the United States. See, e.g., Heron et al., *Deaths: Preliminary Data for* 2006, National Vital Statistics Report, Vol. 56, No. 16, Table B (2008). A number of those cardiovascular disorders are associated with the formation of intravascular obstructions including, for example, embolism, thrombosis, infarction, and ischemia. An embolism generally involves an obstruction or an occlusion of a vessel (e.g., a body fluid vessel, a blood vessel) by an object (i.e., an embolus). The object (e.g., a mass, a gas bubble, a detached blood clot, a blood component aggregate, a clump of bacteria, a foreign body, plaque, or the like, or other material or substance) migrates from one part of the body through, for example, circulation and causes a blockage (occlusion) of a blood vessel in another part of the body. Thrombosis generally involves an obstruction or an occlusion of a vessel by the formation of a thrombus or blood clot at the blockage point within a blood vessel. Embolism and thrombosis are responsible for a grim litany of health problems, including stroke, heart attack, pulmonary embolism, and complications of cancer.

As a non-limiting example, certain systems, devices, and methods, described herein provide a monitoring device configured to, for example, actively sense, treat, or prevent an occlusion (e.g. a thrombus, an embolus, or the like), a hematological abnormality, a body fluid flow abnormality, or the like. As a non-limiting example, certain systems, devices, and methods, described herein provide technologies or methodologies for actively sensing, treating, or preventing an intravascular obstruction.

An aspect includes systems, devices, and methods for detecting (e.g., optically detecting, ultrasonically detecting, thermally detecting, acoustically detecting, energetically detecting, spectroscopically detecting, or the like) an embolus, thrombus, or a deep vein thrombus in a biological subject. Another non-limiting approach includes systems, devices, and methods for detecting one or more materials, substances, chemicals, components, or the like associated with an embolus, thrombus, or a deep vein thrombus in a biological subject.

An aspect includes systems, devices, and methods for diagnosing the presence of a condition associated with an obstructed blood vessel. One non-limiting approach for diagnosing the presence of a condition associated with an obstruction of a flow in a blood vessel includes spectral learning techniques and methodologies for predicting the onset of obstructions in blood vessels.

An aspect includes systems, devices, and methods, including an ex vivo monitoring device configured to detect the formation or presence of an in vivo occlusion in a biological subject. One non-limiting approach for detecting the formation or presence of an in vivo occlusion includes systems, devices, and methods including time-integrated analysis components. A non-limiting approach for detecting the formation or presence of an in vivo occlusion includes systems, devices, and methods including spectral learning technologies. A non-limiting approach for detecting the formation or presence of an in vivo occlusion includes systems, devices, and methods including spectral learning and real-time spectral model updating methodologies and technologies.

An aspect includes systems, devices, and methods for real-time modeling of an embolic or thrombotic event. A non-limiting approach for real-time modeling of an embolic or thrombotic event includes real-time spectral learning and real-time spectral modeling methodologies and technologies.

FIG. 1 shows a system 100 in which one or more methodologies or technologies may be implemented such as, for example, actively sensing, treating, or preventing an occlusion (e.g., a thrombus, an embolus, or the like), a hematological abnormality, a body fluid flow abnormality, or the like. In an embodiment, the system 100 is configured to detect an energy absorption profile of a portion of a tissue within a biological subject. In an embodiment, the system 100 is configured to obtain a spectral image profile of a region including a blood vessel. In an embodiment, the system 100 is configured to determine an occlusion aggregation rate. In an embodiment, the system 100 is configured to obtain spectral information from a biological subject while varying at least one of a wavelength or a frequency associated with an interrogation energy source (e.g., electromagnetic energy source, optical energy source, ultrasonic energy source, electrical energy source, thermal energy source, or the like). In an embodiment, the system 100 is configured to non-invasively determine one or more tissue optical properties.

In an embodiment, the system 100 is configured to perform non-invasive, real-time imagining of blood vessel occlusions. In an embodiment, the system 100 is configured to assess the effect of antithrombotic agents. In an embodiment, the system 100 is configured to measure a concentration of endogenous or exogenous chromophores. In an embodiment, the system 100 is configured to detect remitted light from a tissue, in vivo. In an embodiment, the system 100 is configured to measure at least one parameter associated with the formation or onset of a condition associated with an occlusion, a hematological abnormality, a body fluid flow abnormality, or the like.

In an embodiment, the system 100 is configured to measure at least one parameter associated with at least one of a blood spectral component, a fat spectral component, a muscle spectral component, a bone spectral component, or the like. In an embodiment, the system 100 is configured to measure at least one parameter associated with at least one of a hair spectral component or a lymphatic system tissue spectral component. In an embodiment, the system 100 is configured to measure at least one parameter associated with an implanted device spectral component.

In an embodiment, the system 100 is configured to compare a measurand associated with the biological subject to a threshold value associated with the tissue spectral model and to generate a response based on the comparison.

As a non-limiting example, certain systems, devices, and methods, described herein provide technologies or methodologies for actively sensing, treating, or preventing an intravascular obstruction present in, for example, dense tissue or regions of that are spectrally complex. In an embodiment, the system 100 is configured to obtain spectral information associated with an occlusion by detecting spectral differences between a first and a second region of the biological subject. Such "differential" measurements may allow for better signal to noise, and may minimize the effect of other spectral parameters of the body that vary over time.

In an embodiment, the system 100 is configured to isolate blood spectral information by, for example, subtracting spectral information associated with one or more different tissues. In an embodiment, the system 100 is configured to, for example, isolate blood spectral information by subtracting at least one of bone spectral information, fat spectral information, muscle spectral information, or the like, or other tissue spectral information. In an embodiment, the system 100 is configured to, for example, isolate blood spectral information by subtracting at spectral information associated with an implantable device.

In an embodiment, the system 100 is configured as a "differential mode" spectrometer. For example, in an embodiment, the system 100 is configured to detect spectral information associated with a first region of a biological subject (e.g., a first blood vessel) and to detect spectral information associated with a second region of the biological subject (e.g., a second blood vessel). In an embodiment, the system 100 is configured compare to the detected spectral information from the first region to the second region, and to generate a response based on the comparison. In an embodiment, the system 100 is configured to compare to first detected spectral information from a region within the biological subject to at least second detected spectral information of the same region, and to generate a response based on the comparison. In an embodiment, the system 100 is configured to concurrently or sequentially detect a first spectral information and at least a second spectral information.

One of the many complications associated with surgery are blood clots. For example, blood clots in the legs (deep vein thrombosis) can develop from long periods of immobility. Should these clots dislodge, they can travel in the bloodstream to the lungs, where they can restrict blood circulation through the lungs (pulmonary embolism). As a result, the oxygen supply to the rest of the body may decrease, and blood pressure could fall. In an embodiment, the system 100 is configured to monitor users prior, during, or after invasive procedures. For example, in an embodiment, the system 100 is configured to monitor users prior, during, or after a revascularization procedure. In an embodiment, the system 100 is configured to monitor users prior, during, or after a carotid endarterectomy. In an embodiment, the system 100 is configured to monitor users prior, during, or after a body fluid vessel widening procedure (e.g., an angioplasty procedure) or a body fluid vessel cleaning out procedure. In an embodiment, the system 100 is configured to monitor at least one of an inflammation marker or a blood-clotting marker for a target time period or time periods.

Infections account for many other complications associated with surgery. During an infection, an infecting agent (e.g., fungi, micro-organisms, parasites, pathogens (e.g., viral pathogens, bacterial pathogens, and the like), prions, viroids, viruses, and the like) generally interferes with the normal functions of a biological subject. In some cases, this causes chronic wounds, gangrene, loss of infected tissue or infected limb, and occasionally death. In an embodiment, the system 100 is configured to monitor one or more inflammation markers, and one or more and blood-clotting markers prior, during or after invasive procedures.

In an embodiment, the system 100 is configured to monitor one or more imaging probes associated with at least one inflammation marker. In an embodiment, the system 100 is configured to monitor one or more imaging probes associated with at least one inflammation marker, and one or more imaging probes associated with at least one blood-clotting marker prior, during or after invasive procedures.

The system 100 can include, but is not limited to, one or more monitoring devices 102. In an embodiment, the monitoring device 102 is configured to monitor a condition associated with an occlusion within a body fluid vessel. In an embodiment, the monitoring device 102 is configured to detect the onset or the presence of a condition associated with a venous or arterial thrombus. In an embodiment, the monitoring device 102 is configured to provide early detection of a formation or presence of an occlusion within a body fluid vessel.

The spectral parameters of blood and its components may depend on many factors including, but not limited to, flow-velocity, haematocrit value, haemolysis, osmolarity, oxygen saturation, or the like. In an embodiment, the monitoring device 102 is configured to detect one or more parameters associated with one or more blood components. In an embodiment, the monitoring device 102 is configured to detect one or more parameters associated with a change (e.g., a rate, a rate change, a change in concentration, an aggregation rate, or the like) associated with one or more blood components. In an embodiment, the monitoring device 102 is configured to automatically provide real-time information regarding a condition associated with an occlusion of a body fluid vessel. In an embodiment, the monitoring device 102 is configured to acquire spectral information associated with one or more biomarkers (e.g., biomarkers for ischemia, biomarkers for a pulmonary embolus, biomarkers indicative of an occlusion, a thrombus, or the like).

In an embodiment, the monitoring device 102 is configured to acquire spectral information associated with a pathological condition. In an embodiment, the monitoring device 102 is configured to reduce the risk associated with an intravascular obstruction. In an embodiment, the monitoring device 102 is configured to treat high-risk users with arterial or cardiac sources of embolism. In an embodiment, the monitoring device 102 is configured to measure at least one parameter associated with the formation or onset of a condition associated with an occlusion, a hematological abnormality, a body fluid flow abnormality, or the like. In an embodiment, the monitoring device 102 is configured to measure at least one parameter associated with at least one of a blood spectral component, a fat spectral component, a muscle spectral component, a bone spectral component, or the like. In an embodiment, the monitoring device 102 is configured to model an embolic or thrombotic event in real-time. In an embodiment, the monitoring device 102 is configured to localize an embolic source.

In an embodiment, the monitoring device 102 is configured for non-invasive, real-time imagining of biological tissue. In an embodiment, the monitoring device 102 is configured for non-invasive, real-time imagining of changes associated with one or more blood components. In an embodiment, the monitoring device 102 is configured for non-invasive imagining of in vivo occlusions. In an embodiment, the monitoring device 102 is configured for deep-tissue optical imaging. In an embodiment, the monitoring device 102 is configured for in vivo diagnostic imaging. In an embodiment, the monitoring device 102 is configured for real-time spectral detection and analysis of occlusions, hematological abnormalities, body fluid flow abnormalities, or the like.

The system 100 can include, but is not limited to, at least one energy emitter component 104 including one or more energy emitters 106. Among energy emitters 106 examples include, but are not limited to, electrical energy emitters, electromagnetic energy emitters, optical energy emitters, energy photon emitters, light energy emitters, and the like. Further examples of energy emitters 106 include, but are not limited to, electric circuits, electrical conductors, electrodes (e.g., nano- and micro-electrodes, patterned-electrodes, electrode arrays (e.g., multi-electrode arrays, micro-fabricated multi-electrode arrays, patterned-electrode arrays, and the like), electrocautery electrodes, and the like), cavity resonators, conducting traces, ceramic patterned electrodes, electromechanical components, lasers, quantum dots, laser diodes, light-emitting diodes (e.g., organic light-emitting diodes, polymer light-emitting diodes, polymer phosphorescent light-emitting diodes, microcavity light-emitting diodes, high-efficiency UV light-emitting diodes, and the like), arc flashlamps, continuous wave bulbs, and the like. Energy emitters 106 forming part of the energy emitter component 104, can take a variety of forms, configurations, and geometrical patterns including for example, but not limited to, a one-, two-, or three-dimensional arrays, a pattern comprising concentric geometrical shapes, a pattern comprising rectangles, squares, circles, triangles, polygons, any regular or irregular shapes, or the like, or any combination thereof. One or more of the energy emitters 106 may have a peak emission wavelength in the x-ray, ultraviolet, visible, infrared, near infrared, microwave, or radio frequency spectrum.

Figure 2:
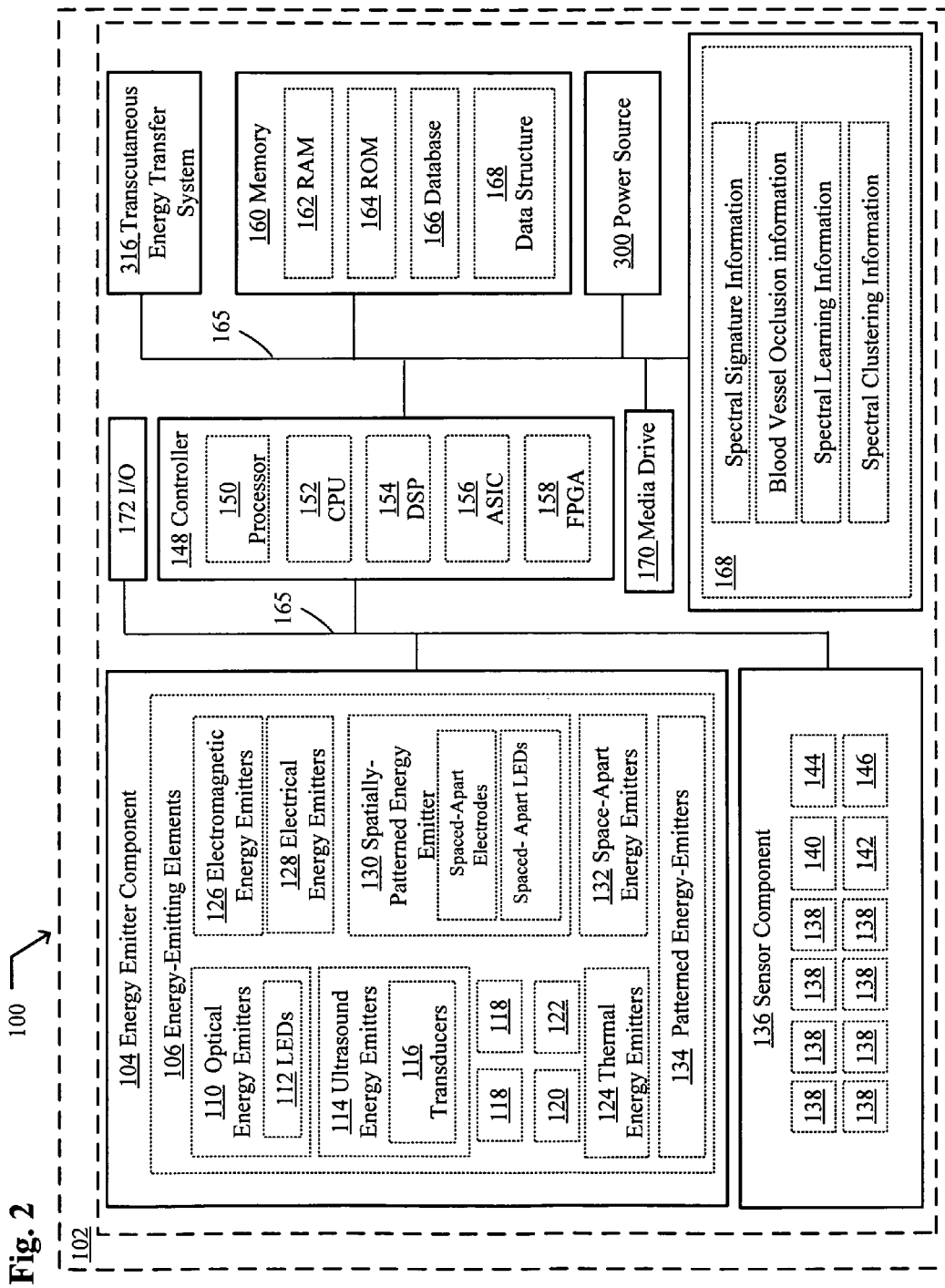
FIG. 2 is a schematic diagram of a system including one or more monitoring devices according to one illustrated embodiment.

Referring to FIGS. 1 and 2 showing various configurations of a system 100 in which one or more methodologies or technologies may be implemented, in an embodiment, the energy emitter component 104 includes one or more energy emitters 106. In an embodiment, the system 100 includes a means for emitting an interrogation energy including, for example, an energy emitter component 104 having one or more energy emitters 106. In an embodiment, the one or more energy emitters 106 are configured to generate an interrogation energy stimulus. In an embodiment, the one or more energy emitters 106 are configured to deliver energy to a region of the biological subject. In an embodiment, the one or more energy emitters 106 are configured to direct an emitted energy to tissue proximate the monitoring device 102. In an embodiment, the one or more energy emitters 106 are configured to deliver an in vivo interrogation waveform to a biological subject. In an embodiment, the one or more energy emitters 106 are configured to generate one or more continuous or a pulsed energy waves, or combinations thereof.

In an embodiment, the energy emitter component 104 includes an optical energy emitter component 104a. In an embodiment, the optical energy emitter component 104a is configured to irradiate at least one region within the biological subject with energy having at least a first peak emission wavelength ranging from about 600 nm to about 850 nm, and at least a second peak emission wavelength ranging from about 850 nm to about 1000 nm. In an embodiment, the optical energy emitter component 104a is configured to irradiate at least one region within the biological subject with energy having at least a first peak emission wavelength ranging from about 630 nm to about 660 nm, and at least a second peak emission wavelength ranging from about 660 nm to about 990 nm.

In an embodiment, the optical energy emitter component 104a is configured to direct optical energy along an optical path of sufficient strength or duration to interact with one or more regions within the biological subject. In an embodiment, a portion of the optical energy is directed to a portion of an optical energy emitter component 104a that is in optical communication along the optical path.

In an embodiment, the optical energy emitter component 104a is configured to direct a pulsed optical energy waveform along an optical path of a character and for a time sufficient to cause at least a portion of a tissue interrogated by the pulsed optical energy waveform to temporarily expand. In an embodiment, the optical energy emitter component 104a is configured to direct a pulsed optical energy stimulus along an optical path in an amount and for a time sufficient to elicit the formation of acoustic waves associated with changes in a biological mass present along the optical path. In an embodiment, the optical energy emitter component 104a is configured to generate one or more non-ionizing laser pulses in an amount and for a time sufficient to induce the formation of sound waves associated with changes in at least a partial embolism present along the optical path.

In an embodiment, the energy emitter component 104 includes one or more optical energy emitters 110. In an embodiment, the energy emitter component 104 includes one or more light-emitting diodes 112. Light-emitting diodes 112 come in a variety of forms and types including, for example, standard, high intensity, super bright, low current types, and the like. Typically, the light-emitting diode's color is determined by the peak wavelength of the light emitted. For example, red light-emitting diodes have a peak emission ranging from about 610 nm to about 660 nm. Examples of light-emitting diode colors include amber, blue, red, green, white, yellow, orange-red, ultraviolet, and the like. Further non-limiting examples of light-emitting diodes include bi-color, tri-color, and the like. Light-emitting diode's emission wavelength may depend on a variety of factors including, for example, the current delivered to the light-emitting diode. The color or peak emission wavelength spectrum of the emitted light may also generally depends on the composition or condition of the semi-conducting material used, and may include, but is not limited to, peak emission wavelengths in the infrared, visible, near-ultraviolet, or ultraviolet spectrum, or combinations thereof.

Light-emitting diodes 112 can be mounted on, for example, but not limited to a surface, a substrate, a portion, or a component of the occlusion-monitoring system 102 using a variety of methods and technologies including, for example, wire bonding, flip chip, controlled collapse chip connection, integrated circuit chip mounting arrangement, and the like. In an embodiment, the light-emitting diodes 112 can be mounted on a surface, substrate, portion, or component of the monitoring device 102 using, for example, but not limited to a flip-chip arrangement. A flip-chip is one type of integrated circuit chip mounting arrangement that generally does not require wire bonding between chips. In an embodiment, instead of wire bonding, solder beads or other elements can be positioned or deposited on chip pads such that when the chip is mounted, electrical connections are established between conductive traces carried by circuitry within the system 100.

In an embodiment, the energy emitter component 104 includes one or more light-emitting diode arrays. In an embodiment, the energy emitter component 104 includes at least one of a one-dimensional light-emitting diode array, a two-dimensional light-emitting diode array, or a three-dimensional light-emitting diode array. In an embodiment, the energy emitter component 104 includes at least one of an arc flashlamp, a laser, a laser diode, a light emitting diode, a continuous wave bulb, or a quantum dot. In an embodiment, the energy emitter component 104 includes at least one two-photon excitation component. In an embodiment, the energy emitter component 104 includes at least one of an exciplex laser, a diode-pumped solid state laser, or a semiconductor laser.

In an embodiment, the energy emitter component 104 includes one or more ultrasound energy emitters 114. In an embodiment, the energy emitter component 104 includes one or more transducers 116 (e.g., ultrasonic transducers, ultrasonic sensors, and the like). In an embodiment, the one or more transducers 116 are configured to deliver an ultrasonic interrogation stimulus (e.g., an ultrasonic non-thermal stimulus, an ultrasonic thermal stimulus, or the like) to a region within the biological subject. In an embodiment, the one or more transducers 116 are configured to generate an ultrasonic stimulus to tissue proximate the monitoring device 102. In an embodiment, the one or more transducers 116 are configured to detect an ultrasonic signal. In an embodiment, the one or more transducers 116 are configured to transmit and receive ultrasonic waves. In an embodiment, the one or more transducers 116 are configured to deliver an ultrasonic stimulus to tissue proximate the monitoring device 102. In an embodiment, the one or more transducers 116 are configured to deliver an in vivo ultrasonic interrogation waveform to a biological subject. In an embodiment, the one or more transducers 116 are configured to generate one or more continuous or a pulsed ultrasonic waves, or combinations thereof.

Among transducers 116, examples include, but are not limited to, acoustic transducers, composite piezoelectric transducers, conformal transducers, flexible transducers, flexible ultrasonic multi-element transducer arrays, flexible ultrasound transducers, immersible ultrasonic transducers, integrated ultrasonic transducers, micro-fabricated ultrasound transducers, piezoelectric materials (e.g., lead-zirconate-titanate, bismuth titanate, lithium niobate, piezoelectric ceramic films or laminates, sol-gel sprayed piezoelectric ceramic composite films or laminates, piezoelectric crystals, and the like), piezoelectric ring transducers, piezoelectric transducers, ultrasonic sensors, ultrasonic transducers, and the like. In an embodiment, the energy emitter component 104 includes one or more one-dimensional transducer arrays, two-dimensional transducer arrays, or three-dimensional transducer arrays. The one or more transducers 116 can include a single design where a single piezoelectric component outputs one single waveform at a time, or may be compound where two or more piezoelectric components are utilized in a single transducer 116 or in multiple transducers 116 thereby allowing multiple waveforms to be output sequentially or concurrently.

In an embodiment, the system 100 includes, but is not limited to, electro-mechanical components for generating, transmitting, or receiving waves (e.g., ultrasonic waves, electromagnetic waves, or the like). For example, in an embodiment, the system 100 can include, but is not limited to, one or more waveform generators 118, as well as any associated hardware, software, and the like. In an embodiment, the system 100 includes one or more controllers configured to concurrently or sequentially operate multiple transducers 116. In an embodiment, the system 100 can include, but is not limited to, multiple drive circuits (e.g., one drive circuit for each transducer 116) and may be configured to generate varying waveforms from each coupled transducer 116 (e.g., multiple waveform generators, and the like). The system 100 can include, but is not limited to, an electronic timing controller coupled to an ultrasonic waveform generator. In an embodiment, one or more controller are configured to automatically control one or more of a frequency, a duration, a pulse rate, a duty cycle, or the like associate with the ultrasonic energy generated by the one or more transducers 116. In an embodiment, one or more controller are configured to automatically control one or more of a frequency, a duration, a pulse rate, a duty cycle, or the like associate with the ultrasonic energy generated by the one or more transducers 116 based on at least one characteristic associated with an occlusion, a hematological abnormality, a body fluid flow abnormality, or the like.

In an embodiment, the one or more transducers 116 can be communicatively coupled to one or more of the waveform generator 118. In an embodiment, a waveform generators 118 can include, but is not limited to, an oscillator 120 and a pulse generator 122 configured to generate one or more drive signals for causing one or more transducer 116 to ultrasonically vibrate and generate ultrasonic energy. In an embodiment, one or more controllers 148 are configured to automatically control least one waveform characteristic (e.g., intensity, frequency, pulse intensity, pulse duration, pulse ratio, pulse repetition rate, and the like) associated with the delivery of one or more ultrasonic energy stimuli. For example, pulsed waves may be characterized by the fraction of time the ultrasound is present over one pulse period. This fraction is called the duty cycle and is calculated by dividing the pulse time ON by the total time of a pulse period (e.g., time ON plus time OFF). In an embodiment, a pulse generator 120 may be configured to electronically generate pulsed periods and non-pulsed (or inactive) periods.

The system 100 can include, but is not limited to, at least one energy emitter component 104 including one or more thermal energy emitters 124. The system 100 can include, but is not limited to, at least one energy emitter component 104 including one or more electromagnetic energy emitters 126. The system 100 can include, but is not limited to, at least one energy emitter component 104 including one or more electrical energy emitters 128. The system 100 can include, but is not limited to, at least one energy emitter component 104 including one or more spatially-patterned energy emitters 130. The system 100 can include, but is not limited to, at least one energy emitter component 104 including one or more spaced-apart energy emitters 132. The system 100 can include, but is not limited to, at least one energy emitter component 104 including one or more patterned energy emitters 134.

The system 100 can include, but is not limited to, one or more sensor components 136 including one or more sensors 138. In an embodiment, the sensor component 136 is configured to detect (e.g., assess, calculate, evaluate, determine, gauge, measure, monitor, quantify, resolve, sense, or the like) at least one characteristic (e.g., a spectral characteristic, a spectral signature, a physical quantity, an environmental attribute, a physiologic characteristic, or the like) associated with a region within the biological subject. In an embodiment, the sensor component 136 is configured to detect at least one of an energy absorption profile or an energy reflection profile of a region within a biological subject. The system 100 can include, but is not limited to, means for detecting at least one of an emitted interrogation energy or a remitted interrogation energy including one or more sensor components 136 having one or more sensors 138.

In an embodiment, sensor component 136 includes of an optical energy sensor component 136a, and the energy emitter component 104 includes of an optical energy emitter component 104a. In an embodiment, the system 100 is configure to non-invasive determine a tissue optical properties, such as, for example, a transport scattering coefficient or an absorption coefficient. In an embodiment, the optical energy emitter component 104a is configured to direct an ex vivo generated pulsed optical energy along an optical path for a time sufficient to interact with one or more regions within the biological subject and for a time sufficient for a portion of the ex vivo generated pulsed optical energy to reach a portion of the optical energy sensor component 136a that is in optical communication along the optical path. In an embodiment, the optical energy emitter component 104a is configured to direct optical energy along an optical path for a time sufficient to interact with one or more regions within the biological subject and with at least a portion of the optical energy sensor component 136a that is in optical communication along the optical path.

Among the one or more sensors 138 examples include, but are not limited to, biosensors, blood volume pulse sensors, conductance sensors, electrochemical sensors, fluorescence sensors, force sensors, heat sensors (e.g., thermistors, thermocouples, and the like), high resolution temperature sensors, differential calorimeter sensors, optical sensors, goniometry sensors, potentiometer sensors, resistance sensors, respiration sensors, sound sensors (e.g., ultrasound), Surface Plasmon Band Gap sensor (SPRBG), physiological sensors, surface plasmon sensors, and the like. Further non-limiting examples of sensors include affinity sensors, bioprobes, biostatistics sensors, enzymatic sensors, in-situ sensors (e.g., in-situ chemical sensor), ion sensors, light sensors (e.g., visible, infrared, and the like), microbiological sensors, micro-hotplate sensors, micron-scale moisture sensors, nanosensors, optical chemical sensors, single particle sensors, and the like. Further non-limiting examples of sensors include chemical sensors, cavitand-based supramolecular sensors, deoxyribonucleic acid sensors (e.g., electrochemical DNA sensors, and the like), supramolecular sensors, and the like. In an embodiment, at least one of the one or more sensors 138 is configured to detect or measure the presence or concentration of specific target chemicals (e.g., blood components, infecting agents, infection indication chemicals, inflammation indication chemicals, diseased tissue indication chemicals, biological agents, molecules, ions, and the like).

Further examples of the one or more sensors 138 include, but are not limited to, chemical transducers, ion sensitive field effect transistors (ISFETs), ISFET pH sensors, membrane-ISFET devices (MEMFET), microelectronic ion-sensitive devices, potentiometric ion sensors, quadruple-function ChemFET (chemical-sensitive field-effect transistor) integrated-circuit sensors, sensors with ion-sensitivity and selectivity to different ionic species, and the like.

In an embodiment, the sensor component 136 comprises an optical energy sensor component 136a. In an embodiment, the optical energy sensor component 136a includes an imaging spectrometer. In an embodiment, the optical energy sensor component 136a comprises at least one of a photo-acoustic imaging spectrometer, a thermo-acoustic imaging spectrometer, or a photo-acoustic/thermo-acoustic tomographic imaging spectrometer. In an embodiment, optical energy sensor component 136a includes at least one of a thermal detector, a photovoltaic detector, or a photomultiplier detector. In an embodiment, the optical energy sensor component 136a includes at least one of a charge coupled device, a complementary metal-oxide-semiconductor device, a photodiode image sensor device, a Whispering Gallery Mode (WGM) micro cavity device, or a scintillation detector device. In an embodiment, the optical energy sensor component 136a includes one or more ultrasonic transducers. In an embodiment, the optical energy sensor component 136a includes at least one of a time-integrating optical component 140, a linear time-integrating component 142, a nonlinear optical component 144, or a temporal autocorrelating component 146. In an embodiment, the optical energy sensor component 136a includes one or more one-, two-, or three-dimensional photodiode arrays.

In an embodiment, the sensor component 136 is configured to detect at least one of an emitted energy or a remitted energy associated with a biological subject. In an embodiment, the sensor component 136 is configured to detect at least one of an emitted interrogation energy or a remitted interrogation energy. In an embodiment, the sensor component 136 is configured to detect an optical energy absorption profile of a portion of a tissue within a biological subject. In an embodiment, the sensor component 136 is configured to detect an excitation radiation and an emission radiation associated with a portion of a tissue within a biological subject.

In an embodiment, the sensor component 136 is configured to detect at least one of an emitted energy or a remitted energy associated with a tissue of a biological subject. Blood is a tissue composed of, among other components, formed elements (e.g., blood cells such as erythrocytes, leukocytes, thrombocytes, and the like) suspend in a matrix (plasma). The heart, blood vessels (e.g., arteries, arterioles, capillaries, veins, venules, or the like), and blood components, make up the cardiovascular system. The cardiovascular system, among other things, moves oxygen, gases, and wastes to and from cells and tissues, maintains homeostasis by stabilizing body temperature and pH, and helps fight diseases.

In an embodiment, the sensor component 136 is configured to detect at least one of an emitted energy or a remitted energy associated with a portion of a cardiovascular system. In an embodiment, the sensor component 136 is configured to detect at least one of an emitted energy or a remitted energy associated with one or more blood components within a biological subject. In an embodiment, the sensor component 136 is configured to detect at least one of an emitted energy or a remitted energy associated with one or more formed elements within a biological subject. In an embodiment, the sensor component 136 is configured to detect a spectral profile of one or more blood components. In an embodiment, the sensor component 136 is configured to detect an optical energy absorption of one or more blood components.

Examples of detectable blood components include, but are not limited to, erythrocytes, leukocytes (e.g., basophils, granulocytes, eosinophils, monocytes, macrophages, lymphocytes, neutrophils, or the like), thrombocytes, acetoacetate, acetone, acetylcholine, adenosine triphosphate, adrenocorticotrophic hormone, alanine, albumin, aldosterone, aluminum, amyloid proteins (non-immunoglobulin), antibodies, apolipoproteins, ascorbic acid, aspartic acid, aspartic acid, bicarbonate, bile acids, bilirubin, biotin, blood urea Nitrogen, bradykinin, bromide, cadmium, calciferol, calcitonin (ct), calcium, carbon dioxide, carboxyhemoglobin (as HbcO), cell-related plasma proteins, cholecystokinin (pancreozymin), cholesterol, citric acid, citrulline, complement components, coagulation factors, coagulation proteins, complement components, c-peptide, c-reactive protein, creatine, creatinine, cyanide, 11-deoxycortisol, deoxyribonucleic acid, dihydrotestosterone, diphosphoglycerate (phosphate), or the like.

Further examples of detectable blood components include, but are not limited to dopamine, enzymes, total, epidermal growth factor, epinephrine, ergothioneine, erythrocytes, erythropoietin, folic acid, fructose, furosemide glucuronide, galactoglycoprotein, galactose (children), gamma-globulin, gastric inhibitory peptide, gastrin, globulin, α-1-globulin, α-2-globulin, α-globulins, β-globulin, β-globulins, glucagon, glucosamine, glucose, immunoglobulins (antibodies), lipase p, lipids, total, lipoprotein (sr 12-20), lithium, low-molecular weight proteins, lysine, lysozyme (muramidase), α 2-macroglobulin, γ-mobility (non-immunoglobulin), pancreatic polypeptide, pantothenic acid, para-aminobenzoic acid, parathyroid hormone, pentose, phosphorated, phenol, free, phenylalanine, phosphatase, acid, prostatic, phospholipid, phosphorus, prealbumin, thyroxine-binding, proinsulin, prolactin (female), prolactin (male), proline, prostaglandins, prostate specific antigen, protein, total, protoporphyrin, pseudoglobulin I, pseudoglobulin II, purine, total, pyridoxine, pyrimidine nucleotide, pyruvic acid, CCL5 (RANTES), relaxin, retinol, retinol-binding protein, riboflavin, ribonucleic acid, secretin, serine, serotonin (5-hydroxytryptamine), silicon, sodium, solids, total, somatotropin (growth hormone), sphingomyelin, succinic acid, sugar, total, sulfates, inorganic, sulfur, total, taurine, testosterone (female), testosterone (male), triglycerides, triiodothyronine, tryptophan, tyrosine, urea, uric acid, water, miscellaneous trace components, and the like.

Among α-Globulins examples include, but are not limited to, α1-acid glycoprotein, α1-antichymotrypsin, α1-antitrypsin, α1B-glycoprotein, α1-fetoprotein, α1-microglobulin, α1T-glycoprotein, α2HS-glycoprotein, α2-macroglobulin, 3.1 S Leucine-rich α2-glycoprotein, 3.8 S histidine-rich α2-glycoprotein, 4 S α2, α1-glycoprotein, 8 S α3-glycoprotein, 9.5 S α1-glycoprotein (serum amyloid P protein), Corticosteroid-binding globulin, ceruloplasmin, GC globulin, haptoglobin (e.g., Type 1-1, Type 2-1, or Type 2-2), inter-α-trypsin inhibitor, pregnancy-associated α2-glycoprotein, serum cholinesterase, thyroxine-binding globulin, transcortin, vitamin D-binding protein, Zn-α2-glycoprotein, and the like. Among β-Globulins, examples include, but are not limited to, hemopexin, transferrin, β2-microglobulin, β2-glycoprotein I, β2-glycoprotein II, (C3 proactivator), β2-glycoprotein III, C-reactive protein, fibronectin, pregnancy-specific β1-glycoprotein, ovotransferrin, and the like. Among immunoglobulins examples include, but are not limited to, immunoglobulin G (e.g., IgG, $IgG_1$, $IgG_2$, $IgG_3$, $IgG_4$), immunoglobulin A (e.g., IgA, $IgA_1$, $IgA_2$), immunoglobulin M, immunoglobulin D, immunoglobulin E, κ Bence Jones protein, γ Bence Jones protein, J Chain, and the like.

Among apolipoproteins examples include, but are not limited to, apolipoprotein A-I (HDL), apolipoprotein A-II (HDL), apolipoprotein C-I (VLDL), apolipoprotein C-II, apolipoprotein C-III (VLDL), apolipoprotein E, and the like. Among γ-mobility (non-immunoglobulin) examples include, but are not limited to, 0.6 S γ2-globulin, 2 S γ2-globulin, basic Protein B2, post-γ-globulin (γ-trace), and the like. Among low-molecular weight proteins examples include, but are not limited to, lysozyme, basic protein B1, basic protein B2, 0.6 S γ2-globulin, 2 S γ 2-globulin, post γ-globulin, and the like.

Among complement components examples include, but are not limited to, C1 esterase inhibitor, C1q component, C1r component, C1s component, C2 component, C3 component, C3a component, C3b-inactivator, C4 binding protein, C4 component, C4a component, C4-binding protein, C5 component, C5a component, C6 component, C7 component, C8 component, C9 component, factor B, factor B (C3 proactivator), factor D, factor D (C3 proactivator convertase), factor H, factor H ($β_1H$), properdin, and the like. Among coagulation proteins examples include, but are not limited to, antithrombin III, prothrombin, antihemophilic factor (factor VIII), plasminogen, fibrin-stabilizing factor (factor XIII), fibrinogen, thrombin, and the like.

Among cell-Related Plasma Proteins examples include, but are not limited to, fibronectin, β-thromboglobulin, platelet factor-4, serum Basic Protease Inhibitor, and the like. Among amyloid proteins (Non-Immunoglobulin) examples include, but are not limited to, amyloid-Related apoprotein (apoSAA1), AA (FMF) (ASF), AA (TH) (AS), serum amyloid P component (9.5 S 7α1-glycoprotein), and the like. Among miscellaneous trace components examples include, but are not limited to, varcinoembryonic antigen, angiotensinogen, and the like.

In an embodiment, the sensor component 136 is configured to detect at least one of an emitted energy or a remitted energy associated with a real-time change in one or more parameters associated with at least one blood component within a biological subject.

In an embodiment, the sensor component 136 is configured to determine at least one characteristic (e.g., a spectral characteristic, a spectral signature, a physical quantity, a relative quantity, an environmental attribute, a physiologic characteristic, or the like) associated with a region within the biological subject. In an embodiment, the sensor component 136 is configured to determine at least one characteristic associated with an occlusion, a hematological abnormality, or a body fluid flow abnormality. In an embodiment, the sensor component 136 is configured to determine at least one characteristic associated with a portion of the tissue within the biological subject. In an embodiment, the sensor component 136 is configured to determine at least one characteristic associated with a biological fluid flow passage way.

In an embodiment, the sensor component 136 is configured to determine at least one characteristic associated with one or more blood components. In an embodiment, the sensor component 136 is configured to determine at least one characteristic associated with a tissue proximate the monitoring device 102. In an embodiment, the sensor component 136 is configured to determine a spatial dependence associated with the least one characteristic. In an embodiment, the sensor component 136 is configured to determine a temporal dependence associated with the least one characteristic. In an embodiment, the sensor component 136 is configured to concurrently or sequentially determine at least one spatial dependence associated with the least one characteristic and at least one temporal dependence associated with the least one characteristic.

In an embodiment, the sensor component 136 is configured to determine at least one spectral parameter associated with one or more imaging probes (e.g., chromophores, fluorescent agents, fluorescent marker, fluorophores, molecular imaging probes, quantum dots, radio-frequency identification transponders (RFIDs), x-ray contrast agents or the like). In an embodiment, the sensor component 136 is configured to determine at least one characteristic associated with one or more imaging probes attached, targeted to, conjugated, bound, or associated with at least one inflammation markers. See, e.g., the following documents (the contents of which are incorporated herein by reference): Jaffer et al., Arterioscler. Thromb. Vasc. Biol. 2002; 22; 1929-1935 (2002); Kalchenko et al., J. of Biomed. Opt. 11(5):50507 (2006)

In an embodiment, the one or more imaging probes include at least one carbocyanine dye label. In an embodiment, the sensor component 136 is configured to determine at least one characteristic associated with one or more imaging probes attached, targeted to, conjugated, bound, or associated with at least one blood components.

In an embodiment, the one or more imaging probes include at least one fluorescent agent. In an embodiment, the one or more imaging probes include at least one quantum dot. In an embodiment, the one or more imaging probes include at least one radio-frequency identification transponder. In an embodiment, the one or more imaging probes include at least one x-ray contrast agent. In an embodiment, the one or more imaging probes include at least one molecular imaging probe. A non-limiting approach includes systems, devices, methods, and compositions including, among other things, one or more imaging probes.

Among imaging probes examples include, but are not limited to, fluorescein (FITC), indocyanine green (ICG) and rhodamine B. Examples of other fluorescent dyes for use in fluorescence imaging include, but are not limited to, a number of red and near infrared emitting fluorophores (600-1200 nm) including cyanine dyes such as Cy5, Cy5.5, and Cy7 (Amersham Biosciences, Piscataway, N.J., USA) or a variety of Alexa Fluor dyes such as Alexa Fluor 633, Alexa Fluor 635, Alexa Fluor 647, Alexa Fluor 660, Alexa Fluor 680, Alexa Fluor 700, Alexa Fluor 750 (Molecular Probes-Invitrogen, Carlsbad, Calif., USA; see, also, U.S. Patent Pub. No. 2005/0171434 (published Aug. 4, 2005) (the contents of which are incorporated herein by reference), and the like.

Further examples of imaging probes include, but are not limited to, IRDye800, IRDye700, and IRDye680 (LI-COR, Lincoln, Neb., USA), NIR-1 and 1C5-OSu (Dejindo, Kumamotot, Japan), LaJolla Blue (Diatron, Miami, Fla., USA), FAR-Blue, FAR-Green One, and FAR-Green Two (Innosense, Giacosa, Italy), ADS 790-NS, ADS 821-NS (American Dye Source, Montreal, Calif.), NIAD-4 (ICx Technologies, Arlington, Va.), and the like. Further examples of fluorophores include BODIPY-FL, europium, green, yellow and red fluorescent proteins, luciferase, and the like. Quantum dots of various emission/excitation properties may be used as imaging probes. See, e.g., Jaiswal, et al. Nature Biotech. 21:47-51 (2003) (the contents of which are incorporated herein by reference).

Further examples of imaging probes include, but are not limited to, those including antibodies specific for leukocytes, anti-fibrin antibodies, monoclonal anti-diethylene triamine pentaacetic acid (DTPA), DTPA labeled with Technetium-99m ($^{99m}$TC), and the like.

In an embodiment, the sensor component 136 is configured to detect at least one of an emitted energy or a remitted energy associated with a biomarker. Among biomarker examples include, but are not limited to, one or more substances that are measurable indicators of a biological state and may be used as indicators of normal disease state, pathological disease state, and/or risk of progressing to a pathological disease state. In some instances, a biomarker can be a normal blood component that is increased or decreased in the pathological state. A biomarker can also be a substance that is not normally detected in the blood but is released into circulation as a result of the pathological state. In some instances, a biomarker can be used to predict the risk of developing a pathological state. For example, plasma measurement of lipoprotein-associated phospholipase A2 (Lp-PLA2) is approved by the U.S. Food & Drug Administration (FDA) for predicting the risk of first time stroke. In other instances, the biomarker can be used to diagnose an acute pathological state. For example, elevated plasma levels of S-100b, B-type neurotrophic growth factor (BNGF), von Willebrand factor (vWF), matrix metalloproteinase-9 (MMP-9), and monocyte chemoattractant protein-1 (MCP-1) are highly correlated with the diagnosis of stroke (see, e.g., Reynolds, et al., *Early biomarkers of stroke.* Clin. Chem. 49:1733-1739 (2003), which is incorporated herein by reference).

Among biomarkers associated with an occlusion (e.g., a thrombus, an embolus, or the like) or associated with pathological disease states examples include, but are not limited to, high-sensitivity C-reactive protein (hs-CRP), cardiac troponin T (cTnT), cardiac troponin I (cTnI), N-terminal-pro B-type natriuretic peptide (NT-proBNP), D-dimer, P-selectin, E-selectin, thrombin, interleukin-10, fibrin monomers, phospholipid microparticles, creatine kinase, interleukin-6, tumor necrosis factor-alpha, myeloperoxidase, intracellular adhesion molecule-1 (ICAM1), vascular adhesion molecule (VCAM), matrix metalloproteinase-9 (MMP9), ischemia modified albumin (IMA), free fatty acids, choline, soluble CD40 ligand, insulin-like growth factor, (see, e.g., Giannitsis, et al. *Risk stratification in pulmonary embolism based on biomarkers and echocardiography.* Circ. 112:1520-1521 (2005), Barnes, et al., *Novel biomarkers associated with deep venous throbosis: A comprehensive review.* Biomarker Insights 2:93-100 (2007); Kamphuisen, *Can anticoagulant treatment be tailored with biomarkers in patients with venous thromboembolism?* J. Throm. Haemost. 4:1206-1207 (2006); Rosalki, et al., *Cardiac biomarkers for detection of myocardial infarction: Perspectives from past to present. Clin. Chem.* 50:2205-2212 (2004); Apple, et al., *Future biomarkers for detection of ischemia and risk stratification in acute coronary syndrome*, Clin. Chem. 51:810-824 (2005), which are incorporated herein by reference).

In an embodiment, the at least one characteristic includes at least one of absorption coefficient information, extinction coefficient information, or scattering coefficient information associated with the at least one molecular probe. In an embodiment, the at least one characteristic includes spectral information indicative of a rate of change, an accumulation rate, an aggregation rate, or a rate of change associated with at least one physical parameter associated with an embolus.

In an embodiment, the at least one characteristic includes at least one of occlusion absorption coefficient information, occlusion extinction coefficient information, or occlusion scattering coefficient information. In an embodiment, the at least one characteristic includes at least one of thrombus absorption coefficient information, thrombus extinction coefficient information, or thrombus scattering coefficient information. In an embodiment, the at least one characteristic includes at least one of embolus spectral signature information, arterial embolus spectral signature information, thrombus spectral signature information, deep vein thrombus spectral signature, blood spectral signature information, or tissue spectral signature information. In an embodiment, the at least one characteristic includes at least one of having lymphatic system tissue spectral signature information or hair spectral signature information. In an embodiment, the at least one characteristic includes spectral signature information associated with an implant device.

For example, in an embodiment, the at least one characteristic includes implant device spectral signature information associates with at least one of a bio-implants, bioactive implants, breast implants, cochlear implants, dental implants, neural implants, orthopedic implants, ocular implants, prostheses, implantable electronic device, implantable medical devices, or the like. Further non-limiting examples of implant devices include replacements implants (e.g., joint replacements implants such, for example, elbows, hip (an example of which is shown on FIG. 1), knee, shoulder, wrists replacements implants, and the like), subcutaneous drug delivery devices (e.g., implantable pills, drug-eluting stents, and the like), shunts (e.g., cardiac shunts, lumbo-peritoneal shunts, cerebrospinal fluid (CSF) shunts, cerebral shunts, pulmonary shunts, portosystemic shunts, portacaval shunts, and the like), stents (e.g., coronary stents, peripheral vascular stents, prostatic stents, ureteral stents, vascular stents, and the like), biological fluid flow controlling implants, and the like. Further non-limiting examples of implant device include artificial hearts, artificial joints, artificial prosthetics, catheters, contact lens, mechanical heart valves, subcutaneous sensors, urinary catheters, vascular catheters, and the like.

In an embodiment, the at least one characteristic includes one or more indicators (e.g., biomarkers, blood components, or the like) of at least one of atrial fibrillation, cardiac ischemia, cardiomyopathy, cerebral ischemia, clotted arteriovenous fistula or shunt, deep vein thrombosis, limb ischemia, mesenteric ischemia, myocardial infarction, paradoxical embolism, pulmonary embolism, pulmonary ischemia, stroke, thromboembolic disease, thrombus, venous thrombosis, or the like.

In an embodiment, the at least one characteristic includes at least one of a transmittance, an interrogation energy frequency change, a frequency shift, an interrogation energy phase change, or a phase shift. In an embodiment, the at least one characteristic includes at least one of a fluorescence, and intrinsic fluorescence, a tissue fluorescence, or a naturally occurring fluorophore fluorescence. In an embodiment, the at least one characteristic includes at least one of an electrical conductivity, and electrical polarizability, or an electrical permittivity. In an embodiment, the at least one characteristic includes at least one of a thermal conductivity, a thermal diffusivity, a tissue temperature, or a regional temperature.

In an embodiment, the at least one characteristic includes at least one parameter associated with a doppler optical coherence tomograph. (See, e.g., Li et al., *Feasibility of Interstitial*

*Doppler Optical Coherence Tomography for In Vivo Detection of Microvascular Changes During Photodynamic Therapy,* Lasers in surgery and medicine 38(8):754-61. (2006), which is incorporated herein by reference; see, also U.S. Pat. No. 7,365,859 (issued Apr. 29, 2008), which is incorporated herein by reference).

The development of certain types of blood clots in veins is thought to involve an inflammatory process. (See, e.g., Myers et al., *P-Selectin and Leukocyte Microparticles are Associated with Venous Thrombogenesis,* J. Vasc. Surg. 38: 1075-1089 (2003), which is incorporated herein by reference). Higher levels of certain inflammation and blood-clotting markers may be associated with episodic treatment of HIV/AIDS with antiretroviral drugs and with a higher risk of death of HIV infected individuals from non-AIDS diseases. (See, e.g., Press Release, National Institute of Allergy and Infectious Diseases, *International HIV/AIDS Trial Finds Continuous Antiretroviral Therapy Superior to Episodic Therapy* (Jan. 18, 2006), which is incorporated herein by reference). In an embodiment, the sensor component 136 is configured to determine at least one characteristic associated with an inflammation marker.

In an embodiment, the at least one characteristic includes at least one of an inflammation indication parameter, an infection indication parameter, a diseased state indication parameter, or a diseased tissue indication parameter. In an embodiment, the at least one characteristic includes at least one parameter associated with a diseased state. Inflammation is a complex biological response to insults that can arise from, for example, chemical, traumatic, or infectious stimuli. It is a protective attempt by an organism to isolate and eradicate the injurious stimuli as well as to initiate the process of tissue repair. The events in the inflammatory response are initiated by a complex series of interactions involving inflammatory mediators, including those released by immune cells and other cells of the body. Histamines and eicosanoids such as prostaglandins and leukotrienes act on blood vessels at the site of infection to localize blood flow, concentrate plasma proteins, and increase capillary permeability. Chemotactic factors, including certain eicosanoids, complement, and especially cytokines known as chemokines, attract particular leukocytes to the site of infection. Other inflammatory mediators, including some released by the summoned leukocytes, function locally and systemically to promote the inflammatory response. Platelet activating factors and related mediators function in clotting, which aids in localization and can trap pathogens. Certain cytokines, interleukins and TNF, induce further trafficking and extravasation of immune cells, hematopoiesis, fever, and production of acute phase proteins. Once signaled, some cells and/or their products directly affect the offending pathogens, for example by inducing phagocytosis of bacteria or, as with interferon, providing antiviral effects by shutting down protein synthesis in the host cells.

Oxygen radicals, cytotoxic factors, and growth factors may also be released to fight pathogen infection or to facilitate tissue healing. This cascade of biochemical events propagates and matures the inflammatory response, involving the local vascular system, the immune system, and various cells within the injured tissue. Under normal circumstances, through a complex process of mediator-regulated pro-inflammatory and anti-inflammatory signals, the inflammatory response eventually resolves itself and subsides. For example, the transient and localized swelling associated with a cut is an example of an acute inflammatory response. However, in certain cases resolution does not occur as expected. Prolonged inflammation, known as chronic inflammation, leads to a progressive shift in the type of cells present at the site of inflammation and is characterized by simultaneous destruction and healing of the tissue from the inflammatory process, as directed by certain mediators. Rheumatoid arthritis is an example of a disease associated with persistent and chronic inflammation.

Non-limiting suitable techniques for optically measuring a diseased state may be found in, for example, U.S. Pat. No. 7,167,734 (issued Jan. 23, 2007), which is incorporated herein by reference. In an embodiment, the at least one characteristic includes at least one of an electromagnetic energy absorption parameter, an electromagnetic energy emission parameter, an electromagnetic energy scattering parameter, an electromagnetic energy reflectance parameter, or an electromagnetic energy depolarization parameter. In an embodiment, the at least one characteristic includes at least one of an absorption coefficient, an extinction coefficient, or a scattering coefficient.

In an embodiment, the at least one characteristic includes at least one parameter associated with an infection marker (e.g., an infectious agent marker), an inflammation marker, an infective stress marker, or a sepsis marker. Examples of infection makers, inflammation markers, and the like may be found in, for example, Imam et al., *Radiotracers for imaging of infection and inflammation—A Review,* World J. Nucl. Med. 40-55 (2006), which is incorporated herein by reference.

In an embodiment, the at least one characteristic includes at least one of a tissue water content, an oxy-hemoglobin concentration, a deoxyhemoglobin concentration, an oxygenated hemoglobin absorption parameter, a deoxygenated hemoglobin absorption parameter, a tissue light scattering parameter, a tissue light absorption parameter, a hematological parameter, or a pH level.

In an embodiment, the at least one characteristic includes at least one hematological parameter. Non-limiting examples of hematological parameters include an albumin level, a blood urea level, a blood glucose level, a globulin level, a hemoglobin level, erythrocyte count, a leukocyte count, and the like. In an embodiment, the infection marker includes at least one parameter associated with a red blood cell count, a leukocyte count, a myeloid count, an erythrocyte sedimentation rate, or a C-reactive protein level. In an embodiment, the at least one characteristic includes at least one parameter associated with a cytokine plasma level or an acute phase protein plasma level. In an embodiment, the at least one characteristic includes at least one parameter associated with a leukocyte level.

With continued reference to FIG. 2, the system 100 can include, but is not limited to, one or more controllers 148 such as a processor (e.g., a microprocessor) 150, a central processing unit (CPU) 152, a digital signal processor (DSP) 154, an application-specific integrated circuit (ASIC) 156, a field programmable gate array (FPGA) 158, and the like, and any combinations thereof, and may include discrete digital or analog circuit elements or electronics, or combinations thereof. The system 100 can include, but is not limited to, one or more field programmable gate arrays having a plurality of programmable logic components. The system 100 can include, but is not limited to, one or more an application specific integrated circuits having a plurality of predefined logic components.

In an embodiment, the monitoring device 102 can be, for example, wirelessly coupled to a controller 148 that communicates with the monitoring device 102 via wireless communication. Examples of wireless communication include for example, but not limited to, optical connections, ultraviolet connections, infrared, BLUETOOTH®, Internet connections, radio, network connections, and the like. The system 100 can include, but is not limited to, means for generating a response based on a comparison, of a detected at least one of an emitted interrogation energy or a remitted interrogation energy to at least one heuristically determined parameter, including one or more controllers 148.

In an embodiment, at least one controller 148 is configured to control at least one parameter associated with the delivery of an interrogation energy. In an embodiment, at least one controller 148 is configured to control at least one of a duration time, a delivery location, or a spatial-pattern configuration associated with the delivery of the interrogation energy. In an embodiment, the at least one controller 148 is configured to control at least one of an excitation intensity, an excitation frequency, an excitation pulse frequency, an excitation pulse ratio, an excitation pulse intensity, an excitation pulse duration time, an excitation pulse repetition rate, an ON-rate, or an OFF-rate. In an embodiment, at least one controller 148 operably coupled to the energy emitter component 104. In an embodiment, at least one controller 148 is operably coupled to the sensor component 136 and configured to process an output associated with one or more sensors 138. In an embodiment, the system 100 includes one or more controllers 148 configured to concurrently or sequentially operate multiple energy emitters 106. In an embodiment, the system 100 includes one or more controllers 148 configured to concurrently or sequentially operate multiple sensors 138.

The system 100 can include, but is not limited to, one or more memories 160 that, for example, store instructions or data, for example, volatile memory (e.g., Random Access Memory (RAM) 162, Dynamic Random Access Memory (DRAM), and the like), non-volatile memory (e.g., Read-Only Memory (ROM) 164, Electrically Erasable Programmable Read-Only Memory (EEPROM), Compact Disc Read-Only Memory (CD-ROM), and the like), persistent memory, and the like. Further non-limiting examples of one or more memories 160 include Erasable Programmable Read-Only Memory (EPROM), flash memory, and the like. The one or more memories can be coupled to, for example, one or more controllers 148 by one or more instruction, data, or power buses 165.

The system 100 can include, but is not limited to, one or more databases 166. In an embodiment, a database 166 can include, but is not limited to, at least one of stored reference data such as characteristic embolus spectral signature data representative of the presence of at least a partial occlusion in a blood vessel, characteristic arterial embolus spectral signature data representative of the presence of at least a partial occlusion in an artery, characteristic thrombus spectral signature data representative of at least a partial blood clot formation in a blood vessel, characteristic deep vein thrombus spectral signature data representative of at least a partial blood clot formation in a deep vein, characteristic blood component signature data, or characteristic tissue signature data.

In an embodiment, a database 166 can include, but is not limited to, information indicative of one or more spectral events associated with transmitted optical energy or a remitted optical energy from a biological tissue. In an embodiment, a database 166 can include, but is not limited to, at least one of blood spectral information, fat spectral information, muscle spectral information, or bone spectral information. In an embodiment, a database 166 can include, but is not limited to, modeled tissue (e.g., blood, bone, muscle, tendons, organs, fluid-filled cysts, ventricles, or the like) spectral information. In an embodiment, a database 166 can include, but is not limited to, at least one of modeled blood spectral information, modeled fat spectral information, modeled muscle spectral information, or modeled bone spectral information.

In an embodiment, a database 166 can include, but is not limited to, at least one of modeled embolus spectral signature data, modeled arterial embolus spectral signature data, modeled thrombus spectral signature data, modeled deep vein thrombus spectral signature data, modeled blood component signature data, or modeled tissue signature data.

In an embodiment, a database 166 can include, but is not limited to, at least one of inflammation indication parameter data, infection indication parameter data, diseased tissue indication parameter data, or the like. In an embodiment, a database 166 can include, but is not limited to, at least one of absorption coefficient data, extinction coefficient data, scattering coefficient data, or the like. In an embodiment, a database 166 can include, but is not limited to, stored reference data such as blood vessel occlusion data. In an embodiment, a database 166 can include, but is not limited to, stored reference data such as characteristic spectral signature data.

In an embodiment, a database 166 can include, but is not limited to, at least one of stored reference data such as infection marker data, inflammation marker data, infective stress marker data, sepsis marker data, or the like. In an embodiment, a database 166 can include, but is not limited to, information associated with a disease state of a biological subject. In an embodiment, a database 166 can include, but is not limited to, measurement data.

In an embodiment, the system 100 is configured to compare an input associated with a biological subject to a database 166 of stored reference values, and to generate a response based in part on the comparison. In an embodiment, the system 100 is configured to compare an output of one or more of the plurality of logic components and to determine at least one parameter associated with a cluster centroid deviation derived from the comparison. In an embodiment, the system 100 is configured to compare generated first response to the blood vessel occlusion information, and to generate a second response based on the comparison. In an embodiment, the system 100 is configured to compare a measurand associated with the biological subject to a threshold value associated with the tissue spectral model and to generate a response based on the comparison. In an embodiment, the system 100 is configured to generate the response based on the comparison of a measurand that modulates with a detected heart beat of the biological subject to a target value associated with the tissue spectral model. In an embodiment, the system 100 is configured to compare the measurand associated with the biological subject to the threshold value associated with the tissue spectral model and to generate a real-time estimation of the formation of an obstruction of a flow in a blood vessel based on the comparison.

In an embodiment, the system 100 is configured to compare an input associated with at least one characteristic associated with, for example, a tissue proximate an monitoring device 102 to a database 166 of stored reference values, and to generate a response based in part on the comparison.

The system 100 can include, but is not limited to, one or more data structures (e.g., physical data structures) 168. In an embodiment, a data structure 168 can include, but is not limited to, blood vessel occlusion information. In an embodiment, the blood vessel occlusion information includes one or more heuristically determined parameters associated with at least one in vivo or in vitro determined metric. Examples of heuristics include, a heuristic protocol, heuristic algorithm, threshold information, a threshold level, a target parameter, or the like. The system 100 can include, but is not limited to, a means for generating one or more heuristically determined parameters associated with at least one in vivo or in vitro determined metric including one or more data structures 168.

The system 100 can include, but is not limited to, a means for generating a response based on a comparison, of a detected at least one of an emitted interrogation energy or a remitted interrogation energy to at least one heuristically determined parameter, including one or more data structures 168.

As shown in Examples 1-8, spectral information associate with for example, but not limited to, one or more blood components can be determined by one or more in vivo or in vitro technologies or methodologies.

In an embodiment, a data structure 168 can include, but is not limited to, one or more heuristics. In an embodiment, the one or more heuristics include a heuristic for determining a rate of change associated with at least one physical parameter associated with an embolus. In an embodiment, the one or more heuristics include a heuristic for determining the presence of an occlusion. In an embodiment, the one or more heuristics include a heuristic for determining at least one dimension of an occlusion. In an embodiment, the one or more heuristics include a heuristic for determining a location of an occlusion. In an embodiment, the one or more heuristics include a heuristic for determining a rate of formation of an occlusion. In an embodiment, the one or more heuristics include a heuristic for determining an occlusion aggregation rate. In an embodiment, the one or more heuristics include a heuristic for determining a type of occlusion. In an embodiment, the one or more heuristics include a heuristic for generating at least one initial parameter. In an embodiment, the one or more heuristics include a heuristic for forming an initial parameter set from one or more initial parameters. In an embodiment, the one or more heuristics include a heuristic for generating at least one initial parameter, and for forming an initial parameter set from the at least one initial parameter. In an embodiment, the one or more heuristics include at least one pattern classification and regression protocol.

In an embodiment, a data structure 168 can include, but is not limited to, characteristic spectral signature information. In an embodiment, a data structure 168 can include, but is not limited to, at least one of characteristic embolus spectral signature information representative of the presence of at least a partial occlusion in a blood vessel, characteristic arterial embolus spectral signature information representative of the presence of at least a partial occlusion in an artery, characteristic thrombus spectral signature information representative of at least a partial blood clot formation in a blood vessel, characteristic deep vein thrombus spectral signature information representative of at least a partial blood clot formation in a deep vein, characteristic blood component signature information, or characteristic tissue signature information.

In an embodiment, the characteristic embolus spectral signature information includes at least one of a characteristic embolus absorption value indicative of an embolus absorption coefficient, a characteristic embolus extinction value indicative of an embolus extinction coefficient, or a characteristic embolus scattering value indicative of an embolus scattering coefficient. In an embodiment, the characteristic embolus spectral signature information includes at least one of characteristic embolus absorption coefficient data, characteristic embolus extinction coefficient data, or characteristic embolus scattering coefficient data.

In an embodiment, the characteristic arterial embolus spectral signature information includes at least one of a characteristic arterial embolus absorption value indicative of an arterial embolus absorption coefficient, a characteristic arterial embolus extinction value indicative of an arterial embolus extinction coefficient, or a characteristic arterial embolus scattering value indicative of an arterial embolus scattering coefficient. In an embodiment, the characteristic arterial embolus spectral signature information includes at least one of characteristic arterial embolus absorption coefficient data, characteristic arterial embolus extinction coefficient data, or characteristic arterial embolus scattering coefficient data. In an embodiment, the characteristic arterial embolus spectral signature information includes at least one spectral parameter associated with a peripheral artery occlusion.

In an embodiment, the characteristic thrombus spectral signature information includes at least one of a characteristic thrombus absorption value indicative of a thrombus absorption coefficient, a characteristic thrombus extinction value indicative of a thrombus extinction coefficient, or a characteristic thrombus scattering value indicative of a thrombus scattering coefficient. In an embodiment, the characteristic thrombus spectral signature information includes at least one of characteristic thrombus absorption coefficient data, characteristic thrombus extinction coefficient data, or characteristic thrombus scattering coefficient data.

In an embodiment, the characteristic deep vein thrombus spectral signature information includes at least one of a characteristic deep vein thrombus absorption value indicative of a deep vein thrombus absorption coefficient, a characteristic deep vein thrombus extinction value indicative of a deep vein thrombus extinction coefficient, or a characteristic deep vein thrombus scattering value indicative of a deep vein thrombus scattering coefficient. In an embodiment, the characteristic deep vein thrombus spectral signature information includes at least one of characteristic deep vein thrombus absorption coefficient data, characteristic deep vein thrombus extinction coefficient data, or characteristic deep vein thrombus scattering coefficient data.

In an embodiment, a data structure 168 can include, but is not limited to, at least one of information associated with at least one parameter associated with a tissue water content, an oxy-hemoglobin concentration, a deoxyhemoglobin concentration, an oxygenated hemoglobin absorption parameter, a deoxygenated hemoglobin absorption parameter, a tissue light scattering parameter, a tissue light absorption parameter, a hematological parameter, a pH level, or the like. The system 100 can include, but is not limited to, at least one of inflammation indication parameter data, infection indication parameter data, diseased tissue indication parameter data, or the like configured as a data structure 168. In an embodiment, a data structure 168 can include, but is not limited to, information associated with least one parameter associated with a cytokine plasma concentration or an acute phase protein plasma concentration. In an embodiment, a data structure 168 can include, but is not limited to, information associated with a disease state of a biological subject. In an embodiment, a data structure 168 can include, but is not limited to, measurement data.

In an embodiment, the system 100 is configured to compare an input associated with at least one characteristic associated with a tissue proximate an monitoring device 102 to a data structure 168 including reference values, and to generate a response based in part on the comparison. In an embodiment, the system 100 is configured to compare an input associated with a detected embolic or thrombotic event and to generate a response based on the comparison. In an embodiment, the system 100 is configured to compare an input associated with a detected embolic or thrombotic event to a data structure 168 including reference values, and to generate a response based in part on the comparison.

In an embodiment, a controller 148 is configured to compare a generated first response to the blood vessel occlusion information, and to generate a second response based on the comparison. In an embodiment, the controller 148 includes a processor configured to execute instructions, and a memory 160 that stores instructions configured to cause the processor to generate a second response from information encoded in the data structure 168. The second response can include, but is not limited to, at lease one of a response signal, an absorption parameter, an extinction parameter, a scattering parameter, a comparison code, a comparison plot, a diagnostic code, a treatment code, an alarm response, or a test code based on the comparison of a detected optical energy absorption profile to characteristic spectral signature information. In an embodiment, the response includes al least one of a display, a visual representation (e.g., a visual depiction representative of the detected (e.g., assessed, calculated, evaluated, determined, gauged, measured, monitored, quantified, resolved, sensed, or the like) information) a visual display, a visual display of at least one spectral parameter, and the like. In an embodiment, the response includes a visual representation indicative of a parameter associated with an embolus, thrombus, or a deep vein thrombus present in a region of a tissue proximate the optical energy sensor component. In an embodiment, the response includes a generating a representation (e.g., depiction, rendering, modeling, or the like) of at least one physical parameter associated with an embolus, a thrombus, or a deep vein thrombus. In an embodiment, the response includes a generating a visual representation of at least one physical parameter associated with an embolus, a thrombus, or a deep vein thrombus. In an embodiment, the response includes generating a visual representation of at least one physical parameter indicative of at least one dimension of an embolus, a thrombus, or a deep vein thrombus. In an embodiment, the response includes a visual representation of an embolus, a thrombus, or a deep vein thrombus. In an embodiment, the response includes generating a visual representation of at least one spectral parameter associated with an embolus, a thrombus, or a deep vein thrombus. In an embodiment, the response includes generating a visual representation of at least one of blood spectral information, fat spectral information, muscle spectral information, or bone spectral information. In an embodiment, the response includes al least one of a visual representation, an audio representation (e.g., an alarm, an audio waveform representation of an occlusion, or the like), or a tactile representation (e.g., a tactile diagram, a tactile display, a tactile graph, a tactile interactive depiction, a tactile model (e.g., a multidimensional model of occlusion, or the like), a tactile pattern (e.g., a refreshable Braille display), a tactile-audio display, a tactile-audio graph, or the like).

In an embodiment, a controller 148 is configured to compare a measurand associated with the biological subject to a threshold value associated with a tissue spectral model and to generate a response based on the comparison. In an embodiment, a controller 148 is configured to generate the response based on the comparison of a measurand that modulates with a detected heart beat of the biological subject to a target value associated with a tissue spectral model. In an embodiment, a controller 148 is configured to compare the measurand associated with the biological subject to the threshold value associated with a tissue spectral model and to generate a real-time estimation of the formation of an obstruction of a flow in a blood vessel based on the comparison. In an embodiment, a controller 148 is configured to concurrently or sequentially operate multiple optical energy emitters 110. In an embodiment, a controller 148 is configured to compare an input associated with at least one characteristic associated with, for example, a tissue proximate an monitoring device 102 to a database 166 of stored reference values, and to generate a response based in part on the comparison.

The system 100 can include, but is not limited to, one or more computer-readable media drives 170, interface sockets, Universal Serial Bus (USB) ports, memory card slots, and the like, and one or more input/output components 172 such as, for example, a graphical user interface 172a, a display, a keyboard 172b, a keypad, a trackball, a joystick, a touchscreen, a mouse, a switch, a dial, and the like, and any other peripheral device. In an embodiment, the system 100 can include, but is not limited to, one or more user input/output components 172 that operably-couple to at least one controller 148 to control (electrical, electromechanical, software-implemented, firmware-implemented, or other control, or combinations thereof) at least one parameter associated with the energy delivery associated with the energy emitter component 104.

The computer-readable media drive 170 or memory slot may be configured to accept signal-bearing medium (e.g., computer-readable memory media, computer-readable recording media, and the like). In an embodiment, a program for causing the system 100 to execute any of the disclosed methods can be stored on, for example, a computer-readable recording medium, a signal-bearing medium, and the like. Examples of signal-bearing media include, but are not limited to, a recordable type medium such as a magnetic tape, floppy disk, a hard disk drive, a Compact Disc (CD), a Digital Video Disk (DVD), Blu-Ray Disc, a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.). Further non-limiting examples of signal-bearing media include, but are not limited to, DVD-ROM, DVD-RAM, DVD+RW, DVD-RW, DVD-R, DVD+R, CD-ROM, Super Audio CD, CD-R, CD+R, CD+RW, CD-RW, Video Compact Discs, Super Video Discs, flash memory, magnetic tape, magneto-optic disk, MINIDISC, non-volatile memory card, EEPROM, optical disk, optical storage, RAM, ROM, system memory, web server, and the like. In an embodiment, the system 100 can include, but is not limited to, signal-bearing media in the form of one or more logic devices (e.g., programmable logic devices, complex programmable logic device, field-programmable gate arrays, application specific integrated circuits, and the like) comprising, for example, one or more look-up tables.

In an embodiment, the system 100 is configured to initiate one or more treatment protocols. In an embodiment, the system 100 is configured to initiate at least one treatment regiment based on a detected spectral event. In an embodiment, the system 100 is configured to initiate at least one treatment regiment based on a detected embolic or thrombotic event. In an embodiment, the system 100 is configured to initiate at least one treatment regiment based on a detected ischemia. In an embodiment, the system 100 is configured to initiate at least one treatment regiment based on a detected myocardial infarction. Among treatments for thrombi, examples include, but are not limited to, administering to the biological subject anticoagulants such as, for example, heparin, low-molecular weight heparin sold as Dalteparin (Fragmin®), Enoxaparin (Lovenox®), and Tinzaparin (Innohep®), and warfarin (Coumadin®). Among treatments for emboli, examples include, but are not limited to, administering to the biological subject clot-dissolving agents (thrombolytics) and/or clot preventing agents (anticoagulants). Examples of thrombolytics include streptokinase, urokinase, and recombinant tissue plasminogen activator (tPA; Alteplase®). Heparin and warfarin are used as anticoagulants. Fondaparinux (Arixtra®), an inhibitor of activated Factor X (Xa), may also be used in combination with warfarin. Among treatments for pulmonary emboli, examples include, but are not limited to, administering to the biological subject thrombolytic drugs streptokinase, urokinase or tissue plasminogen activator t-PA. Pulmonary emboli are also treated with vein filters to prevent clots from being carried into the pulmonary artery. Anticoagulation therapy may be used for prophylaxis of pulmonary embolism. Among treatments for deep vein thrombi, examples include, but are not limited to, anticoagulation therapy, unless otherwise contraindicated. Anticoagulation therapy may be provided as a two step process. Warfarin is begun immediately after diagnosis but may take a week or more to appropriately thin the blood. As such, low molecular weight heparin (e.g., enoxaparin) is administered simultaneously. Enoxaparin thins the blood via a different mechanism and is used as a bridge therapy until the warfarin has reached its therapeutic level. Subcutaneous injection of enoxaparin can be given on an outpatient basis or self-administered and may be used for 7 to 14 days. Warfarin may be continued for three to 12 months. Subjects with a propensity to form blood clots (thrombophilias) may require lifetime anticoagulation therapy. Warfarin is indicated for prophylaxis and/or treatment of venous thrombosis and its extension, and pulmonary embolism; prophylaxis and/or treatment of thromboembolic complication associated with atrial fibrillation and/or cardiac valve replacement; and to reduce the risk of death, recurrent myocardial infarction, and thromboembolic event such as stroke or systemic embolization after myocardial infarction. See, e.g., Ramzi & Leeper. *DVT and pulmonary embolism. Part II. Treatment and prevention.* Am. Fam. Physician 69:2829-2836 (2004).

Causes of acute limb ischemia include an acute arterial occlusion of the lower extremities. Occlusion may be caused by an embolus, thrombosis, or a combination thereof. Non-atherosclerotic causes of acute limb ischemia include arterial trauma, aortic/arterial dissection, arteritis with thrombosis, spontaneous thrombosis associated with a hypercoagulable state, popliteal cyst with thrombosis, popliteal entrapment with thrombosis, vasospasm with thrombosis. Causes of acute limb ischemia in atherosclerotic patients includes thrombosis of an atherosclerotic stenosed artery, thrombosis of an arterial bypass graft, embolism from heart, aneurysm, plaque, or critical stenoisis upstream, and thrombosed aneurysm. If there are no associated contraindications (e.g., acute aortic dissection or multiple trauma, particularly severe head injury), treatments for limb ischemia can include, but are not limited to, administration of an intravenous bolus of heparin to limit propagation of the thrombus and to protect collateral circulation. Thrombolytic agents may also be considered. Under circumstances in which the limb viability is threatened by the ischemia, surgery is the preferential treatment choice. If damage is irreversible, amputation may be necessary. See, e.g., Callum & Bradbury *ABC of arterial and venous disease. Acute limb ischemia.* BMJ 320:764-767 (2000). Among treatments for ischemic stroke, examples include, but are not limited to, prompt restoration of blood flow. If the diagnosis of stroke is made within approximately 3 hours of the onset of symptoms, than the use of a thrombolytic agent such as, for example, tissue plasminogen activator (t-PA) may be indicated. t-PA and other thrombolytic agents are contraindicated in individuals experiencing stroke associated with hemorrhaging. Aspirin or aspirin combined with another antiplatelet drug may be given along with drugs to control blood sugar, fever and/or seizures, as warranted. Following a stroke, aspirin, antiplatelet drugs and/or anticoagulants may be pre-scribed. In addition to drug therapy, it is important to control risk factors for stroke such as, for example, high blood pressure, atrial fibrillation, high cholesterol and/or diabetes. Among treatments for myocardial infarction, examples include, but are not limited to, thrombolytic therapy. This treatment can be useful when administered within the first approximate 12 hours of symptom onset. Heparin (or other anticoagulants) may be used as an adjunct to thrombolytic therapy. Aspirin has been shown to decrease mortality and re-infarction rates after myocardial infarction. Clopidogrel (Plavix®) can be used as a substitute by those resistant or allergic to aspirin. Platelet glycoprotein (GP) IIb/IIIa-receptor antagonists (eptifibatide (Integrilin®), tirofiban (Aggrastat®), or abciximab (ReoPro®) as well as acetylsalicylic acid and unfractionated heparin (UFH) can be administered to patients with continuing ischemia. Nitrates may be used for symptom relief but have no effect on rates of mortality. Beta blockers and ACE inhibitors may also be of used for preventing reoccurrence. See, e.g. http://emedicine.medscape.com/article/155919-treatment; see also http:/www.clevelandclinicmeded.com/medicalpubs/diseasemanagement/cardiology/acute-myocardial-infarction/; Bitigen, et al., Exp. Clin. Cardiol. 12:203-205 (2007).

Many of the disclosed embodiments may be electrical, electromechanical, software-implemented, firmware-implemented, or other otherwise implemented, or combinations thereof. Many of the disclosed embodiments may be software or otherwise in memory, such as one or more executable instruction sequences or supplemental information as described herein. For example, in an embodiment, the monitoring device 102 can include, but is not limited to, one or more processors configured to perform a comparison of the at least one characteristic associated with the tissue proximate the monitoring device 102 to stored reference data, and to generate a response based at least in part on the comparison. In an embodiment, the generated response includes at least one of a response signal, a change to an energy delivery parameter, a change in an excitation intensity, a change in an excitation frequency, a change in an excitation pulse frequency, a change in an excitation pulse ratio, a change in an excitation pulse intensity, a change in an excitation pulse duration time, a change in an excitation pulse repetition rate, or a change in an energy delivery regiment parameter. In an embodiment, the controller 148 is operably coupled to the sensor component 136, and is configured to determine the at least one characteristic associated with the tissue proximate the monitoring device 102.

In an embodiment, the controller 148 is configured to perform a comparison of the at least one characteristic associated with the tissue proximate the monitoring device 102 to stored reference data, and to generate a response based at least in part on the comparison. The monitoring device 102 can include, but is not limited to, a tissue characteristic sensor component. In an embodiment, the controller 148 is configured to perform a comparison of the at least one characteristic associated with the tissue proximate the monitoring device 102 to stored reference data, and to generate a response based at least in part on the comparison.

The monitoring device 102 can include, but is not limited to, sensor component 136 configured to determine at least one characteristic associated with a biological subject. For example, a characteristics such as, for example the detection of one or more blood components may be use to assess blood flow, a cell metabolic state (e.g., anaerobic metabolism, and the like), the presence of an occlusion, the presence of an embolus, the presence of a thrombus, the presence of an infection agent, a disease state, an occurrence of an embolic even, an occurrence of a thrombotic event, or the like. In an embodiment, the monitoring device 102 can include, but is not limited to, a sensor component 136 configured to determine at least one of a physiological characteristic of a biological subject, or a characteristic associated with a tissue proximate the monitoring device 102.

Among characteristics associated with the biological subject examples include, but are not limited to, at least one of a temperature, a regional or local temperature, a pH, an impedance, a density, a sodium ion level, a calcium ion level, a potassium ion level, a glucose level, a cholesterol level, a triglyceride level, a hormone level, a blood oxygen level, a pulse rate, a blood pressure, a respiratory rate, a vital statistic, and the like. In an embodiment, the physiological characteristic includes at least one of a temperature, a pH, an impedance, a density, a sodium ion level, a calcium ion level, a potassium ion level, a glucose level, a cholesterol level, a triglyceride level, a hormone level, a blood oxygen level, a pulse rate, a blood pressure, or a respiratory rate.

In an embodiment, the characteristic includes at least one hematological parameter. In an embodiment, the hematological parameter is associated with a hematological abnormality. In an embodiment, the physiological characteristic includes one or more parameters associated with at least one of neutropenia, neutrophilia, thrombocytopenia, disseminated intravascular coagulation, bacteremia, or viremia.

In an embodiment, the characteristic includes at least one of an infection marker, an inflammation marker, an infective stress marker, or a sepsis marker. In an embodiment, the infection marker includes at least one of a red blood cell count, a leukocyte count, a myeloid count, an erythrocyte sedimentation rate, or a C-reactive protein level. In an embodiment, the physiological characteristic includes at least one of a cytokine plasma concentration or an acute phase protein plasma concentration.

The monitoring device 102 can include, but is not limited to, circuitry for performing a comparison of the determined at least one characteristic associated with the tissue proximate the monitoring device 102 to stored reference data following delivery of an interrogation stimulus by the energy emitting component 104. The monitoring device 102 can include, but is not limited to, circuitry for generating a response based at least in part on the comparison.

The monitoring device 102 can include, but is not limited to, one or more processors configured to perform a comparison of the at least one characteristic to stored reference data following delivery of an energy stimulus (e.g., interrogation energy stimulus), and to generate a response based at least in part on the comparison.

In an embodiment, the generated response can include, but is not limited to, at least one of a response signal, a control signal, a change to an interrogation energy parameter (e.g., an electrical stimulus parameter, an electromagnetic stimulus parameter, an ultrasonic stimulus parameter, or a thermal stimulus parameter), a change in an excitation intensity, a change in an excitation frequency, a change in an excitation pulse frequency, a change in an excitation pulse ratio, a change in an excitation pulse intensity, a change in an excitation pulse duration time, a change in an excitation pulse repetition rate, a change to a interrogation energy spatial pattern parameter or a change in an interrogation energy delivery regiment parameter (e.g., an electrical stimulus delivery regiment parameter, an electromagnetic stimulus delivery regiment parameter, an ultrasonic stimulus delivery regiment parameter, or a thermal stimulus delivery regiment parameter).

In an embodiment, the system 100 is configured to monitor one of more conditions associated with a predisposition to a thrombus formation. Examples of conditions predispose to thrombus formation include, abnormal blood constituents; abnormalities in platelet function, coagulation, fibrinolysis, and metabolic or hormonal factors; abnormalities of haemorheology; atherosclerosis; endothelial dysfunction, inflammation, turbulence at bifurcations and stenotic regions, and the like.

Examples of diseases associated with infarctions include, but are not limited to, antiphospholipid syndrome, cerebrovascular accident, giant-cell arteritis (GCA), hernia, myocardial infarction (heart attack), peripheral artery occlusive disease, pulmonary embolism, sepsis, and volvulus. In an embodiment, the system 100 is configured to monitor one of more conditions associated with an infarction.

In an embodiment, the system 100 is configured to monitor one of more conditions associated with a stroke. For example, cerebral embolism is one of the major causes of stroke. In an embodiment, the system 100 is configured to detect emboli in the intracranial arteries.

In an embodiment, the system 100 is configured to monitor one of more conditions associated with a thrombosis. Thrombus formation may result from an injury to the vessel's wall (such as by trauma, infection, or turbulent flow at bifurcations); by the slowing or stagnation of blood flow past the point of injury (which may occur after long periods of sedentary behavior—for example, sitting on a long airplane flight); by a blood state of hypercoagulability (caused for example, by genetic deficiencies or autoimmune disorders).

Examples of conditions associated with thrombosis include, but are not limited to, arterial thrombosis, budd-chiari syndrome, cerebral venous sinus thrombosis, chronic coronary ischemia, coronary thrombosis, deep vein thrombosis, jugular vein thrombosis, mural thrombosis, myocardial infarction, paget-schroetter disease, peripheral vascular disease, portal vein thrombosis, pulmonary embolism, renal vein thrombosis, retinal vein occlusion, stroke, thrombophlebitis, venous thrombosis, and the like.

In an embodiment, the system 100 is configured to monitor one of more conditions associated with an embolism. Examples of conditions associated with embolisms include, but are not limited to, amniotic fluid embolisms (generally associated with amniotic fluid, foetal cells, hair, or other debris that enters the mother's bloodstream via the placental bed of the uterus), arterial embolisms, cerebral embolisms, fat embolisms (generally associated with fat droplets), foreign body embolisms (generally associated with foreign materials such as talc and other small objects), gas embolisms (generally associated with gas bubbles), pulmonary embolisms, septic embolisms (generally associated with pus-containing bacteria), thromboembolisms (generally associated with a thrombus or blood clot), tissue embolisms (generally associated with small fragments of tissue, venus embolisms, and the like. Cancer is also associated with the risk of blood clots. For example, cancer patient may have hypercoagulable blood resulting from multiple disturbances in their metabolism and circulation.

In an embodiment, the system 100 is configured to monitor a user associated with a thrombolytic indication. Examples of thrombolytic indications include acute myocardial infarction, acute ischemic stroke, acute pulmonary embolism, acute deep venous thrombosis, a clotted arteriovenous fistula or shunt, or the like.

It may be necessary to have technologies and methodologies configure to monitor, for example, a condition associated with an occlusion within a body fluid vessel over at least a first interval of time. It may be necessary to have technologies and methodologies configure to monitor, for example, a condition associated with an occlusion within a body fluid vessel, in various environments (e.g., an operation room, while engaged in an activity, while operating heavy equipment, or the like) or under various conditions (e.g., outpatient monitoring, or the like). A non-limiting example includes systems, devices, and methods including a body structure configured for wear by a user. A non-limiting example includes systems, devices, and methods including a body structure configured to monitor a user for an extended period of time. A non-limiting example includes systems, devices, and methods including a body structure configured for wear by users and configured to monitor users prior, during or after invasive procedures. A non-limiting example includes systems, devices, and methods including a body structure configured for prolong wear by a user. In an embodiment, at least one of the monitoring device 102, the energy emitter component 104, or the sensor component 136 is configured for removable attachment to a biological surface (e.g., any tissue surface, skin, an outer surface of an extremity (e.g., an arm, leg, hand, foot, ankle, shoulder, knee, hip, hand, or the like), an outer surface of the head, neck, face, or ear, or an orifice, or the like. In an embodiment, at least one of the monitoring device 102, the energy emitter component 104, or the sensor component 136 is configured to be pressed against a surface of the biological subject. In an embodiment, at least one of the monitoring device 102, the energy emitter component 104, or the sensor component 136 is configured to conform and removably-fasten to, for example, an extremity, a surface, a portion, or an orifice of the biological subject. In an embodiment, at least one of the monitoring device 102, the energy emitter component 104, or the sensor component 136 can be held in place using one or more fastening components including for example, but not limited to, elastic bands, hook and loop fasteners, clip-type devices, buckles, straps, snaps, clamps, or the like. In an embodiment, at least one of the monitoring device 102, the energy emitter component 104, or the sensor component 136 can be attached to the biological subject using, for example, adhesive materials, or any other technologies that affixes at least one of the monitoring device 102, the energy emitter component, or the sensor component 136 in place. In an embodiment, at least one of the monitoring device 102, the energy emitter component 104, or the sensor component 136 includes a flexible substrate capable of conforming to a variety of shapes or contours associated with an outer surface of the biological subject. In an embodiment, at least one of the monitoring device 102, the energy emitter component 104, or the sensor component 136 is readily conformable to a biological subject's anatomical contours.

The system 100 includes, but is not limited to, a physical coupling element configured to removably-attach at least one of the energy emitter component 104 or the sensor component 136 to a biological surface of the biological subject. In an embodiment, the system 100 includes, but is not limited to, a physical coupling element configured to removably-attach at least one of the optical energy emitter component 104a or the optical energy sensor component 136a to a biological surface of the biological subject. In an embodiment, at least one of the monitoring device 102, the energy emitter component 104, or the sensor component 136 is configured for removable attachment to an outer portion of a biological subject. In an embodiment, at least one of the monitoring device 102, the optical energy emitter component 104a, or the optical energy sensor component 136a is configured for removable attachment to an outer portion of a biological subject.

Figure 3:
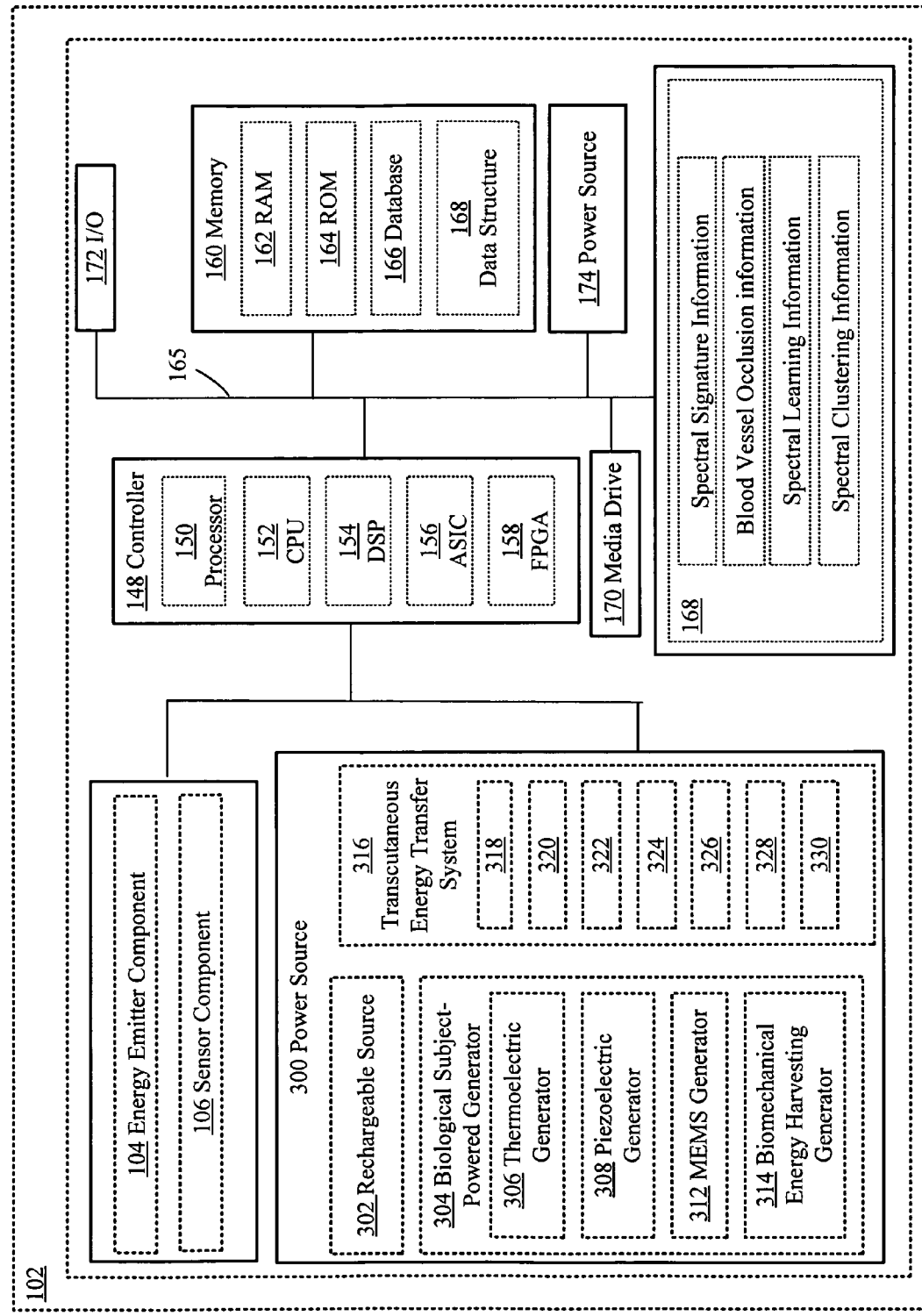
FIG. 3 is a schematic diagram of a system including one or more monitoring devices according to one illustrated embodiment.

Referring to FIG. 3, the monitoring device 102 can include, but is not limited to, one or more power sources 300. In an embodiment, the power source 300 is electromagnetically, magnetically, ultrasonically, optically, inductively, electrically, or capacitively-coupleable to at least one of the energy emitter component 104 or the sensor component 136. In an embodiment, the power source 300 is carried by the monitoring device 102. In an embodiment, the power source 300 comprises at least one rechargeable power source 302.

In an embodiment, the monitoring device 102 can include, but is not limited to, one or more biological-subject (e.g., human)-powered generators 304. In an embodiment, the biological-subject-powered generator 304 is configured to harvest energy from for example, but not limited to, motion of one or more joints. In an embodiment, the biological-subject-powered generator 304 is configured to harvest energy generated by the biological subject using at least one of a thermoelectric generator 306, piezoelectric generator 308, microelectromechanical systems (MEMS) generator 312, biomechanical-energy harvesting generator 314, and the like.

In an embodiment, the biological-subject-powered generator 304 is configured to harvest thermal energy generated by the biological subject. In an embodiment, a thermoelectric generator 306 is configured to harvest heat dissipated by the biological subject. In an embodiment, the biological-subject-powered generator 304 is configured to harvest energy generated by any physical motion or movement (e.g., walking,) by biological subject. For example, in an embodiment, the biological-subject-powered generator 304 is configured to harvest energy generated by the movement of a joint within the biological subject. In an embodiment, the biological-subject-powered generator 304 is configured to harvest energy generated by the movement of a fluid within the biological subject.

Among power sources 300 examples include, but are not limited to, one or more button cells, chemical battery cells, a fuel cell, secondary cells, lithium ion cells, micro-electric patches, nickel metal hydride cells, silver-zinc cells, capacitors, super-capacitors, thin film secondary cells, ultra-capacitors, zinc-air cells, and the like. Further non-limiting examples of power sources 300 include one or more generators (e.g., electrical generators, thermo energy-to-electrical energy generators, mechanical-energy-to-electrical energy generators, micro-generators, nano-generators, and the like) such as, for example, thermoelectric generators, piezoelectric generators, microelectromechanical systems (MEMS) generators, biomechanical-energy harvesting generators, and the like. In an embodiment, the monitoring device 102 can include, but is not limited to, one or more generators configured to harvest mechanical energy from for example, ultrasonic waves, mechanical vibration, blood flow, and the like. In an embodiment, the monitoring device 102 can include one or more power receivers configurable to receive power from an in vivo power source.

In an embodiment, the power source 300 includes at least one of a thermoelectric generator, a piezoelectric generator, a microelectromechanical systems (MEMS) generator, or a biomechanical-energy harvesting generator, and at least one of a button cell, a chemical battery cell, a fuel cell, a secondary cell, a lithium ion cell, a micro-electric patch, a nickel metal hydride cell, silver-zinc cell, a capacitor, a super-capacitor, a thin film secondary cell, an ultra-capacitor, or a zinc-air cell. In an embodiment, the power source 300 includes at least one rechargeable power source.

In an embodiment, the monitoring device 102 can include, but is not limited to, a power source 300 including at least one of a thermoelectric generator a piezoelectric generator, a microelectromechanical systems (MEMS) generator, or a biomechanical-energy harvesting generator. In an embodiment, the power source 300 is configured to wirelessly receive power from a remote power supply. In an embodiment, the power source 300 is configured to manage a duty cycle associated with emitting an effective amount of an interrogation stimulus from the energy emitter component 104.

In an embodiment, the energy emitter component 104 is configured to provide a voltage across at least a portion of the tissue proximate the monitoring device 102 from a power source 300 coupled to the monitoring device 102.

The monitoring device 102 may include a transcutaneous energy transfer system 316. In an embodiment, the transcutaneous energy transfer system 316 is configured to transfer power from an in vivo power source to the monitoring device 102. In an embodiment, the transcutaneous energy transfer system 316 is configured to transfer power to the monitoring device 102 and to recharge a power source 300 within the monitoring device 102. In an embodiment, the monitoring device 102 may include a power receiver configurable to receive power from an in vivo power source.

In an embodiment, the transcutaneous energy transfer system 316 is electromagnetically, magnetically, ultrasonically, optically, inductively, electrically, or capacitively-coupleable to an in vivo power supply. In an embodiment, the transcutaneous energy transfer system 316 is electromagnetically, magnetically, ultrasonically, optically, inductively, electrically, or capacitively-coupleable to the energy emitter component 104. In an embodiment, the transcutaneous energy transfer system 316 includes at least one electromagnetically-coupleable power supply 318, magnetically-coupleable power supply 320, ultrasonically-coupleable power supply 322, optically-coupleable power supply 324, inductively-coupleable power supply 326, electrically-coupleable power supply 328, or capacitively-coupleable power supply 330.

Figure 4:
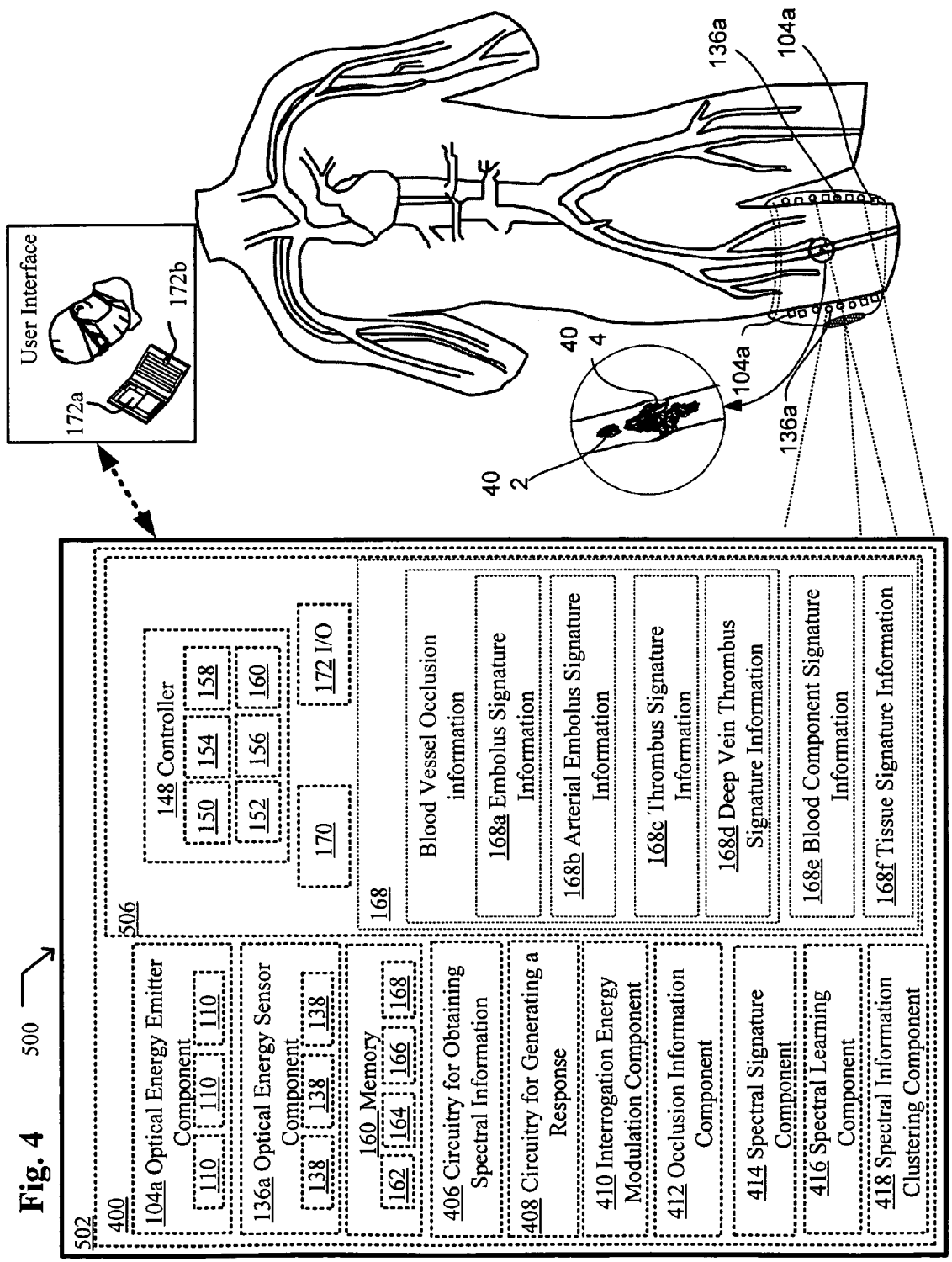
FIG. 4 is a schematic diagram of a system including one or more monitoring devices according to one illustrated embodiment.

Referring to FIG. 4, in an embodiment, the system 100 can include, but is not limited to, an optical energy emitter component 104a. In an embodiment, the optical energy emitter component 104a is configured to direct an ex vivo generated pulsed optical energy stimulus along an optical path for a time sufficient to interact with one or more regions within the biological subject. In an embodiment, the optical energy emitter component 104a is configured to direct a pulsed optical energy stimulus along an optical path in an amount and for a time sufficient to elicit the formation of acoustic waves associated with changes in a biological mass present along the optical path. In an embodiment, the system 100 is configured to optically detect an occlusion including for example, but not limited to, an embolus 402, a thrombus 404, or the like in one or more fluid flow vessel of biological subject.

The system 100 can include, but is not limited to, an optical energy sensor component 136a. In an embodiment, the optical energy sensor component 136a is configured to detect (e.g., assess, calculate, evaluate, determine, gauge, measure, monitor, quantify, resolve, sense, or the like) at least one of an emitted optical energy or a remitted optical energy and to generate a first response based on the detected at least one of the emitted optical energy or the remitted optical energy. In an embodiment, the optical energy sensor component 136a is configured to detect an emitted optical energy and a remitted optical energy and to generate a first response based on the detected emitted and remitted optical energy.

In an embodiment, the first response includes, but is not limited to, at least one of a response signal, a real-time model parameter, a real-time model update parameter, a real-time model seed parameter, or a real-time occlusion formation model parameter. In an embodiment, the first response includes, but is not limited to, a signal indicative of a parameter associated with an embolus, thrombus, or a deep vein thrombus present in a region of a tissue proximate the optical energy sensor component 136a. In an embodiment, the first response includes, but is not limited to, a signal indicative of temporal pattern associated with a detected optical waveform. In an embodiment, the first response includes, but is not limited to, a time-integrated signal indicative of a parameter associated with an embolus, thrombus, or a deep vein thrombus present in a region of a tissue along an optical path.

In an embodiment, the first response includes, but is not limited to, spectral information associated with an embolus, thrombus, or a deep vein thrombus present in a region of a tissue proximate the optical energy sensor component 136a. In an embodiment, the first response includes, but is not limited to, a spectral image of an embolus, thrombus, or a deep vein thrombus. In an embodiment, the first response includes, but is not limited to, at least one of an optical absorption spectrum, a photo-acoustic image, a thermo-acoustic imagine, or a photo-acoustic/thermo-acoustic tomographic image. In an embodiment, the first response includes a visual representation indicative of a parameter associated with an embolus, thrombus, or a deep vein thrombus present in a region of a tissue proximate the optical energy sensor component.

The system 100 can include, but is not limited to, one or more computer-readable memory media having blood vessel occlusion information configured as a data structure 168. In an embodiment, the blood vessel occlusion information includes one or more heuristically determined parameters associated with at least one in vivo or in vitro determined metric. In an embodiment, the one or more heuristically determined parameters include, but are not limited to, at least one of a threshold level or a target parameter. In an embodiment, the one or more heuristically determined parameters include threshold information. In an embodiment, the one or more heuristically determined parameters include at least one of threshold embolus spectral signature information, threshold arterial embolus spectral signature information, threshold thrombus spectral signature information, or threshold deep vein thrombus spectral signature information. In an embodiment, the one or more heuristically determined parameters include at least one of a heuristic protocol determined parameter or a heuristic algorithm determined parameter. In an embodiment, the one or more heuristically determined parameters include at least one occlusion formation model seed parameter. In an embodiment, the one or more heuristically determined parameters include one or more seed parameters for at least one of an occlusion spectral model, a blood spectral model, a fat spectral model, a muscle spectral model, or a bone spectral model. In an embodiment, the one or more heuristically determined parameters include one or more seed parameters for at least one of a hair spectral model or a lymphatic system tissue spectral model. In an embodiment, the one or more heuristically determined parameters include one or more seed parameters for a medical implant spectral model.

In an embodiment, the blood vessel occlusion information configured as the data structure includes a data structure including a characteristic spectral signature information section having characteristic tissue spectral signature information. In an embodiment, the blood vessel occlusion information configured as the data structure includes a data structure including a characteristic spectral signature information section having at least one of blood spectral signature information, fat spectral information, muscle spectral signature information, or a bone spectral signature information. In an embodiment, the blood vessel occlusion information configured as the data structure includes a data structure including a characteristic spectral signature information section having lymphatic system tissue spectral signature information. In an embodiment, the blood vessel occlusion information configured as the data structure includes a data structure including a characteristic spectral signature information section having hair spectral signature information. In an embodiment, the blood vessel occlusion information configured as the data structure includes a data structure including a characteristic spectral signature information section having indwelling implant spectral signature information.

In an embodiment, the data structure 168 includes, but is not limited to, characteristic embolus spectral signature information 168a representative of the presence of at least a partial occlusion in a blood vessel. In an embodiment, the characteristic embolus spectral signature information 168a includes at least one of a characteristic embolus absorption value indicative of an embolus absorption coefficient, a characteristic embolus extinction value indicative of an embolus extinction coefficient, or a characteristic embolus scattering value indicative of an embolus scattering coefficient. In an embodiment, the characteristic embolus spectral signature information 168a includes at least one of characteristic embolus absorption coefficient data, characteristic embolus extinction coefficient data, or characteristic embolus scattering coefficient data.

In an embodiment, the data structure 168 includes, but is not limited to, characteristic arterial embolus spectral signature information 168b representative of the presence of at least a partial occlusion in an artery. In an embodiment, the characteristic arterial embolus spectral signature information 168b includes at least one of a characteristic arterial embolus absorption value indicative of an arterial embolus absorption coefficient, a characteristic arterial embolus extinction value indicative of an arterial embolus extinction coefficient, or a characteristic arterial embolus scattering value indicative of an arterial embolus scattering coefficient. In an embodiment, the characteristic arterial embolus spectral signature information 168b includes at least one of characteristic arterial embolus absorption coefficient data, characteristic arterial embolus extinction coefficient data, or characteristic arterial embolus scattering coefficient data. In an embodiment, the characteristic arterial embolus spectral signature information 168b includes at least one spectral parameter associated with a peripheral artery occlusion.

In an embodiment, the data structure 168 includes characteristic thrombus spectral signature information 168c representative of at least a partial blood clot formation in a blood vessel. In an embodiment, the characteristic thrombus spectral signature information 168c includes at least one of a characteristic thrombus absorption value indicative of a thrombus absorption coefficient, a characteristic thrombus extinction value indicative of a thrombus extinction coefficient, or a characteristic thrombus scattering value indicative of a thrombus scattering coefficient. In an embodiment, the characteristic thrombus spectral signature information 168c includes at least one of characteristic thrombus absorption coefficient data, characteristic thrombus extinction coefficient data, or characteristic thrombus scattering coefficient data.

In an embodiment, the data structure 168 includes, but is not limited to, characteristic deep vein thrombus spectral signature information 168d representative of at least a partial blood clot formation in a deep vein. In an embodiment, the characteristic deep vein thrombus spectral signature information 168d includes at least one of a characteristic deep vein thrombus absorption value indicative of a deep vein thrombus absorption coefficient, a characteristic deep vein thrombus extinction value indicative of a deep vein thrombus extinction coefficient, or a characteristic deep vein thrombus scattering value indicative of a deep vein thrombus scattering coefficient. In an embodiment, the characteristic deep vein thrombus spectral signature information 168d includes at least one of characteristic deep vein thrombus absorption coefficient data, characteristic deep vein thrombus extinction coefficient data, or characteristic deep vein thrombus scattering coefficient data.

In an embodiment, the data structure 168 can include, but is not limited to, at least one of characteristic blood component spectral signature information 168e or tissue spectral signature information 168f. The occlusion-monitoring system can include, but is not limited to, one or more controllers 148 configured to compare the generated first response to the blood vessel occlusion information, and to generate a second response based on the comparison.

The system 100 can include, but is not limited to, one or more computer-readable memory media having inflammation spectral information configured as a data structure 168. In an embodiment, the data structure 168 includes a spectral signature information section having one or more spectral parameters associated with at least one of an infection component, an inflammation component, an infective stress component, or a sepsis component.

The system 100 can include, but is not limited to, a control means 400. The control means 400 may include for example, but not limited to, electrical control components, electromechanical control components, software control components, firmware control components, or other control components, or combinations thereof. In an embodiment, the control means 400 may include electrical control component circuitry configured to for example, but not limited to, control at least one of an interrogation energy delivery regimen parameter, a spaced-apart interrogation energy delivery pattern parameter, a spatial electric field modulation parameter, a spatial electric field magnitude parameter, or a spatial electric field distribution parameter associated with the delivery of the interrogation energy. In an embodiment, the control means 400 may include electrical control component circuitry configured to for example, but not limited to, control one or more energy emitter components 104 and one or more sensor components 136. Further examples of circuitry can be found, among other things, in U.S. Pat. No. 7,236,821 (issued Jun. 26, 2001), the contents of which is incorporated herein by reference.

In a general sense, the various aspects described herein (which can be implemented, individually and/or collectively, by a wide range of hardware, software, firmware, and/or any combination thereof) can be viewed as being composed of various types of "electrical circuitry." Consequently, as used herein electrical circuitry or electrical control component circuitry includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). The subject matter described herein may be implemented in an analog or digital fashion or some combination thereof.

In an embodiment, the control means 400 may include one or more electro-mechanical systems configured to for example, control at least one of a interrogation energy delivery regimen parameter, a spaced-apart interrogation energy delivery pattern parameter, a spatial electric field modulation parameter, a spatial electric field magnitude parameter, or a spatial electric field distribution parameter associated with the delivery of the interrogation energy. In an embodiment, the control means 400 may include one or more electromechanical systems configured to for example, but not limited to, control the delivery and detection of interrogation energy. In a general sense, the various embodiments described herein can be implemented, individually and/or collectively, by various types of electro-mechanical systems having a wide range of electrical components such as hardware, software, firmware, and/or virtually any combination thereof; and a wide range of components that may impart mechanical force or motion such as rigid bodies, spring or torsional bodies, hydraulics, electro-magnetically actuated devices, and/or virtually any combination thereof.

Consequently, as used herein electromechanical system includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs. Examples of electromechanical systems include, but are not limited to, a variety of consumer electronics systems, medical devices, as well as other systems such as motorized transport systems, factory automation systems, security systems, and/or communication/computing systems. The term, electromechanical, as used herein is not necessarily limited to a system that has both electrical and mechanical actuation except as context may dictate otherwise.

In an embodiment, the system 100 can include for example, but not limited to, a control means 400 including a processor configured to compare to a detected emitted optical or remitted optical energy, and to generate a first response based on the detected emitted or remitted optical energy. In an embodiment, the system 100 can include for example, but not limited to, a control means 400 including a processor configured to compare to the generated first response to the blood vessel occlusion information, and to generate a second response based on the comparison. In an embodiment, the system 100 can include for example, but not limited to, a control means 400 including a processor configured to generate at lease one of a response signal, an absorption parameter, an extinction parameter, a scattering parameter, a comparison code, a comparison plot, a diagnostic code, a treatment code, an alarm response, or a test code based on the comparison of the detected optical energy absorption profile to the blood vessel occlusion information. In an embodiment, the system 100 can include for example, but not limited to, a control means 400 configured to generate the response based on the comparison of a measurand that modulates with a detected heart beat of the biological subject to a target value associated with the tissue spectral model. In an embodiment, the system 100 can include for example, but not limited to, a control means 400 including a processor configured to compare a measurand associated with the biological subject to a threshold value associated with the tissue spectral model and to generate a response based on the comparison. In an embodiment, the system 100 can include for example, but not limited to, a control means 400 including a processor configured to compare a measurand associated with the biological subject to the threshold value associated with the tissue spectral model and to generate a real-time estimation of the formation of an obstruction of a flow in a blood vessel based on the comparison. In an embodiment, the system 100 can include for example, but not limited to, a control means 400 including a processor configured to execute instructions, and a memory that stores instructions configured to cause the processor to generate the second response from information encoded in the data structure 168.

In an embodiment, the system 100 can include for example, but not limited to, a control means 400 for operably coupling to at least one of the optical energy emitter component 104*a* or the optical energy sensor component 136*a*. In an embodiment, the control means 400 is operable to control at least one component associated with the delivery of the interrogation energy. Such components may include for example, but not limited to, a delivery regimen component, a spaced-apart interrogation energy delivery pattern component, a spatial optical energy distribution component, or the like associated with the delivery of the interrogation energy. In an embodiment, the control means 400 is operable to control at least one interrogation energy delivery regimen parameter selected from an excitation intensity, an excitation frequency, an excitation pulse frequency, an excitation pulse ratio, an excitation pulse intensity, an excitation pulse duration time, an excitation pulse repetition rate, an ON-rate, or an OFF-rate. A "duty cycle" includes, but is not limited to, a ratio of a pulse duration ($\tau$) relative to a pulse period (T). For example, a pulse train having a pulse duration of 10 as and a pulse signal period of 40 as, corresponds to a duty cycle (D=$\tau$/T) of 0.25. In an embodiment, the control means 400 is operable to, for example, but not limited to, manage a duty cycle associated with emitting an effective amount of optical energy from the optical energy emitter component 104*a*.

The control means 400 can include, but is not limited to, one or more controllers 148 such as a processor (e.g., a microprocessor) 150, a central processing unit (CPU) 152, a digital signal processor (DSP) 154, an application-specific integrated circuit (ASIC) 156, a field programmable gate array 158, and the like, and combinations thereof, and may include discrete digital and/or analog circuit elements or electronics. In an embodiment, at least one control means 400 is coupled to an integrated circuit, and configured to analyze an output of one or more of the plurality of logic components and to determine at least one parameter associated with a cluster centroid deviation derived from a comparison of at least one parameter associated.

In an embodiment, the control means 400 is configured to wirelessly couple to an optical energy sensor component 136*a* that communicates via wireless communication with the control means 400. Examples of wireless communication include for example, optical connections, audio, ultraviolet connections, infrared, BLUETOOTH®, Internet connections, radio, network connections, and the like.

In an embodiment, the control means 400 includes at least one controller 148, which is communicably-coupled to at least one of the optical energy emitter component 104 or the sensor component 136. In an embodiment, the control means 400 includes at least one controller 148, which is communicably-coupled to at least one of the optical energy emitter component 104a or the optical energy sensor component 136a. In an embodiment, the control means 400 is configured to control at least one of a duration time, a delivery location, or a spatial-pattern stimulation configuration associated with the delivery of an emitted energy from the optical energy emitter component 104a.

The control means 400 can include, but is not limited to, one or more memories 160 that store instructions or data, for example, volatile memory (e.g., random access memory (RAM) 162, dynamic random access memory (DRAM), and the like) non-volatile memory (e.g., read-only memory (ROM) 164, electrically erasable programmable read-only memory (EEPROM), compact disc read-only memory (CD-ROM), and the like), persistent memory, and the like. Further non-limiting examples of one or more memories 160 include erasable programmable read-only memory (EPROM), flash memory, and the like. The one or more memories can be coupled to, for example, one or more controllers by one or more instruction, data, or power buses.

The control means 400 may include a computer-readable media drive or memory slot 170, and one or more input/output components 172 such as, for example, a graphical user interface, a display 172a, a keyboard 172b, a keypad, a trackball, a joystick, a touch-screen, a mouse, a switch, a dial, and the like, and any other peripheral device. The control means 400 may further include one or more databases 166, and one or more data structures 168. The computer-readable media drive or memory slot may be configured to accept computer-readable memory media. In an embodiment, a program for causing the system 100 to execute any of the disclosed methods can be stored on a computer-readable recording medium. Examples of computer-readable memory media include CD-R, CD-ROM, DVD, flash memory, floppy disk, hard drive, magnetic tape, magnetooptic disk, MINIDISC, non-volatile memory card, EEPROM, optical disk, optical storage, RAM, ROM, system memory, web server, and the like.

The control means 400 can include, but is not limited to, circuitry for performing a comparison of the determined at least one characteristic associated with the tissue proximate the monitoring device 102 to stored reference data following delivery of an interrogation stimulus by the energy emitting component 104. In an embodiment, the control means 400 may include circuitry for obtaining spectral information 406 and circuitry for generating a response 408 based at least in part on the obtained information.

The control means 400 can include, but is not limited to, an interrogation energy modulation component 408 configured to modulate at least one of an illumination pattern, an illumination intensity, an energy-emitting pattern, a peak emission wavelength, an ON-pulse duration, an OFF-pulse duration, or a pulse frequency associated with the delivery of an interrogation energy.

The control means 400 can include, but is not limited to, at least one of an occlusion information component 412, a spectral signature component 414, a spectral learning component 416, or a spectral information clustering component 418 configured to compare one or more parameters associated with a detected optical energy absorption profile to one or more information subsets associated with the characteristic spectral signature information. In an embodiment, one or more of the occlusion information component 412, spectral signature component 414, spectral learning component 416, or spectral information clustering component 418 can include, but are not limited to, one or more instances of electrical, electromechanical, software-implemented, firmware-implemented, or other control devices. In an embodiment, one or more of the occlusion information component 412, spectral signature component 414, spectral learning component 416, or spectral information clustering component 418 can include, but are not limited to, one or more instances of memory, processors, antennas, power, or other supplies; logic modules or other signaling modules; sensor or other such active or passive detection components; or piezoelectric transducers, shape memory elements, micro-electro-mechanical system (MEMS) elements, or other actuators.

In an embodiment, spectral information associated with a detected emitted or remitted energy is clustered into related groups based on similarity, dissimilarity, pairwise similarities, distances from a threshold value (e.g., a cluster centroid deviation), rate of change, affinity between points in Euclidean space, a hierarchy, an index of clustering, or the like. In an embodiment, spectral information associated with spectral characteristics of for example, but not limited to, one or more blood component is clustered into related groups based on similarity, dissimilarity, pairwise similarities, distances from a threshold value, rate of change, affinity between points in Euclidean space, a hierarchy, an index of clustering, or the like.

In an embodiment, clustering includes assigning spectral information into clusters such that spectral parameters from the same cluster are more similar to each other than spectral parameters from different clusters. Clustering technologies or methodologies can include, but are not limited to, Bayesian clustering, canonical correlation, conjoint analysis, discriminant analysis, factor analysis, hierarchical cluster analysis, hierarchical clustering, k-means clustering, linear regression analysis, logistic regression, multidimensional scaling, multiple discriminant analysis, multiple regression analysis, neural networks, resampling methods, self-organizing maps, structural equation modeling, support vector machine determined boundaries, or the like.

In an embodiment, spectral information associated with a detected emitted or remitted energy is clustered is analyzed using one or more statistical leaning technologies or methodologies. Statistical learning protocols include supervised and unsupervised protocols. Supervised learning techniques may include can include, but are not limited to, bagging, Bayesian statistical analysis, boosting of simple classifiers, decision trees, Fisher discriminant analysis, Gaussian process classifications and regressions, k-nearest-neighbor classifications, kernel density classifications, least angle regression, least-squares regressions, linear discriminant analysis, logistic regressions, minimax probability protocols, multi-class classifications, multi-label classifications, multiple additive regression trees, multivariate adaptive regression splines, Naive Bayes classifiers, neural networks for regression and classification, partial least-squares, Parzen windows classifiers, perceptron algorithms, ridge regressions, winnow algorithms, or the like. In an embodiment, supervised learning includes predicting an output based on a number of input factors or variables. In an embodiment, a prediction rule is learned from a set of characteristic examples each showing the output for a respective combination of variables.

In an embodiment, unsupervised learning includes generating associations and patterns among a set of variables without the guidance of a specific output. Unsupervised learning techniques may include can include, but are not limited to, canonical correlation analysis, clustering, density estimation techniques, dimensionality reduction, factor analysis, Gaussian mixture models, hierarchical clustering algorithms, independent component analysis, isomaps, kernel density estimation (using for example Parzen windows or k-nearest neighbors) k-means clustering local linear embedding, multi-dimensional scaling, novelty detection, quantile estimation, self-organizing maps, single-class classification (e.g., single-class support vector machine (SVM) algorithms, single-class minimax probability machine (MPM) algorithms, or the like), spectral clustering, or the like. (See, e.g., Rhinelander et al, *A Single-class Support Vector Machine Translation Algorithm To Compensate For Non-stationary Data In Heterogeneous Vision-based Sensor Networks*, Instrumentation and Measurement Technology Conference Proceedings 2008, 1102-1106 (2008), which is incorporated herein by reference); see, also U. von Luxburg, *A Tutorial on Spectral Clustering*, Technical Report No. TR-149, Max Plank Institute for Biological Cybernetics, 1-25 (August 2006), which is incorporated herein by reference).

Further examples of clustering technologies or methodologies may be found in, for example, the following documents (the contents of which are incorporated herein by reference): U.S. Pat. No. 7,412,429 (issued Aug. 12, 2008), U.S. Pat. No. 7,461,073 (issued Dec. 2, 2008), and U.S. Pat. No. 7,489,825 (issued Feb. 10, 2009).

Figure 5:
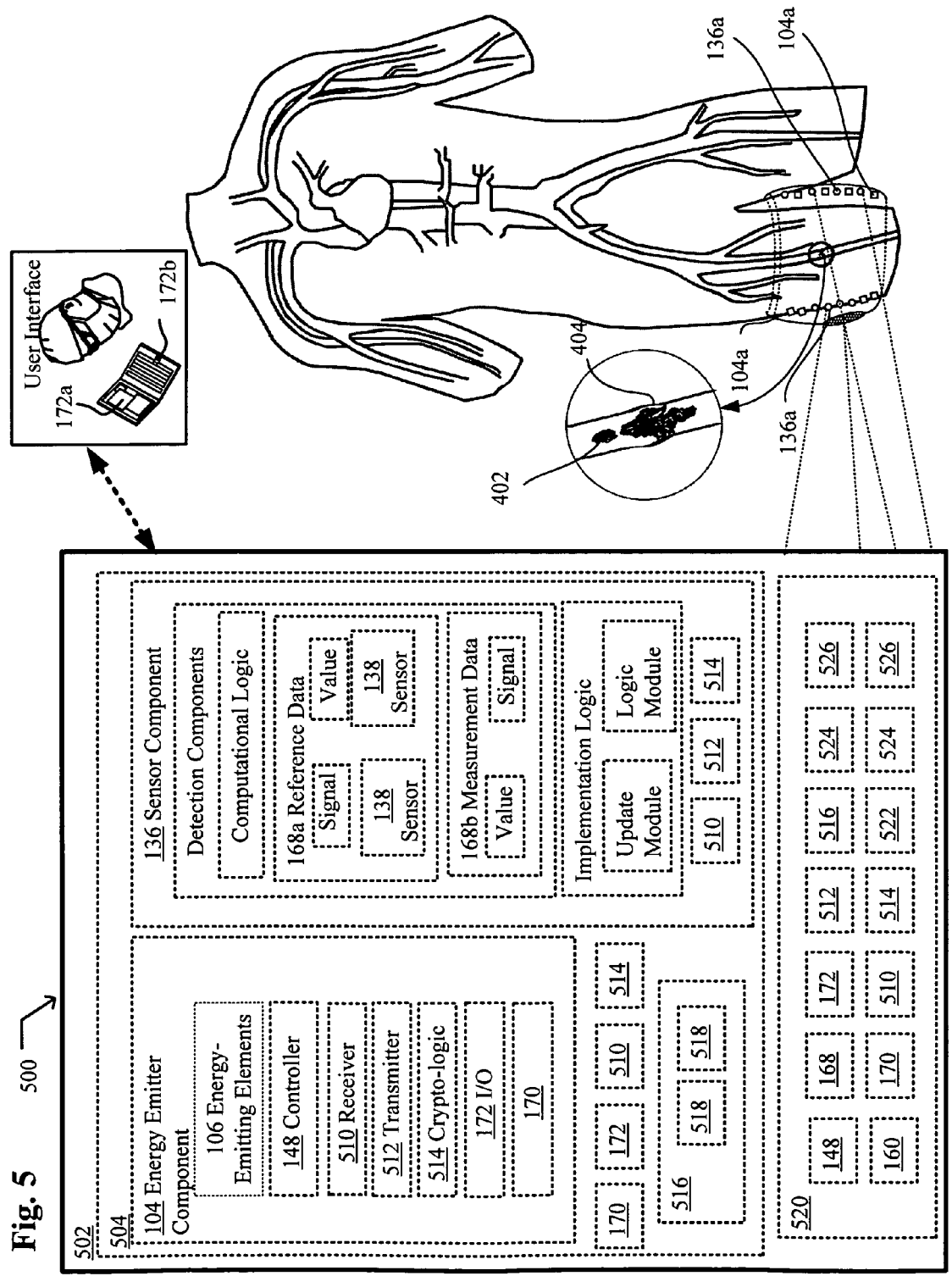
FIG. 5 is a schematic diagram of a system including one or more monitoring devices according to one illustrated embodiment.

In an embodiment, the control means 400 includes circuitry for executing at least one of a spectral clustering component 416 or a spectral information learning component 418 configured to compare one or more parameters associated with a detected optical energy absorption profile to one or more information subsets associated with the characteristic spectral signature information. In an embodiment, one or more information subsets include one or mode physical data structures 168 including the information subsets. In an embodiment, at least one of the spectral clustering component 416 or a spectral information learning component 418 can be configure to execute one or more a Fuzzy C-Means Clustering protocol, a Graph-Theoretic protocol, a Hierarchical Clustering protocol, a K-Means Clustering protocol, a Locality-Sensitive Hashing protocol, a Mixture of Gaussians protocol, a Model-Based Clustering protocol, a Cluster-Weighted Modeling protocol, an Expectations-Maximization protocol, a Principal Components Analysis protocol, or a Partitional protocol FIG. 5 shows an ex vivo system 500 in which one or more methodologies or technologies may be implemented such as, for example, actively sensing, treating, or preventing an occlusion, a hematological abnormality, a body fluid flow abnormality, or the like. The ex vivo system 100 can include, one or more monitoring devices 102 including for example, but not limited to, circuitry for obtaining spectral information 504 from a biological subject while varying at least one of a wavelength or a frequency associated with an interrogation optical excitation energy source. The circuitry for obtaining spectral information 504 can include, but is not limited to, at least one energy emitter component 104 including one or more energy emitters 106. The circuitry for obtaining spectral information 504 can include, but is not limited to, one or more sensor components 136 including one or more sensors 138.

The ex vivo system 500 can include, one or more monitoring devices 102 including for example, but not limited to, at least one receiver 510 configured to acquire information. In an embodiment, the at least one receiver 510 is configured to acquire information associated with a delivery of the interrogation energy. In an embodiment, the at least one receiver 510 is configured to acquire data. In an embodiment, the at least one receiver 510 is configured to acquire software. In an embodiment, the at least one receiver 510 is configured to receive data from one or more distal sensors. In an embodiment, the at least one receiver 510 is configured to receive stored reference data.

The ex vivo system 500 can include, for example, circuitry for providing information. In an embodiment, the circuitry for providing information includes circuitry for providing status information regarding for example the status of a monitoring device 102. In an embodiment, the circuitry for providing information includes circuitry for providing information regarding at least one characteristic associated with a tissue proximate the monitoring device 102. The ex vivo system 500 can include, one or more monitoring device 102 including for example, but not limited to, at least one transmitter 512 configured to send information. The system 100 can include, one or more monitoring device 102 including for example, but not limited to, circuitry for transmitting information.

The circuitry for obtaining spectral information 504 can include, but is not limited to, one or more cryptographic logic components 514. In an embodiment, at least one of the one or more cryptographic logic components 514 is configured to implement at least one cryptographic process, or cryptographic logic, or combinations thereof. Examples of a cryptographic process include, but are not limited to one ore more process associated with cryptographic protocols, decryption protocols, encryption protocols, regulatory compliance protocols (e.g., FDA regulatory compliance protocols, or the like), regulatory use protocols, authentication protocols, authorization protocols, delivery protocols, activation protocols, encryption protocols, decryption protocols, and the like. Examples of a cryptographic logic include one or more crypto-algorithms signal-bearing media, crypto controllers (e.g., crypto-processors), cryptographic modules (e.g., hardware, firmware, or software, or combinations thereof for implementing cryptographic logic, or cryptographic processes), and the like.

The circuitry for obtaining spectral information 504 can include, but is not limited to, one or more modules 516 optionally operable for communication with one or more user interfaces 172 operable for relaying user output and/or input. The one or more modules 516 can include one or more instances of (electrical, electromechanical, software-implemented, firmware-implemented, or other control) devices 518. Device 518 may comprise one or more instances of memory, processors, ports, detectors, valves, antennas, power, or other supplies; logic modules or other signaling modules; sensors or other such active or passive detection components; or piezoelectric transducers, shape memory elements, micro-electro-mechanical system (MEMS) elements, or other actuators. In an embodiment, the circuitry for obtaining spectral information 504 includes at least one energy emitter component 104. In an embodiment, the circuitry for obtaining spectral information 504 includes at least sensor component 136. In an embodiment, the circuitry for obtaining spectral information 504 is operable to detect at least one of a transmitted optical energy or a remitted optical energy, and to generate a first response based at least in part on the detected at least one of the transmitted optical energy or the remitted optical energy. In an embodiment, the circuitry for generating a response 506 includes one or more processors configured to perform a comparison of at least one parameter associated with the obtained spectral information to one or more information subsets derived from partitioning spectral information associated with the biological subject.

The circuitry for obtaining spectral information 504 can include, but is not limited to, at least one of a spectral learning component, spectral clustering component, blood vessel occlusion component, spectral signature component The ex vivo system can include, but is not limited to, circuitry for generating a response 520 based at least in part on a comparison of at least one parameter associated with the obtained spectral information to one or more information subsets derived from partitioning spectral information associated with the biological subject.

The ex vivo system can include, but is not limited to, circuitry for generating a response 520 including one or more logic device 522 having one or more look-up tables 524.

The ex vivo system 500 can include, for example, but not limited to, an integrated circuit 526 having a plurality of logic components. In an embodiment, the ex vivo system 500 can include, for example, but not limited to, an input device 172 coupled to the integrated circuit 526. In an embodiment, the input device 172 is configured to provide data indicative of one or more spectral events associated with a detected at least one of a transmitted optical energy or a remitted optical energy.

The ex vivo system 500 can include, for example, but not limited to, one or more controllers 148 coupled to the integrated circuit 526. In an embodiment, the one or more controllers 148 are configured to analyze an output of one or more of the plurality of logic components and to determine at least one parameter associated with a cluster centroid deviation derived from a comparison of at least one parameter associated with the detect at least one of the transmitted optical energy or the remitted optical energy to a threshold diameter of at least one cluster associated with a set of reference cluster information.

In an embodiment, system 100 comprises a computer system. The computer system includes, but is not limited to, signal-bearing medium comprising spectral information associated with at least one of characteristic spectral signature information or detected optical energy absorption information associated with a portion of a tissue within a biological subject. In an embodiment, the spectral information is configured as a data structure 168. The computer system can include, but is not limited to, a shift register structure. In an embodiment, the shift register structure includes a first set of shift registers having a first plurality of shift registers interconnected in series. In an embodiment, at least one of the first plurality of registers configured to receive a clock signal having a shift frequency. In an embodiment, the first set of shift registers is configured to shift characteristic spectral signature information loaded into at least one shift register in the first set of shift registers to a next one of a shift register in the first set of shift registers according to the shift frequency.

In an embodiment, the shift register structure includes a second set of shift registers having a second plurality of shift registers interconnected in series. In an embodiment, the second set of shift registers includes one or more shift register loaded with the detected optical energy absorption information. In an embodiment, the shift register structure is configured to generate a comparison of the characteristic spectral signature information loaded in one or more shift register in the first set of shift registers to the detected optical energy absorption information loaded in one or more shift register in the second set of shift registers. In an embodiment, the shift register structure comprises at least one shift register lookup table. In an embodiment, the shift register structure comprises at least one of a static length shift register or a dynamic length shift register.

Figure 6A:
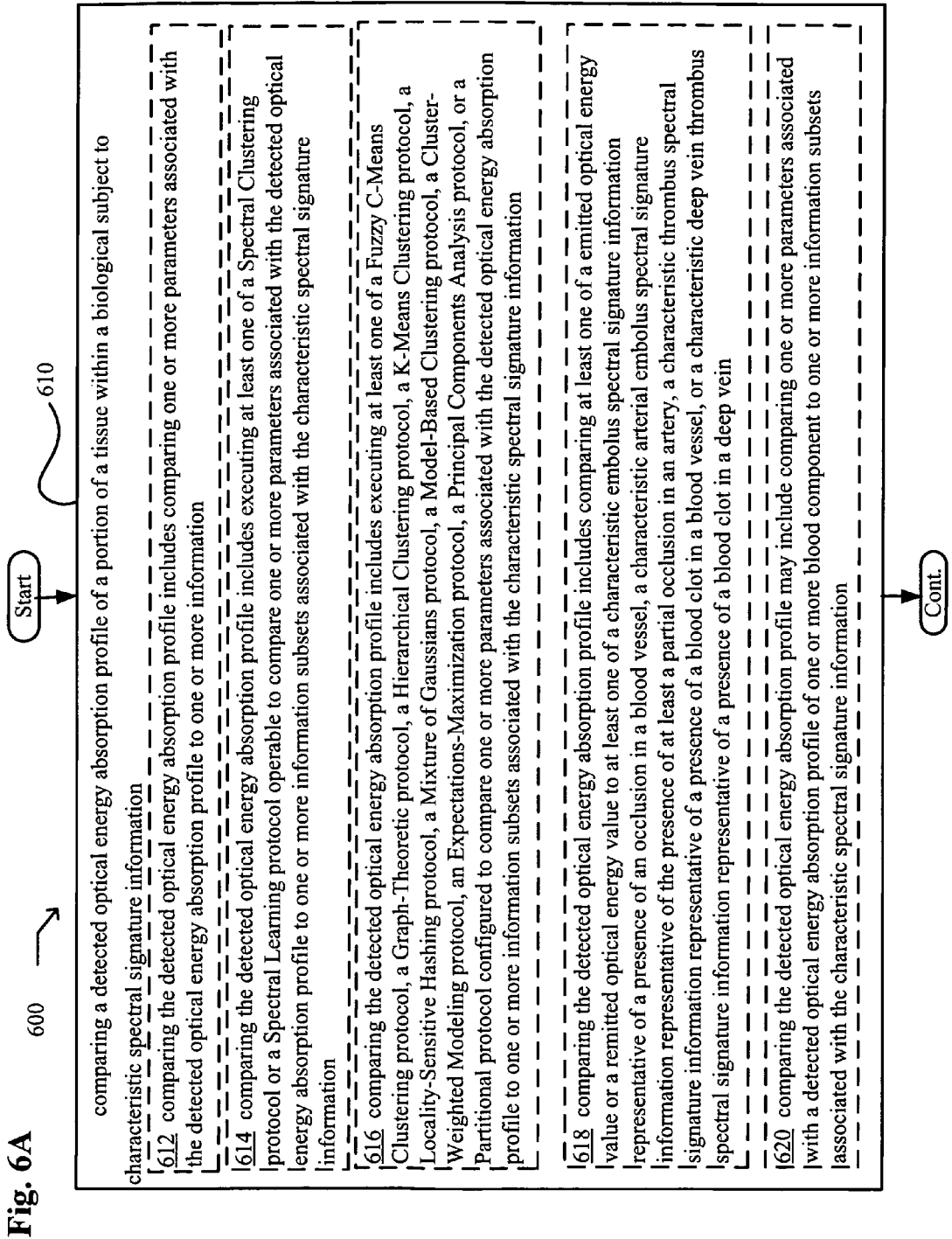
FIGS. 6A and 6B are flow diagrams of a method according to one illustrated embodiment.
Figure 6B:
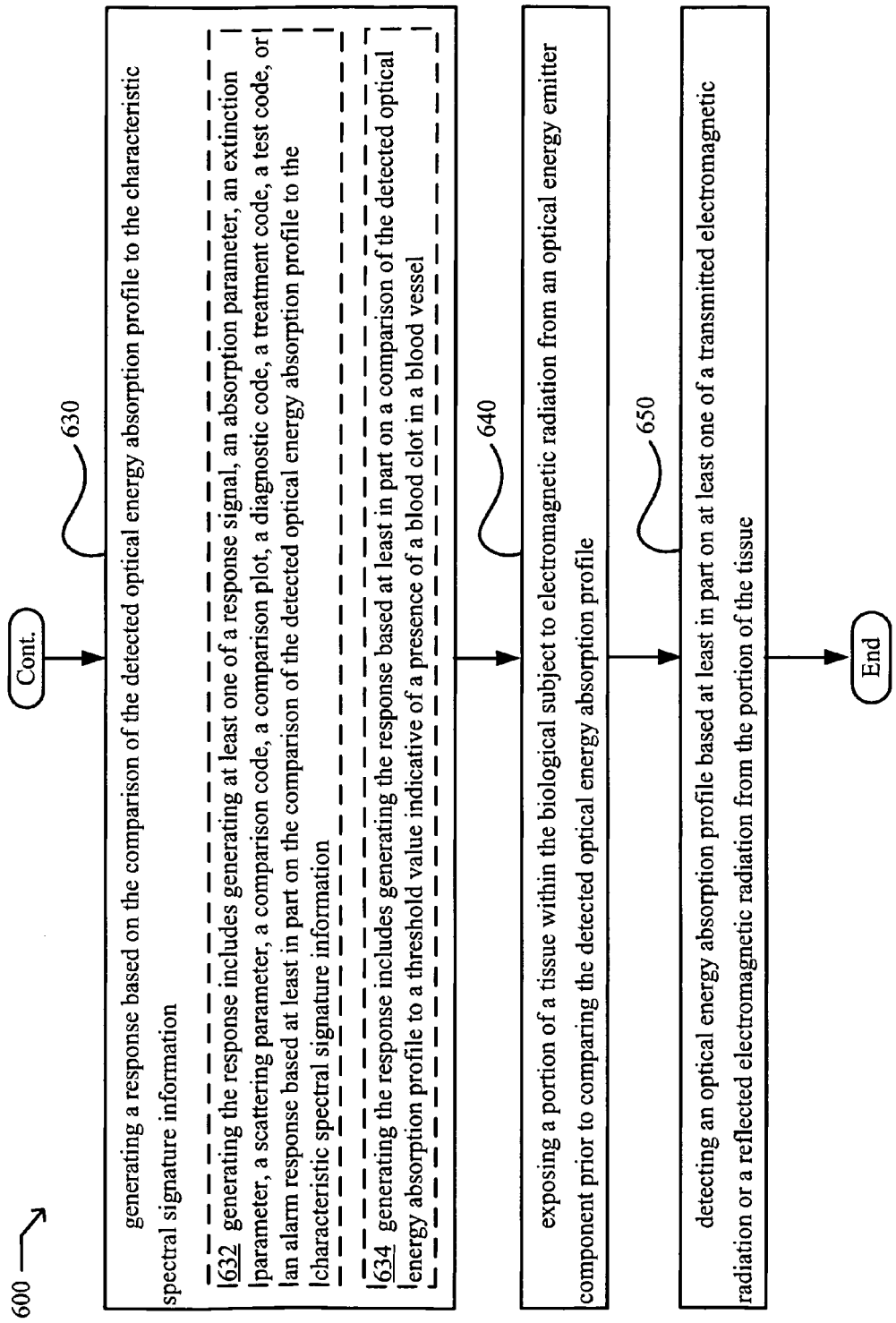

FIGS. 6A and 6B show an example of a method 600 for optically detecting an embolus, thrombus, or a deep vein thrombus in a biological subject.

At 610, the method 600 includes comparing a detected optical energy absorption profile of a portion of a tissue within a biological subject to characteristic spectral signature information, the detected optical energy absorption profile including at least one of an emitted optical energy or a remitted optical energy. At 612, comparing the detected optical energy absorption profile may include comparing one or more parameters associated with the detected optical energy absorption profile to one or more information subsets associated with the characteristic spectral signature information. At 614, comparing the detected optical energy absorption profile may include executing at least one of a Spectral Clustering protocol or a Spectral Learning protocol operable to compare one or more parameters associated with the detected optical energy absorption profile to one or more information subsets associated with the characteristic spectral signature information. At 616, comparing the detected optical energy absorption profile may include executing at least one of a Fuzzy C-Means Clustering protocol, a Graph-Theoretic protocol, a Hierarchical Clustering protocol, a K-Means Clustering protocol, a Locality-Sensitive Hashing protocol, a Mixture of Gaussians protocol, a Model-Based Clustering protocol, a Cluster-Weighted Modeling protocol, an Expectations-Maximization protocol, a Principal Components Analysis protocol, or a Partitional protocol configured to compare one or more parameters associated with the detected optical energy absorption profile to one or more information subsets associated with the characteristic spectral signature information. At 618, comparing the detected optical energy absorption profile of the portion of the tissue within the biological subject to the characteristic spectral signature information may include comparing at least one of an emitted optical energy value or a remitted optical energy value to at least one of a characteristic embolus spectral signature information representative of a presence of an occlusion in a blood vessel, a characteristic arterial embolus spectral signature information representative of the presence of at least a partial occlusion in an artery, a characteristic thrombus spectral signature information representative of a presence of a blood clot in a blood vessel, or a characteristic deep vein thrombus spectral signature information representative of a presence of a blood clot in a deep vein. At 619, comparing the detected optical energy absorption profile may include comparing one or more parameters associated with a detected optical energy absorption profile of one or more blood components to one or more information subsets associated with the characteristic spectral signature information.

At 630, the method 600 includes generating a response based on the comparison of the detected optical energy absorption profile to the characteristic spectral signature information. At 632, generating the response includes generating at least one of a response signal, an absorption parameter, an extinction parameter, a scattering parameter, a comparison code, a comparison plot, a diagnostic code, a treatment code, a test code, or an alarm response based at least in part on the comparison of the detected optical energy absorption profile to the characteristic spectral signature information. At 634, generating the response includes generating the response based at least in part on a comparison of the detected optical energy absorption profile to a threshold value indicative of a presence of a blood clot in a blood vessel.

At 640, the method 600 may further include exposing a portion of a tissue within the biological subject to electromagnetic radiation from an optical energy emitter component prior to comparing the detected optical energy absorption profile.

At 650, the method 600 may further include detecting an optical energy absorption profile based at least in part on at least one of a transmitted electromagnetic radiation or a reflected electromagnetic radiation from the portion of the tissue.

In an embodiment, a computer program product includes one or more signal-bearing media containing computer instructions which, when run on a computing device, cause the computing device to implement a method 700.

Figure 7:
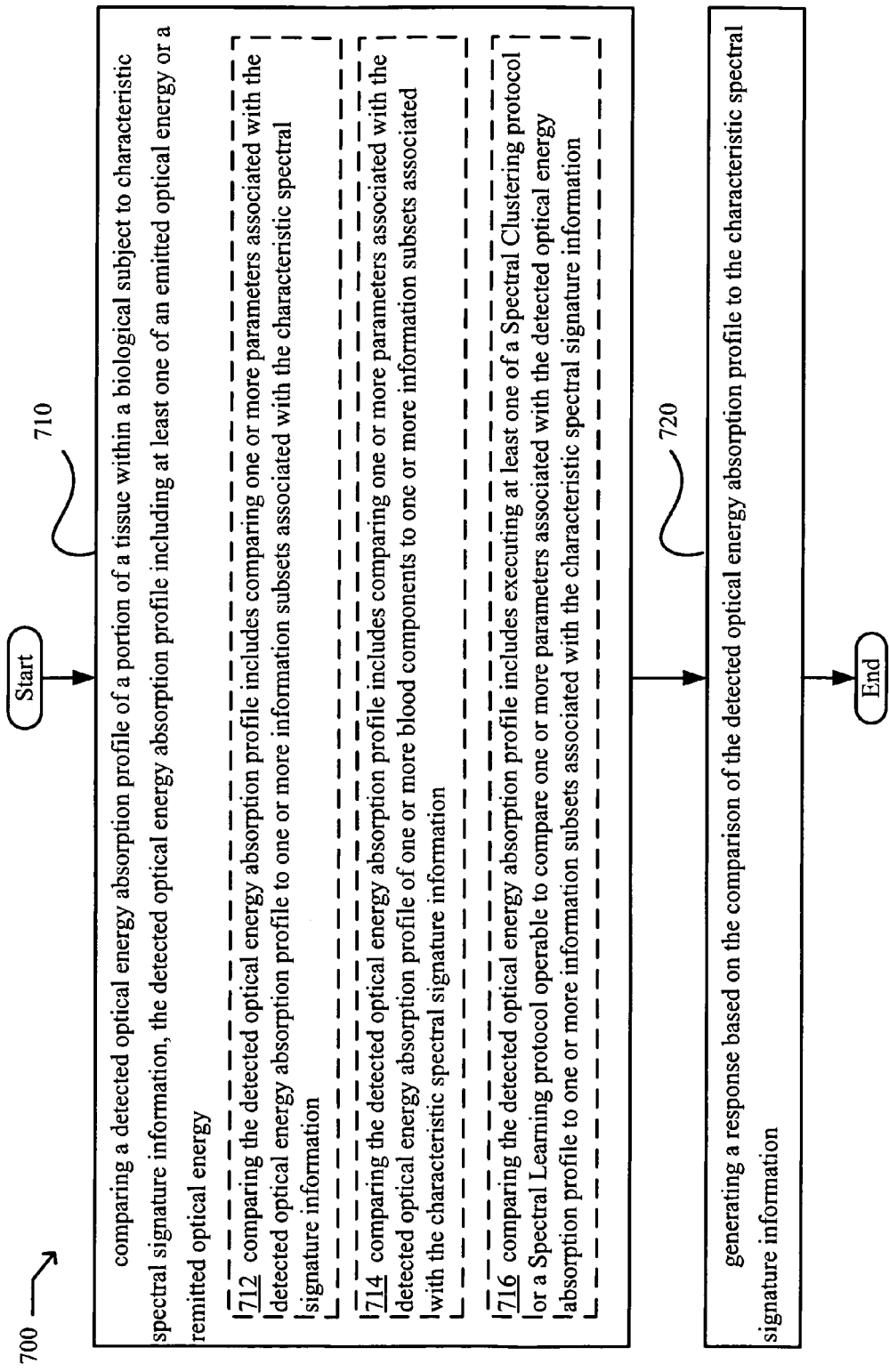
FIG. 7 is a flow diagram of a method according to one illustrated embodiment.

As shows in FIG. 7, at 710, the method 700 includes comparing a detected optical energy absorption profile of a portion of a tissue within a biological subject to characteristic spectral signature information, the detected optical energy absorption profile including at least one of an emitted optical energy or a remitted optical energy. At 712, comparing the detected optical energy absorption profile includes comparing one or more parameters associated with the detected optical energy absorption profile to one or more information subsets associated with the characteristic spectral signature information. At 714, comparing the detected optical energy absorption profile includes comparing one or more parameters associated with the detected optical energy absorption profile of one or more blood components to one or more information subsets associated with the characteristic spectral signature information. At 716, comparing the detected optical energy absorption profile includes executing at least one of a Spectral Clustering protocol or a Spectral Learning protocol operable to compare one or more parameters associated with the detected optical energy absorption profile to one or more information subsets associated with the characteristic spectral signature information.

At 720, the method 700 includes generating a response based on the comparison of the detected optical energy absorption profile to the characteristic spectral signature information.

Figure 8:
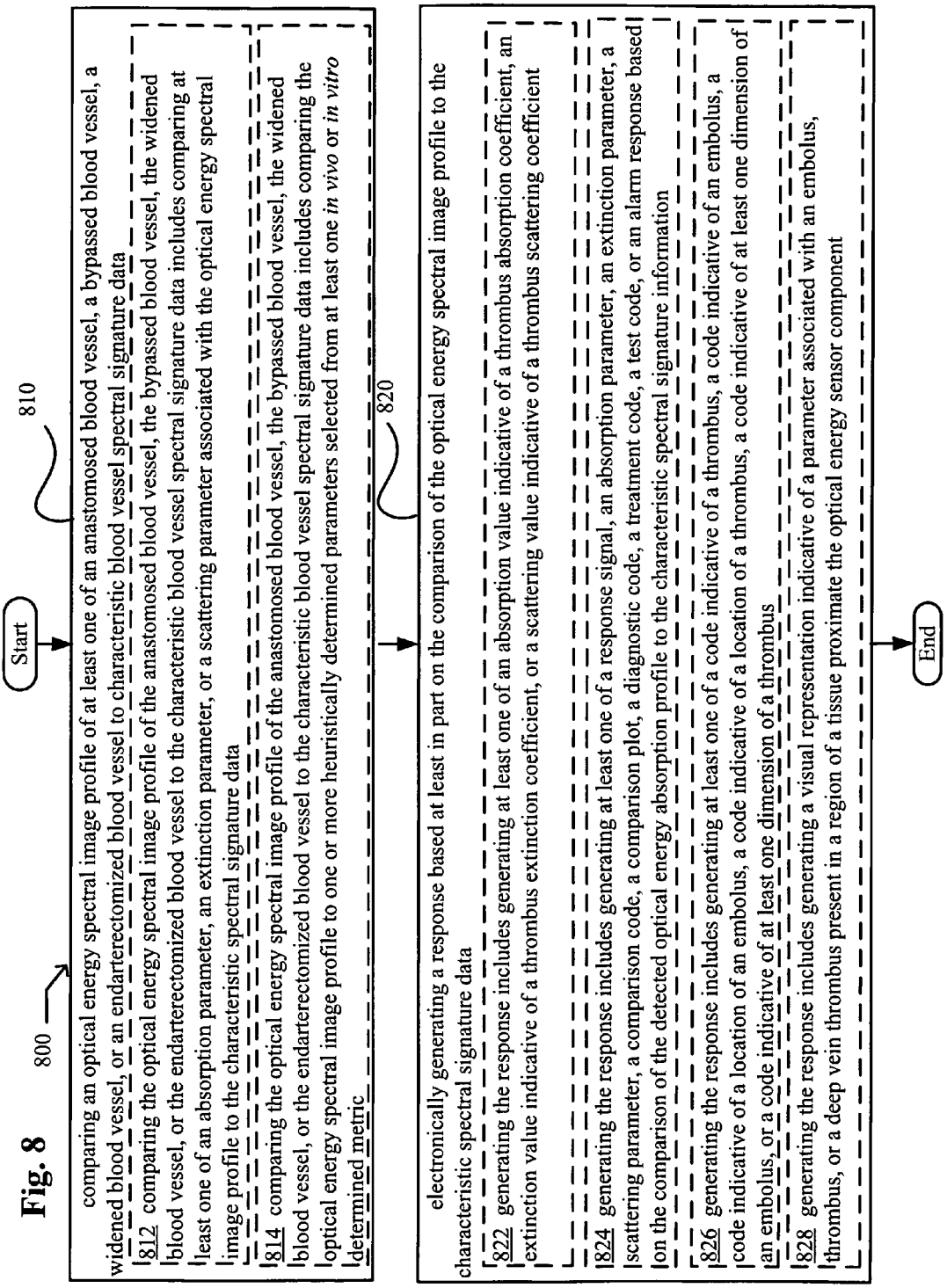
FIG. 8 is a flow diagram of a method according to one illustrated embodiment.

FIG. 8 shows an example of a method 800. At 810, the method 800 includes comparing an optical energy spectral image profile of an anastomosed blood vessel, a bypassed blood vessel, a widened blood vessel, or an endarterectomized blood vessel to characteristic blood vessel spectral signature data. At 812, comparing the optical energy spectral image profile of the anastomosed blood vessel, the bypassed blood vessel, the widened blood vessel, or the endarterectomized blood vessel to the characteristic blood vessel spectral signature data includes comparing at least one of an absorption parameter, an extinction parameter, or a scattering parameter associated with the optical energy spectral image profile to the characteristic spectral signature data. At 814, comparing the optical energy spectral image profile of the anastomosed blood vessel, the bypassed blood vessel, the widened blood vessel, or the endarterectomized blood vessel to the characteristic blood vessel spectral signature data includes comparing the optical energy spectral image profile to one or more heuristically determined parameters selected from at least one in vivo or in vitro determined metric.

At 820, the method 800 includes generating a response based at least in part on the comparison of the optical energy spectral image profile to the characteristic spectral signature data. At 822, electronically generating the response includes generating at least one of an absorption value indicative of a thrombus absorption coefficient, an extinction value indicative of a thrombus extinction coefficient, or a scattering value indicative of a thrombus scattering coefficient. At 824, electronically generating the response includes generating at least one of a response signal, an absorption parameter, an extinction parameter, a scattering parameter, a comparison code, a comparison plot, a diagnostic code, a treatment code, a test code, or an alarm response based on the comparison of the detected optical energy absorption profile to the characteristic spectral signature information. At 826, electronically generating the response includes generating at least one of a code indicative of a thrombus, a code indicative of an embolus, a code indicative of a location of an embolus, a code indicative of a location of a thrombus, a code indicative of at least one dimension of an embolus, or a code indicative of at least one dimension of a thrombus. At 828, electronically generating the response includes generating a visual representation indicative of a parameter associated with an embolus, thrombus, or a deep vein thrombus present in a region of a tissue proximate the optical energy sensor component.

Figure 9:
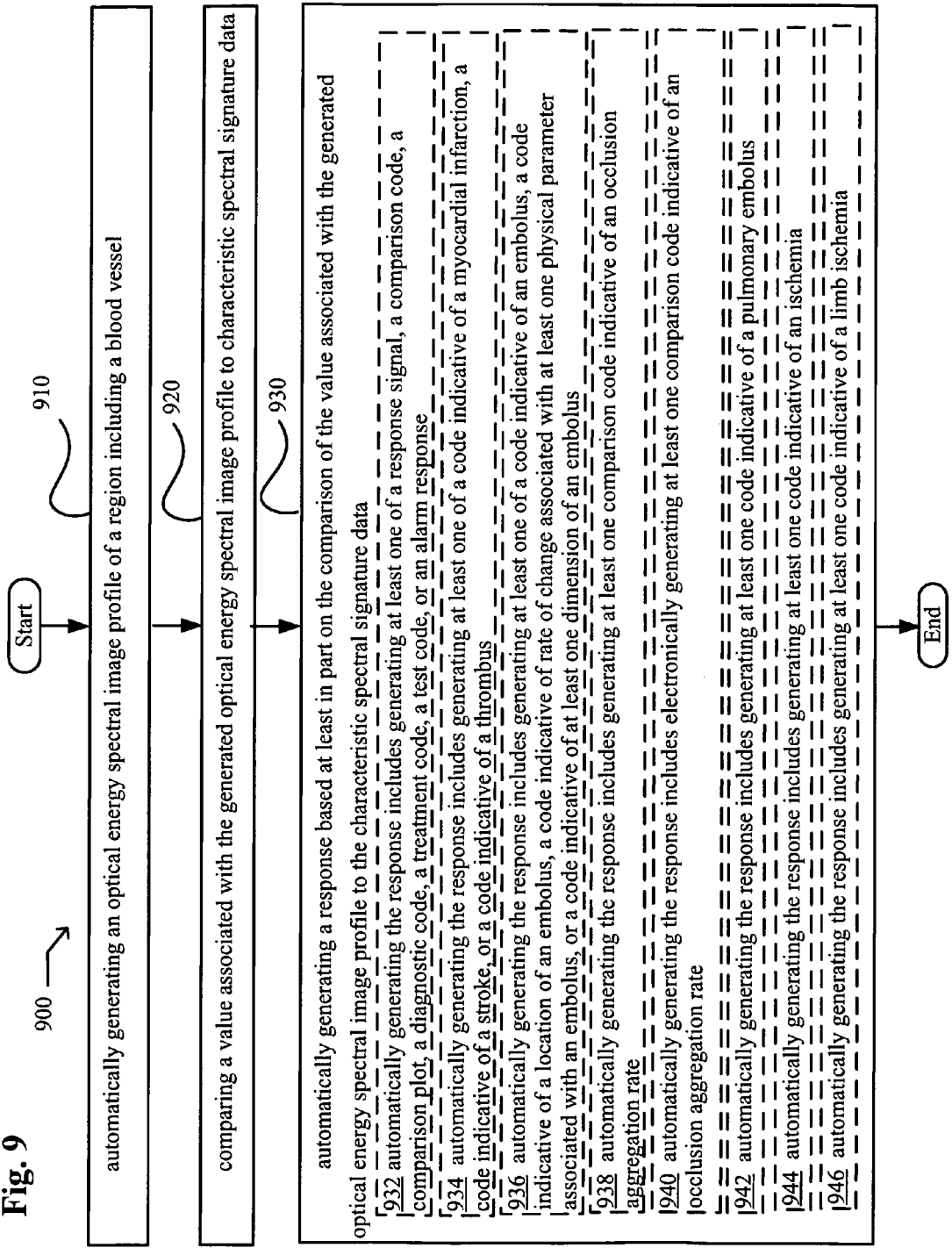
FIG. 9 is a flow diagram of a method according to one illustrated embodiment.

FIG. 9 shows an example of a method 900 for monitoring a biological subject for a condition associated with an obstructed blood vessel. At 910, the method 900 includes automatically generating an optical energy spectral image profile of a region including a blood vessel; and at 920, the method 900 comparing a value associated with the generated optical energy spectral image profile to characteristic spectral signature data, and at 930, the method 900 automatically generating a response based at least in part on the comparison of the value associated with the generated optical energy spectral image profile to the characteristic spectral signature data. In an embodiment, automatically generating a response includes electronically generating a response. At 932, automatically generating the response includes generating at least one of a response signal, a comparison code, a comparison plot, a diagnostic code, a treatment code, a test code, or an alarm response. At 934, automatically generating the response includes generating at least one of a code indicative of a myocardial infarction, a code indicative of a stroke, or a code indicative of a thrombus. In an embodiment, automatically generating the response my further include generating at least one of a code indicative of a subdural hematoma or a code indicative of an epidural hematoma. In an embodiment, automatically generating the response includes electronically generating at least one comparison code indicative of an occlusion aggregation rate, At 936, automatically generating the response includes generating at least one of a code indicative of an embolus, a code indicative of a location of an embolus, a code indicative of rate of change associated with at least one physical parameter associated with an embolus, or a code indicative of at least one dimension of an embolus. At 938, automatically generating the response includes generating at least one comparison code indicative of an occlusion aggregation rate. At 940, automatically generating the response includes electronically generating at least one comparison code indicative of an occlusion aggregation rate. At 942, automatically generating the response includes generating at least one code indicative of a pulmonary embolus. At 944, automatically generating the response includes generating at least one code indicative of an ischemia. At 946, automatically generating the response includes generating at least one code indicative of a limb ischemia.

Figure 10B:
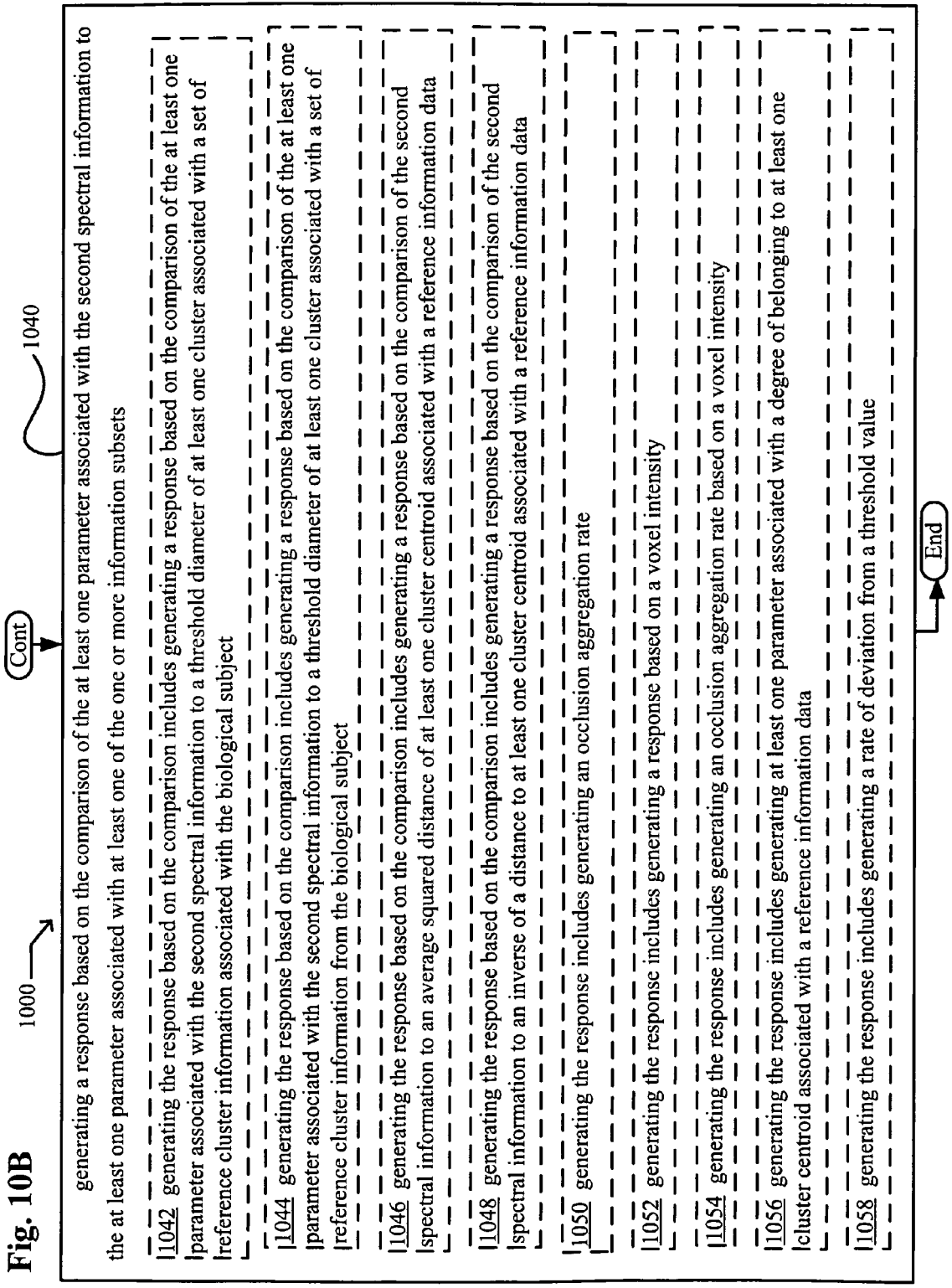

FIGS. 10A and 10B show a hemodynamics monitoring method 1000. At 1010, the method 1000 includes obtaining a first spectral information from a biological subject while varying at least one of a wavelength or a frequency associated with an interrogation optical excitation energy source. At 1020, the method 1000 includes partitioning the spectral information into one or more information subsets. At 1022, partitioning the spectral information into the one or more information subsets includes grouping the spectral information into one or more information subsets using a clustering protocol. At 1024, partitioning the spectral information into the one or more information subsets includes grouping the spectral information into one or more information subsets using at least one of a Spectral Clustering protocol or a Spectral Learning protocol. At 1026, partitioning the spectral information into the one or more information subsets includes grouping the spectral information into one or more information subsets using at least one of a Fuzzy C-Means Clustering protocol, a Graph-Theoretic protocol, a Hierarchical Clustering protocol, a K-Means Clustering protocol, a Locality-Sensitive Hashing protocol, a Mixture of Gaussians protocol, a Model-Based Clustering protocol, a Cluster-Weighted Modeling protocol, an Expectations-Maximization protocol, a Principal Components Analysis protocol, or a Partitional protocol. In an embodiment partitioning the spectral information into the one or more information subsets includes partitioning a detected spectrum into one or more information subsets with at least one of a prism, a monochromator, a diffraction grating (e.g., an electromagnetically deformable grating, an electrically deformable grating, a magnetically deformable grating, a controllably-deformable grating, a programmable diffraction grating, or the like), or a bypass filter. See. e.g., U.S. Pat. No. 6,985,294 (issued Jan. 10, 2006) (the contents of which are incorporated herein by reference).

At 1030, the method 1000 includes comparing at least one parameter associated with a second spectral information from a biological subject associated to at least one parameter associated with at least one of the one or more information subsets. At 1040, the method 1000 may include generating a response based on the comparison of the at least one parameter associated with the second spectral information to the at least one parameter associated with at least one of the one or more information subsets. At 1042, generating the response based on the comparison includes generating a response based on the comparison of the at least one parameter associated with the second spectral information to a threshold diameter of at least one cluster associated with a set of reference cluster information associated with the biological subject. At 1044, generating the response based on the comparison includes generating a response based on the comparison of the at least one parameter associated with the second spectral information to a threshold diameter of at least one cluster associated with a set of reference cluster information from the biological subject. At 1046, generating the response based on the comparison includes generating a response based on the comparison of the second spectral information to an average squared distance of at least one cluster centroid associated with a reference information data. At 1048, generating the response based on the comparison includes generating a response based on the comparison of the second spectral information to an inverse of a distance to at least one cluster centroid associated with a reference information data. At 1050, generating the response includes generating an occlusion aggregation rate. At 1052, generating the response includes generating a response based on a voxel intensity. At 1054, generating the response includes generating an occlusion aggregation rate based on a voxel intensity. At 1056, generating the response includes generating at least one parameter associated with a degree of belonging to at least one cluster centroid associated with a reference information data. At 1058, generating the response includes generating a rate of deviation from a threshold value.

Figure 11A:
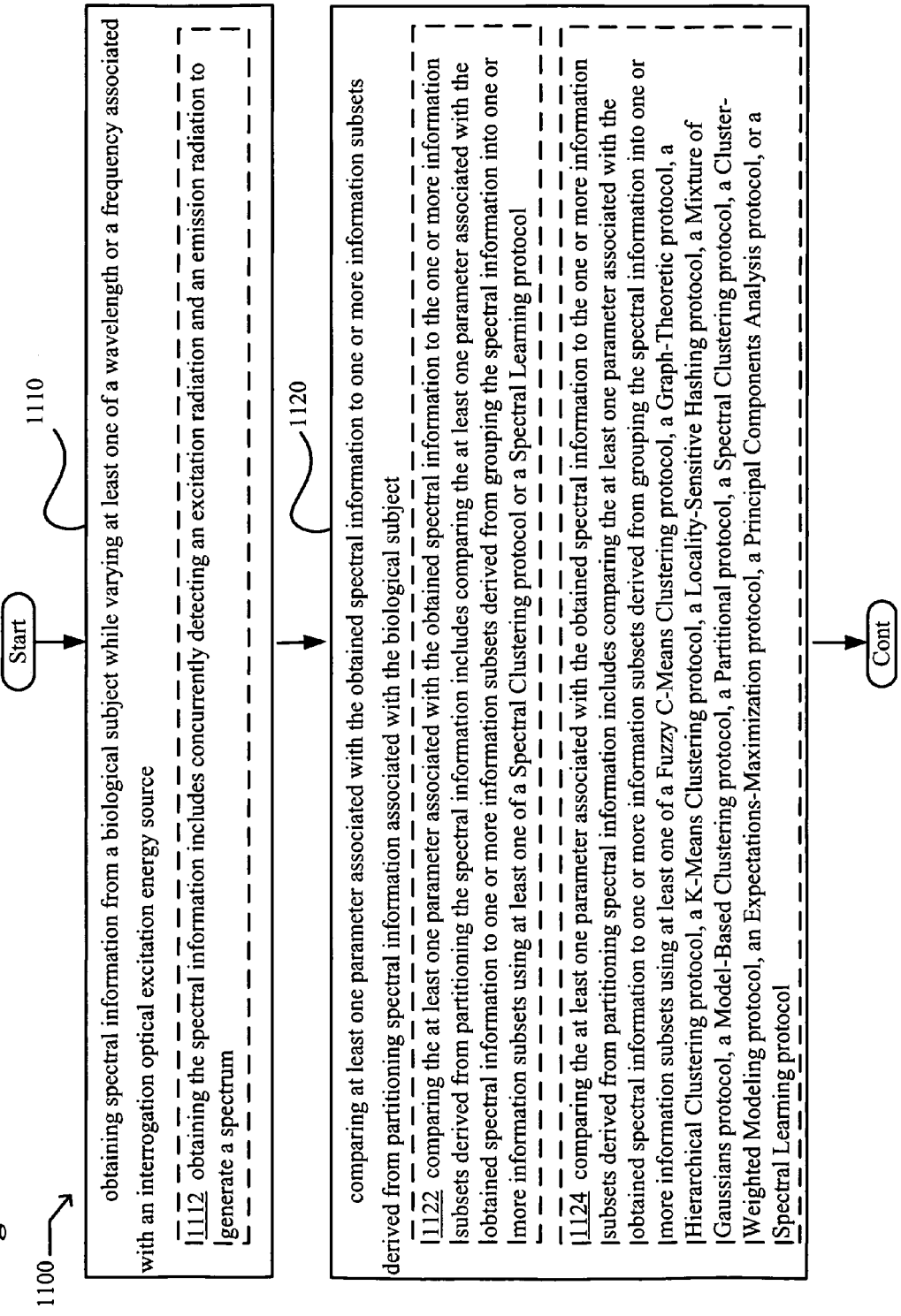
FIGS. 11A and 11B are flow diagrams of a method according to one illustrated embodiment.
Figure 11B:
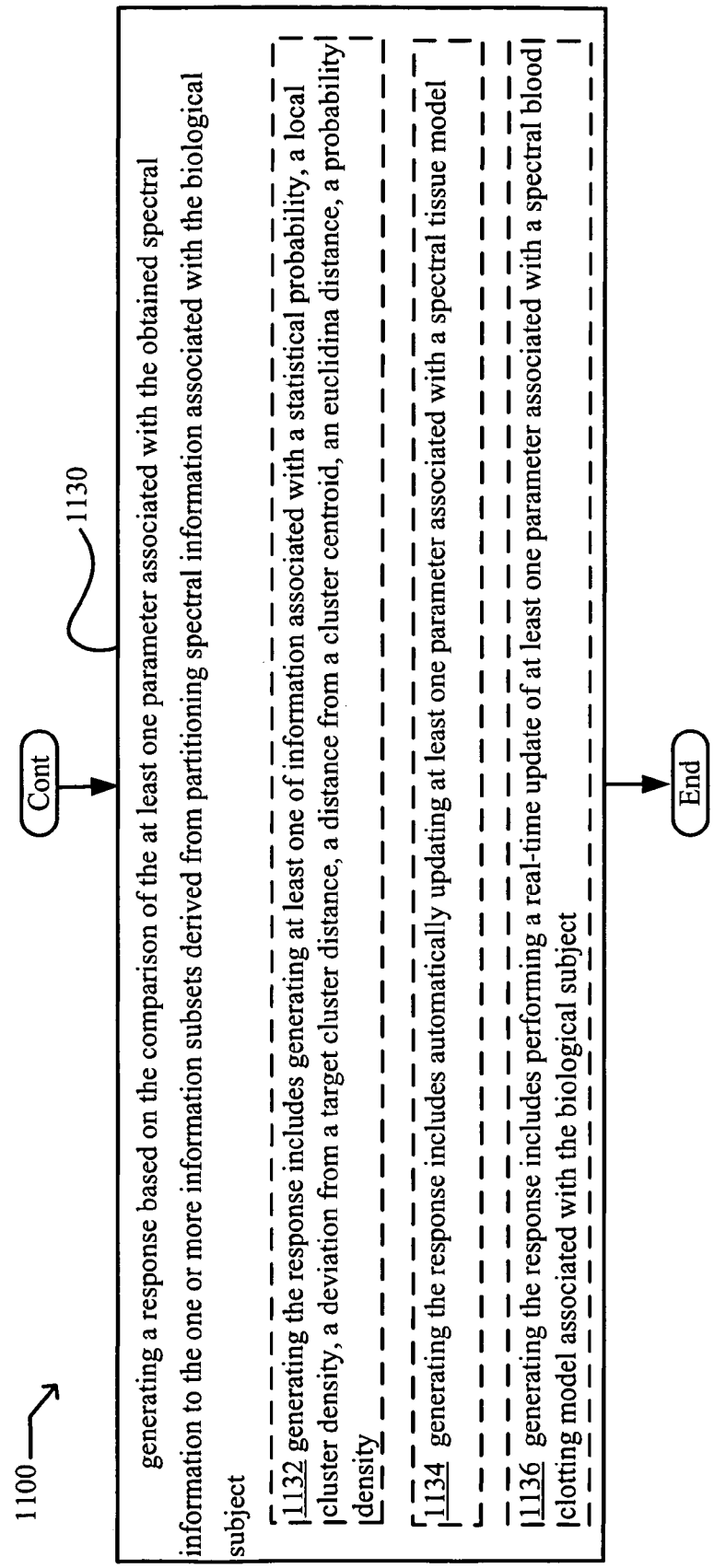

FIGS. 11A and 11B show an example of an occlusion monitoring method 1100. At 1110, the method 1100 includes obtaining spectral information from a biological subject while varying at least one of a wavelength or a frequency associated with an interrogation optical excitation energy source. At 1112, obtaining the spectral information includes concurrently detecting an excitation radiation and an emission radiation to generate a spectrum. At 1120, the method 1100 includes comparing at least one parameter associated with the obtained spectral information to one or more information subsets derived from partitioning spectral information associated with the biological subject. At 1122, comparing the at least one parameter associated with the obtained spectral information to the one or more information subsets derived from partitioning the spectral information includes comparing the at least one parameter associated with the obtained spectral information to one or more information subsets derived from grouping the spectral information into one or more information subsets using at least one of a Spectral Clustering protocol or a Spectral Learning protocol. At 1124, comparing the at least one parameter associated with the obtained spectral information to the one or more information subsets derived from partitioning spectral information includes comparing the at least one parameter associated with the obtained spectral information to one or more information subsets derived from grouping the spectral information into one or more information subsets using at least one of a Fuzzy C-Means Clustering protocol, a Graph-Theoretic protocol, a Hierarchical Clustering protocol, a K-Means Clustering protocol, a Locality-Sensitive Hashing protocol, a Mixture of Gaussians protocol, a Model-Based Clustering protocol, a Partitional protocol, a Spectral Clustering protocol, a Cluster-Weighted Modeling protocol, an Expectations-Maximization protocol, a Principal Components Analysis protocol, or a Spectral Learning protocol. At 1130, the method 1100 includes generating a response based on the comparison of the at least one parameter associated with the obtained spectral information to the one or more information subsets derived from partitioning spectral information associated with the biological subject. At 1132, generating the response includes generating at least one of information associated with a statistical probability, a local cluster density, a deviation from a target cluster distance, a distance from a cluster centroid, an euclidina distance, a probability density. At 1134, generating the response includes automatically updating at least one parameter associated with a spectral tissue model. At 1136, generating the response includes performing a real-time update of at least one parameter associated with a spectral blood clotting model associated with the biological subject.

In an embodiment, a computer program product includes one or more signal-bearing media containing computer instructions which, when run on a computing device, cause the computing device to implement a method 1200.

Figure 12:
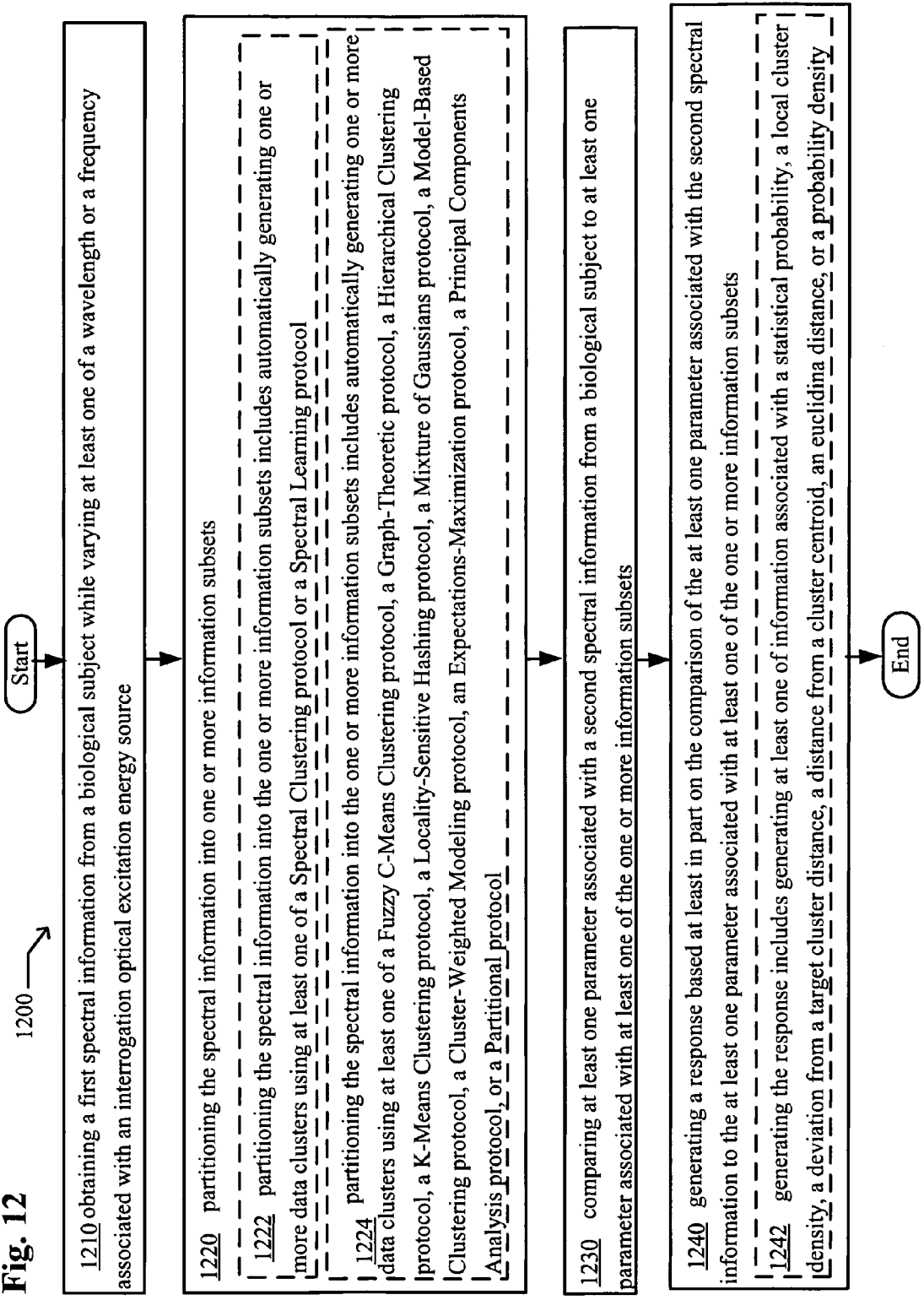
FIG. 12 is a flow diagram of a method according to one illustrated embodiment.

As show in FIG. 12, at 1210, the method 1200 includes obtaining a first spectral information from a biological subject while varying at least one of a wavelength or a frequency associated with an interrogation optical excitation energy source. At 1220, the method 1200 includes partitioning the spectral information into one or more information subsets. At 1222, partitioning the spectral information into the one or more information subsets includes automatically generating one or more data clusters using at least one of a Spectral Clustering protocol or a Spectral Learning protocol. At 1224, partitioning the spectral information into the one or more information subsets includes automatically generating one or more data clusters using at least one of a Fuzzy C-Means Clustering protocol, a Graph-Theoretic protocol, a Hierarchical Clustering protocol, a K-Means Clustering protocol, a Locality-Sensitive Hashing protocol, a Mixture of Gaussians protocol, a Model-Based Clustering protocol, a Cluster-Weighted Modeling protocol, an Expectations-Maximization protocol, a Principal Components Analysis protocol, or a Partitional protocol. At 1230, the method 1200 includes comparing at least one parameter associated with a second spectral information from a biological subject to at least one parameter associated with at least one of the one or more information subsets. At 1240, the method 1200 may include generating a response based at least in part on the comparison of the at least one parameter associated with the second spectral information to the at least one parameter associated with at least one of the one or more information subsets. At 1242, generating the response includes generating at least one of information associated with a statistical probability, a local cluster density, a deviation from a target cluster distance, a distance from a cluster centroid, an euclidina distance, or a probability density.

Figure 13B:
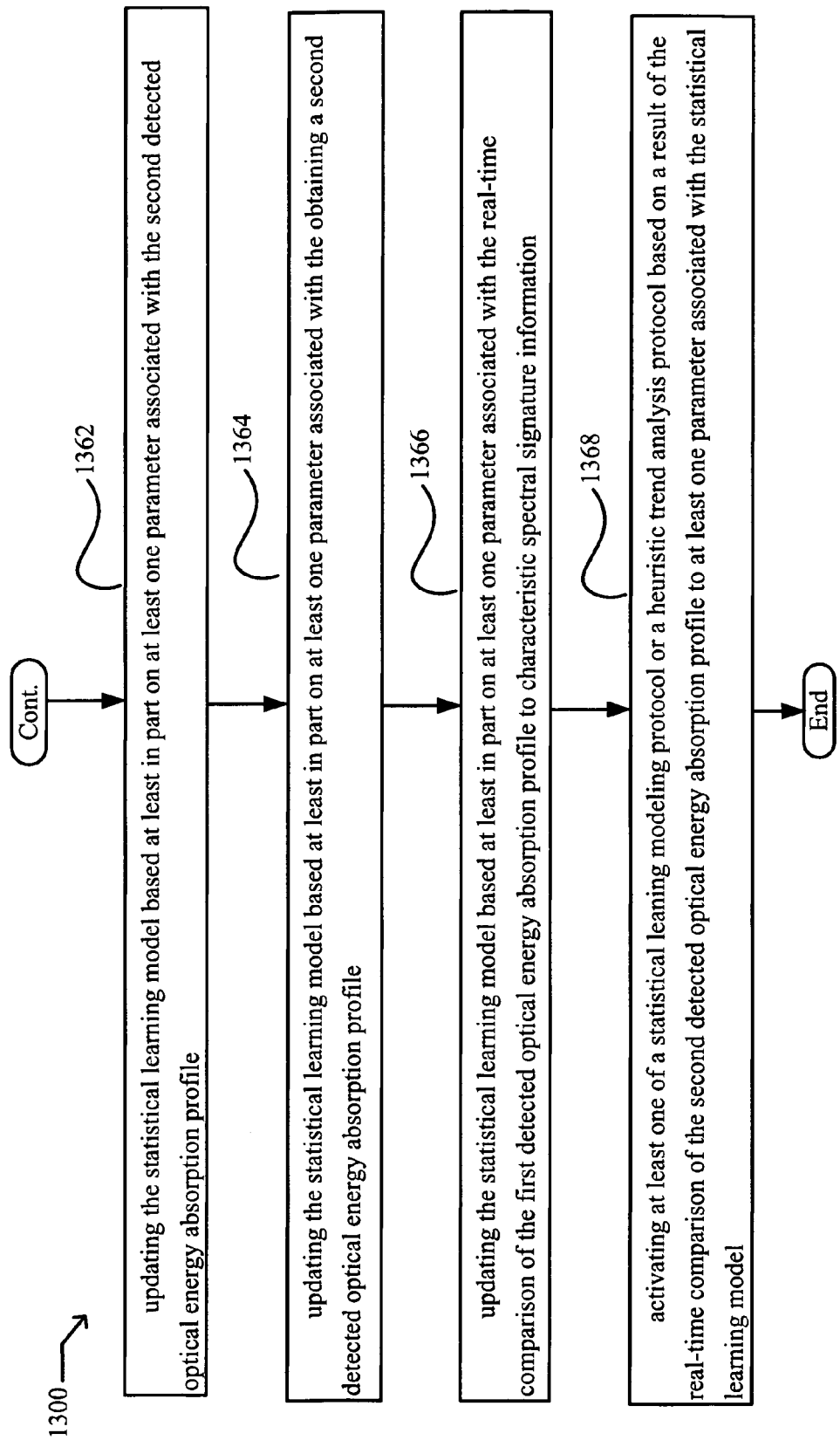

FIGS. 13A and 13B show an example of a method 1300. At 1310, the method 1300 includes performing a real-time comparison of a first detected optical energy absorption profile of a portion of a tissue within a biological subject to characteristic spectral signature information, the detected optical energy absorption profile including at least one of an emitted optical energy or a remitted optical energy. At 1320, the method 1300 includes determining whether an embolic event has occurred. At 1330, the method 1300 includes obtaining a second detected optical energy absorption profile of the portion of a tissue within a biological subject. At 1340, the method 1300 includes performing a real-time comparison of the second detected optical energy absorption profile to a statistical learning model associated with the biological subject. At 1350, the method 1300 includes determining whether an embolic event has occurred. At 1360, the method 1300 includes updating at least one parameter associated with the statistical learning model based at least in part on at least one parameter associated with the first detected optical energy absorption profile. At 1362, the method 1300 may include updating the statistical learning model based at least in part on at least one parameter associated with the second detected optical energy absorption profile. At 1364, the method 1300 may include updating the statistical learning model based at least in part on at least one parameter associated with the obtaining a second detected optical energy absorption profile. At 1366, the method 1300 may include updating the statistical learning model based at least in part on at least one parameter associated with the real-time comparison of the first detected optical energy absorption profile to characteristic spectral signature information. At 1368, the method 1300 may include activating at least one of a statistical leaning modeling protocol or a heuristic trend analysis protocol based on a result of the real-time comparison of the second detected optical energy absorption profile to at least one parameter associated with the statistical learning model.

In an embodiment, a computer program product includes one or more signal-bearing media containing computer instructions which, when run on a computing device, cause the computing device to implement a method 1400.

As show in FIG. 14, at 1410, the method 1400 includes obtaining a first spectral information from a biological subject while varying at least one of a wavelength or a frequency associated with an interrogation optical excitation energy source. At 1420, the method 1400 includes partitioning the spectral information into one or more information subsets. At 1422, partitioning the spectral information into the one or more information subsets includes grouping the spectral information into one or more information subsets using a clustering protocol. At 1424, partitioning the spectral information into the one or more information subsets includes grouping the spectral information into one or more information subsets using at least one of a Spectral Clustering protocol or a Spectral Learning protocol. At 1426, partitioning the spectral information into the one or more information subsets includes grouping the spectral information into one or more information subsets using at least one of a Fuzzy C-Means Clustering protocol, a Graph-Theoretic protocol, a Hierarchical Clustering protocol, a K-Means Clustering protocol, a Locality-Sensitive Hashing protocol, a Mixture of Gaussians protocol, a Model-Based Clustering protocol, a Cluster-Weighted Modeling protocol, an Expectations-Maximization protocol, a Principal Components Analysis protocol, or a Partitional protocol. At 1430, the method 1400 includes comparing at least one parameter associated with a second spectral information from a biological subject associated to at least one parameter associated with at least one of the one or more information subsets. At 1440, the method 1400 may include generating a response based on the comparison of the at least one parameter associated with the second spectral information to the at least one parameter associated with at least one of the one or more information subsets. At 1450, the method 1400 may include performing a real-time update of at least one parameter associated with a spectral blood vessel occlusion model associated with the biological subject.

Figure 15:
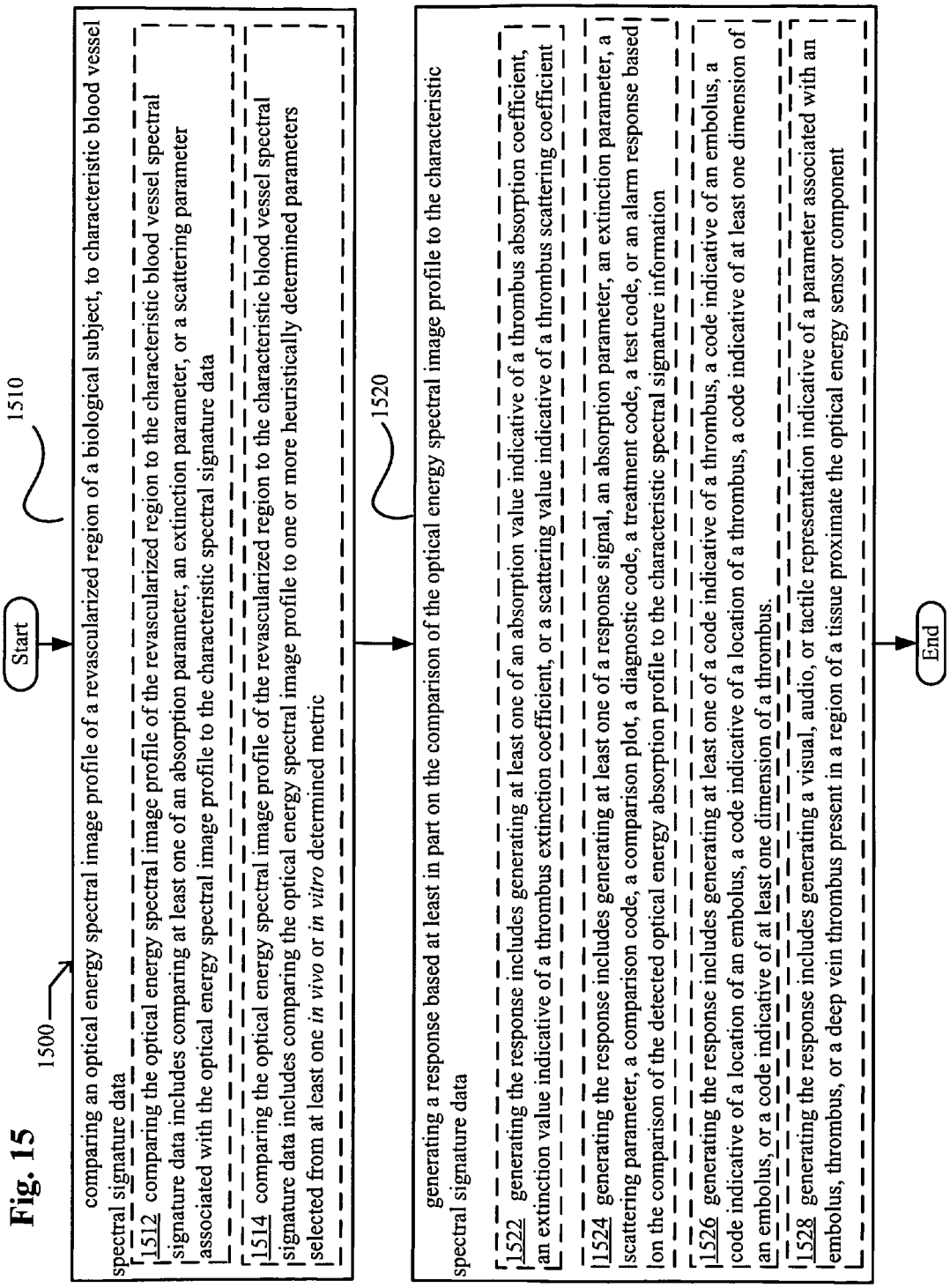
FIG. 15 is a flow diagram of a method according to one illustrated embodiment.

FIG. 15 shows an example of a method 1500. At 1510, the method 1500 includes comparing an optical energy spectral image profile of a revascularized region of a biological subject to characteristic blood vessel spectral signature data. At 1512, comparing the optical energy spectral image profile of the revascularized region to the characteristic blood vessel spectral signature data includes comparing at least one of an absorption parameter, an extinction parameter, or a scattering parameter associated with the optical energy spectral image profile to the characteristic spectral signature data. At 1514, comparing the optical energy spectral image profile of the revascularized region to the characteristic blood vessel spectral signature data includes comparing the optical energy spectral image profile to one or more heuristically determined parameters selected from at least one in vivo or in vitro determined metric.

At 1520, the method 1500 includes generating a response based at least in part on the comparison of the optical energy spectral image profile to the characteristic spectral signature data. At 1522, generating the response includes generating at least one of an absorption value indicative of a thrombus absorption coefficient, an extinction value indicative of a thrombus extinction coefficient, or a scattering value indicative of a thrombus scattering coefficient. At 1524, generating the response includes generating at least one of a response signal, an absorption parameter, an extinction parameter, a scattering parameter, a comparison code, a comparison plot, a diagnostic code, a treatment code, a test code, or an alarm response based on the comparison of the detected optical energy absorption profile to the characteristic spectral signature information. At 1526, generating the response includes generating at least one of a code indicative of a thrombus, a code indicative of an embolus, a code indicative of a location of an embolus, a code indicative of a location of a thrombus, a code indicative of at least one dimension of an embolus, or a code indicative of at least one dimension of a thrombus. At 1528, generating the response includes generating a visual, audio, or tactile representation indicative of a parameter associated with an embolus, thrombus, or a deep vein thrombus present in a region of a tissue proximate the optical energy sensor component.

Figure 16A:
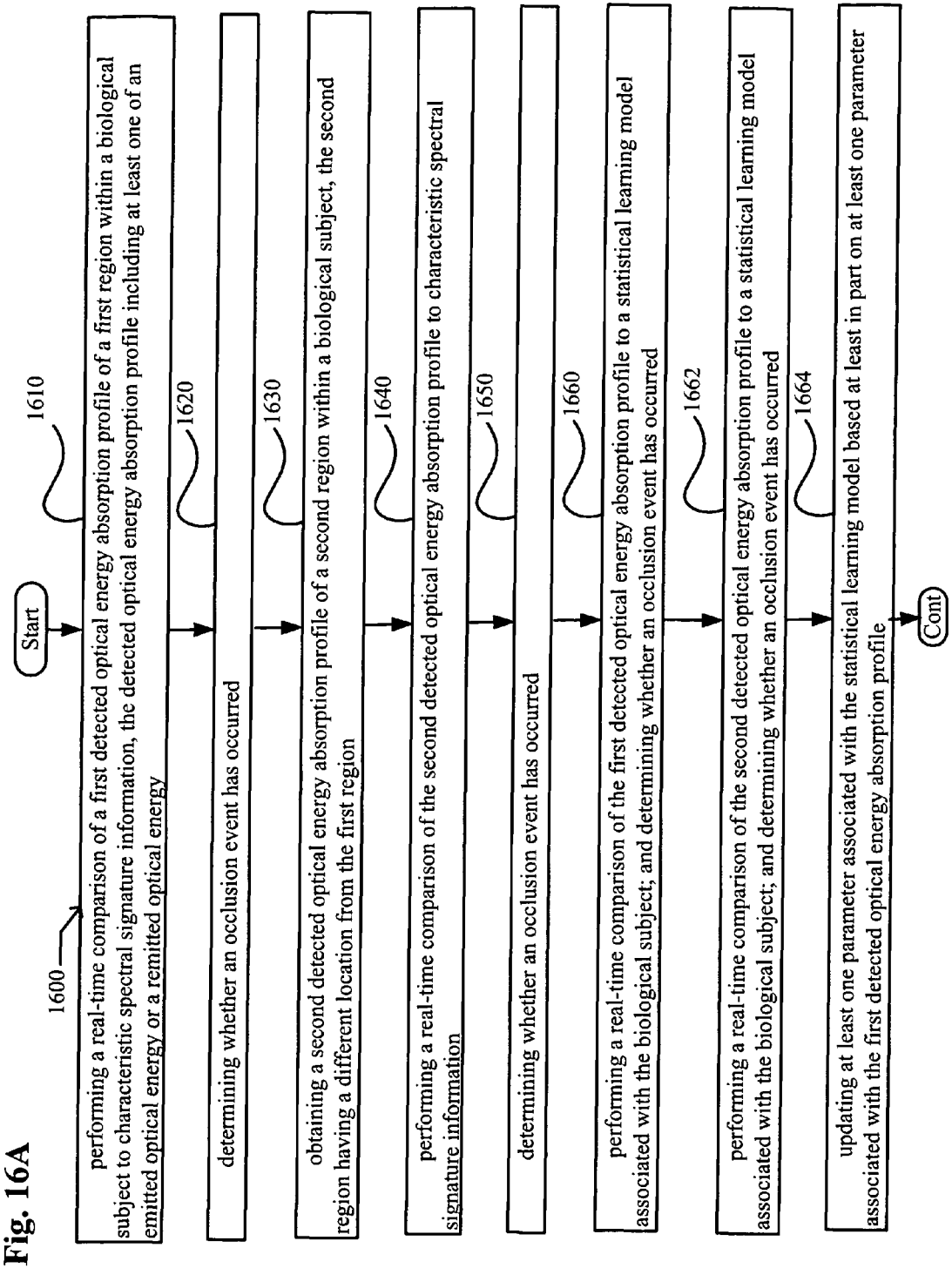
FIGS. 16A and 16B are flow diagrams of a method according to one illustrated embodiment.
Figure 16B:
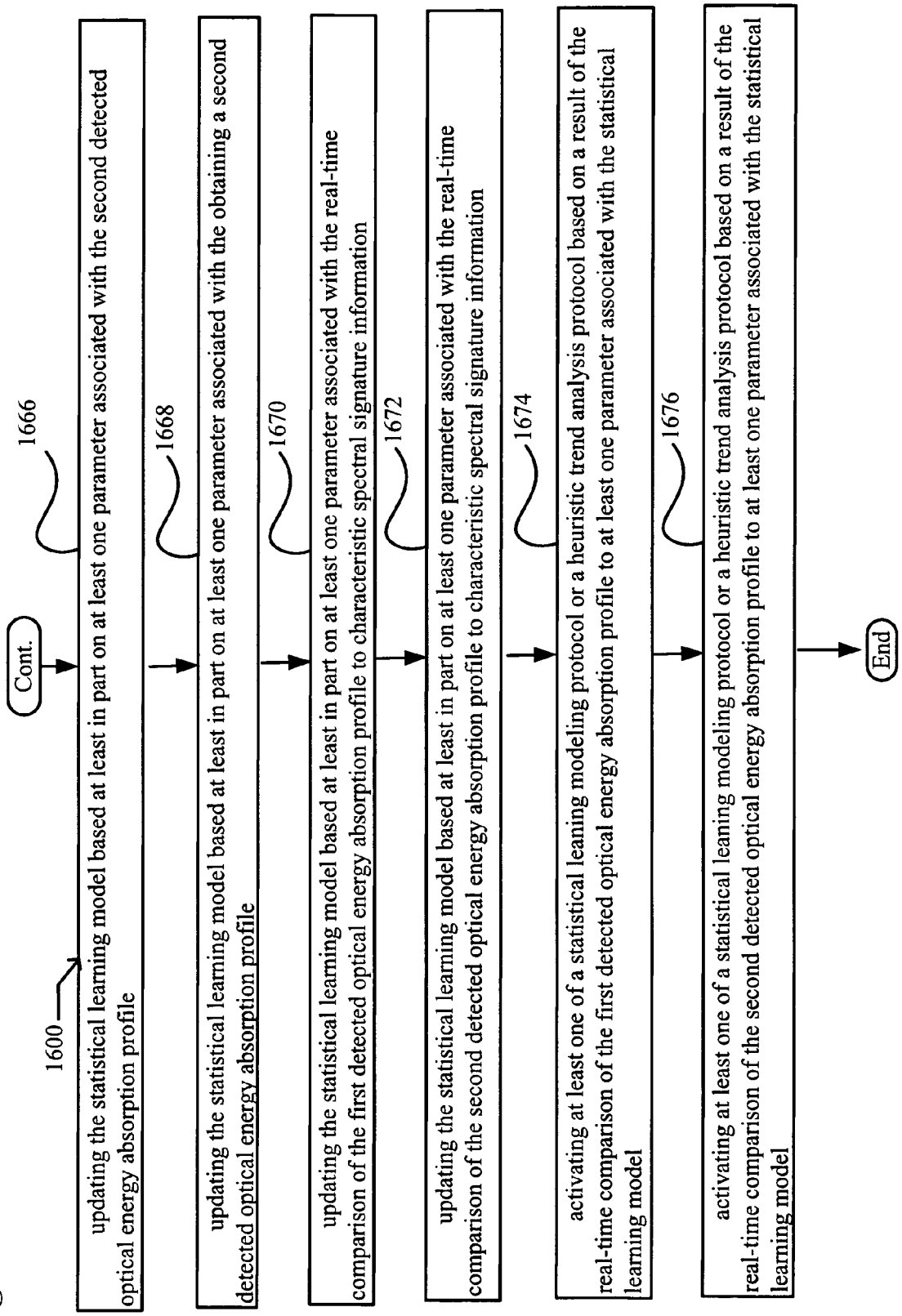

FIGS. 16A and 16B show an example of a method 1600. At 1610, the method 1600 includes performing a real-time comparison of a first detected optical energy absorption profile of a first region within a biological subject to characteristic spectral signature information, the detected optical energy absorption profile including at least one of an emitted optical energy or a remitted optical energy. At 1620, the method 1600 includes determining whether an occlusion event has occurred. At 1630, the method 1600 includes obtaining a second detected optical energy absorption profile of a second region within a biological subject. In an embodiment, the second region has a different location from the first region. At 1640, the method 1600 includes performing a real-time comparison of the second detected optical energy absorption profile to characteristic spectral signature information. At 1650, the method 1600 includes determining whether an occlusion event has occurred.

At 1660, the method 1600 may further include performing a real-time comparison of the first detected optical energy absorption profile to a statistical learning model associated with the biological subject, and determining whether an occlusion event has occurred. At 1662, the method 1600 may further include performing a real-time comparison of the second detected optical energy absorption profile to a statistical learning model associated with the biological subject, and determining whether an occlusion event has occurred. At 1664, the method 1600 may further include updating at least one parameter associated with the statistical learning model based at least in part on at least one parameter associated with the first detected optical energy absorption profile. At 1666, the method 1600 may further include updating the statistical learning model based at least in part on at least one parameter associated with the second detected optical energy absorption profile. At 1668, the method 1600 may further include updating the statistical learning model based at least in part on at least one parameter associated with the obtaining a second detected optical energy absorption profile. At 1670, the method 1600 may further include updating the statistical learning model based at least in part on at least one parameter associated with the real-time comparison of the first detected optical energy absorption profile to characteristic spectral signature information. At 1672, the method 1600 may further include updating the statistical learning model based at least in part on at least one parameter associated with the real-time comparison of the second detected optical energy absorption profile to characteristic spectral signature information. At 1674, the method 1600 may further include activating at least one of a statistical leaning modeling protocol or a heuristic trend analysis protocol based on a result of the real-time comparison of the first detected optical energy absorption profile to at least one parameter associated with the statistical learning model. At 1676, the method 1600 may further include activating at least one of a statistical leaning modeling protocol or a heuristic trend analysis protocol based on a result of the real-time comparison of the second detected optical energy absorption profile to at least one parameter associated with the statistical learning model.

Figure 17:
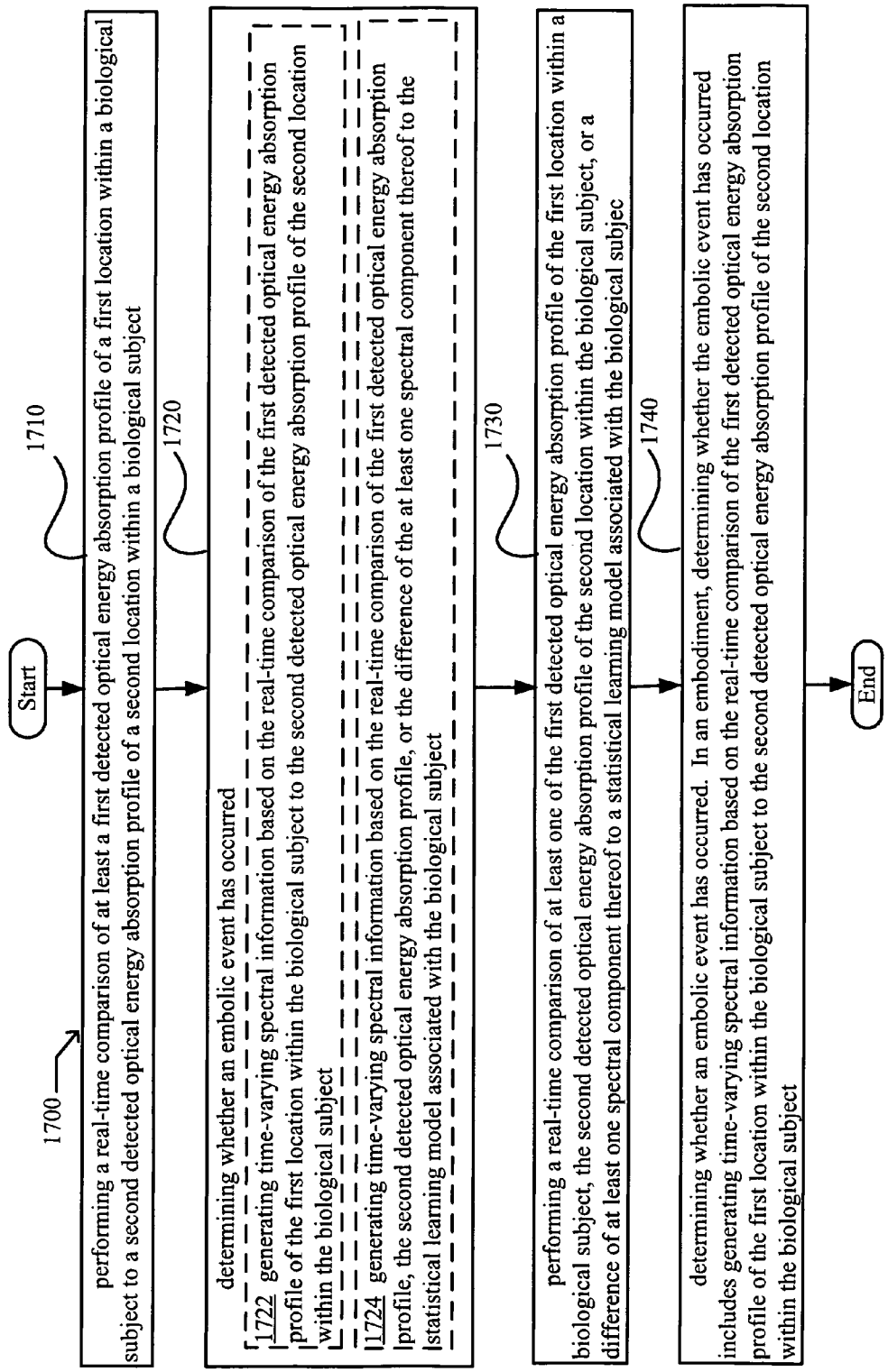
FIG. 17 is a flow diagram of a method according to one illustrated embodiment.

FIG. 17 shows an example of a method 1700. At 1710, the method 1700 includes performing a real-time comparison of at least a first detected optical energy absorption profile of a first location within a biological subject to a second detected optical energy absorption profile of a second location within a biological subject. At 1720, the method 1700 includes determining whether an embolic event has occurred. At 1722, determining whether the embolic event has occurred includes generating time-varying spectral information based on the real-time comparison of the first detected optical energy absorption profile of the first location within the biological subject to the second detected optical energy absorption profile of the second location within the biological subject. At 1724, determining whether the embolic event has occurred includes generating time-varying spectral information based on the real-time comparison of the first detected optical energy absorption profile, the second detected optical energy absorption profile, or the difference of the at least one spectral component thereof to the statistical learning model associated with the biological subject. At 1730, the method 1700 includes performing a real-time comparison of at least one of the first detected optical energy absorption profile of the first location within a biological subject, the second detected optical energy absorption profile of the second location within the biological subject, or a difference of at least one spectral component thereof to a statistical learning model associated with the biological subject. At 1740, the method 1700 includes determining whether an embolic event has occurred. In an embodiment, determining whether the embolic event has occurred includes generating time-varying spectral information based on the real-time comparison of the first detected optical energy absorption profile of the first location within the biological subject to the second detected optical energy absorption profile of the second location within the biological subject. In an embodiment, determining whether the embolic event has occurred includes generating time-varying spectral information based on the real-time comparison of the first detected optical energy absorption profile, the second detected optical energy absorption profile, or the difference of the at least one spectral component thereof to the statistical learning model associated with the biological subject.

Figure 18:
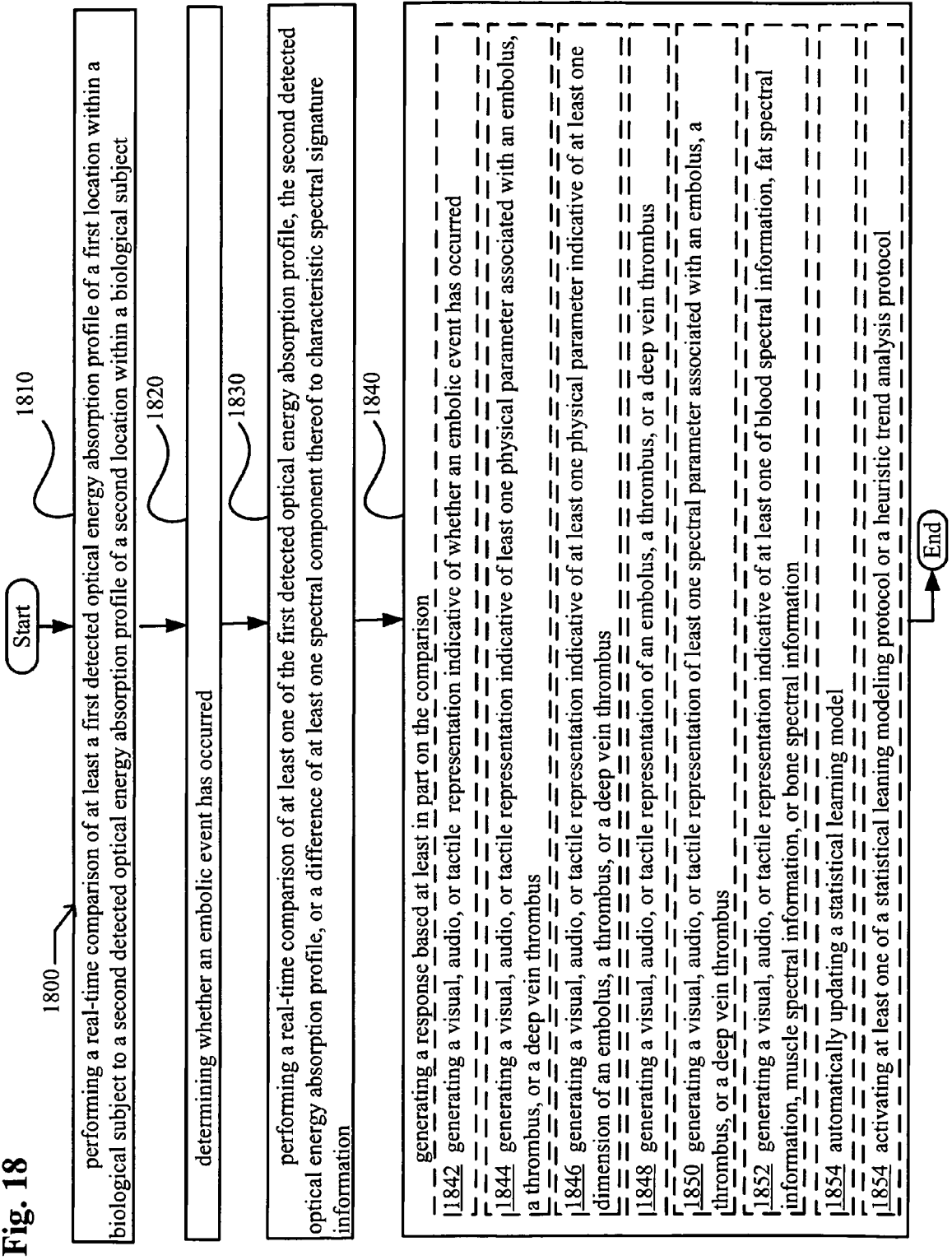
FIG. 18 is a flow diagram of a method according to one illustrated embodiment.

FIG. 18 shows an example of a method 1800. At 1810, the method 1800 includes performing a real-time comparison of at least a first detected optical energy absorption profile of a first location within a biological subject to a second detected optical energy absorption profile of a second location within a biological subject.

At 1820, the method 1800 includes determining whether an embolic event has occurred. At 1830, the method 1800 includes performing a real-time comparison of at least one of the first detected optical energy absorption profile, the second detected optical energy absorption profile, or a difference of at least one spectral component thereof to characteristic spectral signature information. At 1840, the method 1800 includes generating a response based at least in part on the comparison. At 1842, generating the response includes generating a visual, audio, or tactile representation indicative of whether an embolic event has occurred. At 1844, generating the response includes generating a visual, audio, or tactile representation indicative of at least one physical parameter associated with an embolus, a thrombus, or a deep vein thrombus. At 1846, generating the response includes generating a visual, audio, or tactile representation indicative of at least one physical parameter indicative of at least one dimension of an embolus, a thrombus, or a deep vein thrombus. At 1848, generating the response includes generating a visual, audio, or tactile representation of an embolus, a thrombus, or a deep vein thrombus. At 1850, generating the response includes generating a visual, audio, or tactile representation of at least one spectral parameter associated with an embolus, a thrombus, or a deep vein thrombus. At 1852, generating the response includes generating a visual, audio, or tactile representation indicative of at least one of blood spectral information, fat spectral information, muscle spectral information, or bone spectral information. At 1854, generating the response includes automatically updating a statistical learning model. At 1856, generating the response includes activating at least one of a statistical leaning modeling protocol or a heuristic trend analysis protocol.

Figure 19:
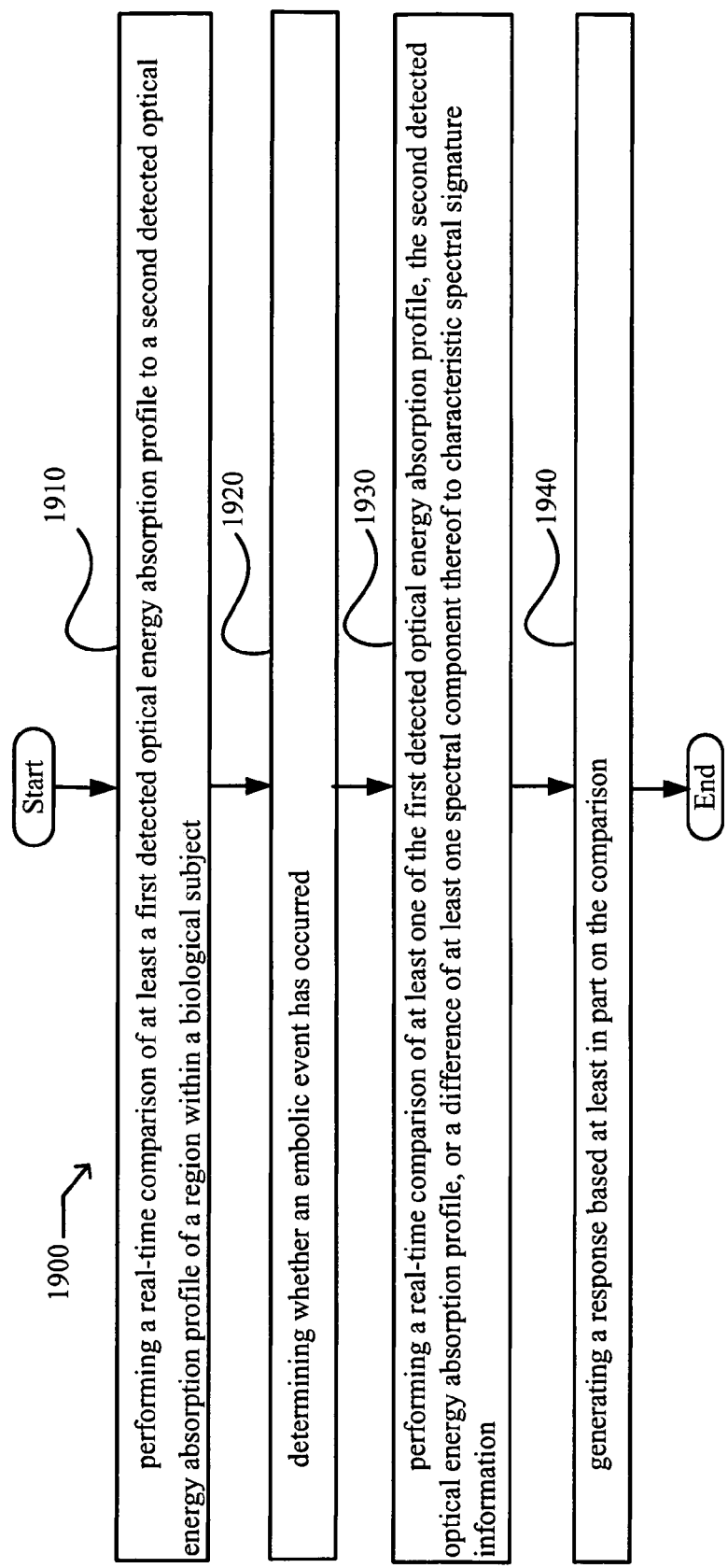
FIG. 19 is a flow diagram of a method according to one illustrated embodiment.

FIG. 19 shows an example of a method 1900. At 1910, the method 1900 includes performing a real-time comparison of at least a first detected optical energy absorption profile to a second detected optical energy absorption profile of a region within a biological subject. At 1920, the method 1900 includes determining whether an embolic event has occurred. At 1930, the method 1900 includes performing a real-time comparison of at least one of the first detected optical energy absorption profile, the second detected optical energy absorption profile, or a difference of at least one spectral component thereof to characteristic spectral signature information. At 1940, the method 1900 includes generating a response based at least in part on the comparison.

In an embodiment, an article of manufacture includes, but is not limited to, a computer-readable memory medium including characteristic spectral signature information configured as a physical data structure 168 for use in analyzing or modeling a detected optical energy spectral image profile for a biological subject. In an embodiment, the data structure 168 includes a characteristic spectral signature data section having at least one machine-readable storage medium. In an embodiment, the at least one machine-readable storage medium includes instructions encoded thereon for enabling a processor to perform the method of determining an optical energy spectral image profile of a region within a biological subject, and comparing a value associated with the determined optical energy spectral image profile to optical energy spectral image information. In an embodiment, the at least one machine-readable storage medium includes, but is not limited to, instructions encoded thereon for enabling a processor to perform the method of generating a response based on the comparison.

In an embodiment, the generated response includes at least one of a response signal, a comparison code, a comparison plot, a diagnostic code, a treatment code, a test code, or an alarm response. In an embodiment, the generated response includes at least one of a code indicative of a myocardial infarction, a code indicative of a stroke, a code indicative of a thrombus, or a code indicative of an embolus. In an embodiment, the generated response includes at least one of a code indicative of a subdural hematoma, a code indicative of a location of a subdural hematoma, a code indicative of an epidural hematoma, a code indicative of a location of an epidural hematoma, a code indicative of a location of an embolus, or a code indicative of at least one dimension of an embolus.

Example 1

Blood for in Vitro Spectral Analysis

Whole blood for in vitro spectral analysis can be obtained from one of several sources. Fresh whole blood from a variety of non-human animal species is available from commercial sources (from, e.g., Hemostat, Dixon, Calif.; Pel-Freez Biologicals, Roger, Ark.). Alternatively, fresh whole blood is drawn from an animal using standard methods such as those described by Hoff for drawing blood from small laboratory rodents (Hoff *Lab Animal* 29:47-53, 2002, which is incorporated herein by reference). Whole blood from a human subject may also be used for in vitro spectral analysis. Blood is drawn using, for example, but not limited to, standard phlebotomy methods by a trained technician.

The whole blood is treated with an anticoagulant to prevent premature formation of blood clots during processing and storage. Examples of anticoagulants include, but are not limited to, Alsevers, sodium citrate, heparin, ethylenediaminetetraacetic acid (EDTA), citrate phosphate dextrose adenine (CPDA), citrate phosphate dextrose (CPD), acid citrate dextrose (ACD), or sodium oxylate. The whole blood is drawn from a vein or an artery directly into a syringe containing an anticoagulant. Alternatively, the blood is drawn from a vein or an artery and subsequently mixed with an anticoagulant. Blood is drawn into either BD Vacutainer Glass or Plus Plastic Citrate Tubes (BD, Franklin Lakes, N.J.) containing 3.2% citrate with a vacuum designed to collect blood in a 9:1 ratio of blood to citrate. Alternatively, the blood is drawn and processed in the absence of an anticoagulant.

In some circumstances, blood of a specific hematocrit (packed cell volume) is used. This is achieved by separating and reconstituting blood components. Whole blood is centrifuged to separate red blood cells from the plasma. The concentrated red blood cells are washed several times in a buffered saline solution to remove white blood cells and other impurities. Blood samples with a specific hematocrit are obtained by reconstituting a specific volume or percentage of red blood cells with the separated plasma. Normal hematocrit levels for humans, for example, range from about 37% to about 54% depending upon gender.

Example 2

In Vitro Spectral Analysis of Whole Blood

Blood for in vitro spectral analysis is obtained fresh from a commercial source (sheep blood, e.g., from, e.g., Hemostat, Dixon, Calif.). Sodium citrate may be present in the blood as an anticoagulant to prevent premature clot formation. Sodium citrate chelates can free calcium ions that are necessary for normal clot formation.

An appropriate volume of whole blood is transferred to a quartz cuvette for analysis. The cuvette holder may include a heating element or water jacket to maintain the cuvette at physiological temperature during the clotting procedure. The temperature setting may range from about 36° C. to about 40° C. depending upon the source of the blood. In the case of sheep blood, the temperature is set at 39.4° C., the normal body temperature for sheep. The cuvette can also include a component for agitating the blood such as a small magnetic stir bar. Alternatively, the blood sample is injected into the cuvette under a layer of mineral oil to prevent gas exchange with the atmosphere. Alternatively, blood may be fully oxygenated by stirring for 20 minutes in an open container (Steenbergen, et al., *J. Opt. Soc. Am. A* 16:2959-2967, 1999, which is incorporated herein by reference). The level of oxygen in the blood may be assessed in vitro using a standard blood gas analyzer.

A clotting agent is added to the whole blood in the cuvette to initiate clotting. Examples of agents that may be used to induce blood clot formation include, but are not limited to, adenosine diphosphate (ADP), epinephrine, collagen, thrombin, or calcium chloride. Whole blood treated with sodium citrate, for example, is recalcified with calcium chloride (0.4%, 1:3 vol/vol, e.g.) to initiate clot formation.

In vitro spectral analysis may be performed before and during blood clot formation at various wavelengths including ultraviolet, visible, near-infrared, or infrared, or combinations thereof. For example, a BECKMAN DU640 UV-VIS- NIR scanning spectrophotometer may be used for in vitro spectral analysis of blood clot formation in wavelengths ranging from 190 nm to 1100 nm. Multiple spectra are captured prior to addition of the clotting agents and at various time points thereafter over the course of clot formation. For example, spectra over a broad wavelength range may be captured every 1-30 seconds over the course of about 20 to 30 minutes.

Reflectance spectroscopy in the UV/VIS wavelength range may be used for in vitro spectral analysis of blood clot formation (Greco Arch. Pathol. *Lab. Med.* 128:173-180, 2004, which is incorporated herein by reference). Alternatively, light reflected or scattered by the blood sample is detected during the clotting process. The blood sample is illuminated using either a xenon arc lamp or a tungsten halogen lamp and reflected light of appropriate angle is measured by the detector. A clotting agent is added to initiate clot formation. The resulting spectra are captured using, for example, a charge-coupled device array at various wavelengths ranging from about 200 to about 875 nm. Multiple spectra are generated over the time-course of blood clot formation.

To establish a baseline spectrum for time course measurements, the initial state of blood in the cuvette is estimated by linear extrapolation from the first five time points at each wavelength and used as reference. Alternatively, a baseline spectrum may be established by generating one or more spectra of the blood prior to the addition of the clotting agent. The baseline may be used to normalize the spectral data collected during clot formation. Alternatively, the spectral data may be normalized against a diffuse white standard such as that generated by an opaque aqueous solution of barium sulfate (50% wt/wt).

Alternatively, blood clot formation may be monitored using near infrared spectroscopy (see, e.g., WIPO Publication No. WO 2007/067952 A2, which is incorporated herein by reference). Near-infrared (NIR) spectral analysis in the wavelength range from about 650 nm to about 1100 nm may be performed using the same instrumentation as that used for UV/VIS spectroscopy. Alternatively, an NIR spectrometer may be used for spectral analysis in the 900 to 1700 nm wavelength range. A baseline spectrum of the whole blood is performed in the NIR wavelength range. Having established the baseline spectrum, a clotting agent is added to induce clot formation. Additional spectra are captured over the course of clot formation every 30 seconds over the course of about 20 to 30 minutes. The spectral signature of the forming blood clot may be fitted to a time-domain analysis using least mean square and regression analysis methods.

Example 3

In Vitro Analysis of Blood Clot Formation Under Conditions of Flow

Spectral analysis of blood clot formation may be performed in vitro under conditions of flow that simulate normal blood flow. Under some conditions, blood flowing in a vessel may be stimulated to form a blood clot in response to injury to the surrounding blood vessel. Injury to a surrounding blood vessel may cause loss of integrity of the endothelial barrier and exposure of the blood to the underlying connective tissue. In vitro models may be used to simulate blood vessel injury and induce clot formation. A spectral signature of clot formation may be captured under these conditions.

Blood clot formation may be induced in vitro by perfusing blood over a denuded and immobilized artery from which endothelial cells have been removed (see, e.g., Zwanginga, et al., *J. Clin. Invest.* 93:204-211, 1994, which is incorporated herein by reference). Umbilical artery segments from an umbilical cord are deendothelialized by a brief exposure to air and mounted in a perfusion chamber. Alternatively, the artery may be deendothelialized by gentle scrapping of the lumen surface. Whole blood treated with sodium citrate is perfused for two minutes at 37° C. over everted arterial segments to measure platelet adherence and thrombus formation on the subendothelial surface. Alternatively, whole blood may be perfused over noneverted arterial segments to measure platelet interaction with the thrombogenic adventitial surface, which simulates the physiological response to deep arterial injury. Perfusions are performed at a flow rate of 30 mL/min creating a wall shear rate ($2600$ $s^{-1}$) that closely simulates physiological conditions in the microvasculature and pathological conditions in stenosed arteries.

Alternatively, blood clot formation may be performed by perfusing whole blood over a collagen coated surface or other thrombogenic surface. For example, blood may be perfused through a perfusion chamber coated with a thrombogenic agent such as collagen (e.g., Type I bovine collagen or fibrillar equine collagen). Interaction of the blood with the collagen initiates blood clot formation. The perfusion chamber is placed on a heated microscope stage for analysis. A peristaltic pump is used to perfuse the blood through the chamber as described above.

Blood clot formation may be monitored under a microscope using light microscopy or near-infrared microscopy. Alternatively, a fluorescent probe may be added to the perfused blood that accumulates at the site of clot formation and is visualized by fluorescence microscopy. Alternatively, spectroscopy using a fiber optic probe, for example, may be used to capture a spectral signature of blood clot formation in the perfusion chamber.

Example 5

In Vitro Analysis of Blood Clot Formation Using Ultrasound

Blood clot formation may be monitored in vitro using ultrasound backscattering (see, e.g., Huang, et al., *Ultrasound Med. Biol.* 31:1567-1573, 2005, which is incorporated herein by reference). Fresh blood can either be purchased or drawn from an animal as described above. An anticoagulant may be added to the blood sample, e.g., 15% acid-citrate-dextrose. The blood sample is placed into a container with an acoustic window covered with a material capable of transmission and reception of ultrasound energy. The container is placed into a water bath equipped with a thermocirculator to keep the bath at a constant temperature. A wideband focused transducer with a center frequency of 10 MHz, −6 dB band width of 7 MHz, an F-number of 1.6, a focal length of 20 mm and a diameter of 12.7 mm is submerged into the water bath. A pulser/receiver may be used to drive that transducer. The received radio-frequency (RF) signals backscattered from blood are amplified, filtered and digitized. RF signals are recorded from the blood sample at a temporal resolution of 1 A line per second. After about 3-5 minutes, a blood clotting agent, e.g., 0.2 M calcium chloride is added to the blood to induce clot formation. RF signals are recorded for about 30-50 minutes throughout clot formation.

A flow model system may be devised for measuring the changes in ultrasound backscatter of blood during blood clot formation under the conditions of flow (see, e.g., Huang & Wang, *IEEE Trans. Biomed. Eng.* 54:2223-2230, 2007, which is incorporated herein by reference). In this system, a reservoir of about 30 milliliters of blood is circulated through a conduit composed of polyurethane tubing. The circulating blood in the conduit passes through a water bath in which an ultrasound transducer has been submerged for transmitting and receiving ultrasonic pulses. The blood flow in the system is regulated by a peristaltic pump and valves to produce shear rates ranging from about 10 s-1 to about 100 s-1. A coagulation agent such as calcium chloride may be added to a final concentration of 0.05 M to induce blood clot formation. Data in the form of ultrasonic radio-frequency signals are acquired during clot formation over a total of 20 minutes at a temporal resolution of 50 A-lines per second.

Example 6

In Vivo Analysis of Blood Clot Formation Using Dynamic Light Scattering

A spectral signature of blood clot formation may be captured in vivo using light scattering. Alternatively, the formation of a blood clot is correlated with changes in the motion and flow of red blood cells in the affected area of the clot.

The analysis of changes in light scattering due to clot formation may be measured using intravital microscopy in combination with laser Doppler and laser speckle techniques. Intravital microscopy may be performed by exposing the arteries of the mesentery and placing them on a microscopy stage for illumination. Alternatively, non-invasive intravital microscopy may be performed by studying vessels that are close to the surface of the skin. For example, blood vessels in the thin ears of some animal species such as mice have been used for intravital microscopy. Under anesthesia, a mouse is positioned on the microscope stage such that the ear is fully illuminated with a laser (e.g., red diode laser 670 nm, 10 mW) coupled to a diffuser. The illuminated area is imaged using a zoom stereo microscope and a charge-coupled device (CCD) camera connected to a computer. Images may be captured every 0.1 to 5 seconds.

Clot formation in the blood vessels may be initiated by any of a number of technologies and methodologies including but not limited to crushing or clamping a vessel, electrical stimulation of a vessel, laser induced damage to a vessel, localized excitation of a photosensitizer, or local administration of a toxin such as ferris chloride. As an example, a short high intensity burst from a focused laser beam (e.g., green diode pumped solid state laser module 532 nm, 100 mW) may be used to induce vessel injury.

Light scattering imaging of the motion of red blood cells during clot formation is based on the temporal contrast of intensity fluctuations produced from laser speckles reflected from the imaged tissue. The laser speckle is an interference pattern produced by the light reflected or scattered from different parts of the illuminated surface and captured by the camera as a granular or speckled pattern. The moving red blood cells create a time-varying speckle pattern at each pixel of the image. The intensity variations may be used to calculate and mathematically map areas of blood vessels under flow and no-flow conditions (see, e.g., Kalchenko, et al., *J. Biomed. Optics* 15:052002, 2007, which is incorporated herein by reference).

Alternatively, the analysis of changes in light scattering due to clot formation may be measured using diffuse reflectance spectroscopy. Alternatively, a blood vessel is irradiated by a tungsten lamp through an optical fiber reflection probe containing an illumination fiber and multiple detection fibers for detection of the reflected signal (see, e.g., U.S. Pat. No. 7,430,455 B2, which is incorporated herein by reference). Reflection probes optimized for the UV/VIS (250-800 nm) or VIS/NIR (400-2100 nm), or a combination thereof are available from commercial sources (from, e.g., Ocean Optics, Dunedin, Fla.). The probe is placed in proximity to a blood vessel close to the surface of the skin. Multiple spectra are captured before and after initiation of clot formation.

Example 7

In Vivo Analysis of Blood clot Formation Using Near-Infrared Fluorescence Microscopy Blood clot formation may be monitored in vivo using near-infrared fluorescence microscopy. Alternatively, a fluorescent agent is incorporated into a component of the coagulation pathway and accumulates at the site of blood clot formation. For example, platelets may be isolated and labeled with a fluorescent agent. The labeled platelets are returned to the circulation where they can participate in clot formation. The formation of a blood clot may be monitored using fluorescence microscopy (see, e.g., Flaumenhaft, et al., Circ. 112: 84-93, 2007, which is incorporated herein by reference). The use of fluorescent dyes that fluoresce in the NIR wavelengths may be used to detect clot formation in deeper vessels through the skin.

Platelet-rich plasma is isolated from whole blood by centrifugation at approximately 200 g for about 20 minutes. Platelets is isolated from the plasma by additional centrifugation at approximately 1400 g for about 10 minutes in the presence of about 50 ng/ml prostaglandin $E_1$ and 10% (v/v) acid citrate/dextrose. The platelets is loaded with IR-786, a lipophilic, cationic, heptamethine indocyanine-type NIR fluorophore (from Sigma Aldrich, St. Louis, Mo.) by incubation of about 0.5 to 5 umol/L IR-786 with isolated platelets for 1 to 120 minutes at room temperature. The platelets is washed and returned to the anesthetized animal by intravenous infusion. Blood clot formation is induced in a surgically exposed blood vessel by localized administration of a solution of ferrous chloride (10-50%). Alternatively, blood clot formation is induced by embolic coil, intravascular stent or cutaneous incision. The accumulation of fluorescently labeled platelets at the site of clot formation may be monitored in the blood vessel using a surgical microscope equipped for NIR fluorescence microscopy, an example of which is described by De Grand & Frangioni, *Technol. Cancer Res. Treat.* 2:553-562, 2003, which is incorporated herein by reference. Alternatively, clot formation may be monitored using an inverted epifluorescence microscope (e.g., Zeiss Axovert, Carl Zeiss MicroImaging, Inc., Thornwood, N.Y.) equipped with a CCD camera interfaced with a computer. Alternatively, blood clot formation may be monitored by NIR fluorescence using a fluorescent agent that is incorporated into the forming clot. For example, a small peptide mimetic of α2-antiplasmin is incorporated by factor XIIIa (FXIIIa) into forming blood clots and is monitored by intravital microscopy (see, e.g., Jaffer, et al., Circ. 110:170-176, 2004, which is incorporated herein by reference). An appropriate agent may be modified with a NIR fluorochrome such as Alexa Fluor 680C2 (from, Invitrogen, Carlsbad, Calif.) following the manufacturer's instructions. The fluorescent agent is infused into the animal and clot formation is initiated as described above. Serial images of clot formation in a blood vessel are captured using a CCD camera over 20-30 minutes.

Other commercially available fluorochromes for NIR fluorescence include but are not limited to, cyanine dyes such as Cy5, Cy5.5, and Cy7 (Amersham Biosciences, Piscataway, N.J., USA), as well as a variety of Alexa Fluor dyes including Alexa Fluor 633, Alexa Fluor 635, Alexa Fluor 647, Alexa Fluor 660, Alexa Fluor 700 and Alexa Fluor 750 (Invitrogen, Carlsbad, Calif., USA; see, e.g., U.S. Pat. App. No. 2005/0171434 A1). Additional fluorophores include IRD41 and IRD700 (LI-COR, Lincoln, Neb., USA), NIR-1 and IC5-OSu (Dejindo, Kumamotot, Japan), LaJolla Blue (Diatron, Miami, Fla., USA), FAR-Blue, FAR-Green One, and FAR-Green Two (Innosense, Giacosa, Italy), ADS 790-NS and ADS 821-NS (American Dye Source, Montreal, Calif.) and VivoTag 680 (VT680; VisEn Medical, Woburn, Mass., USA).

Example 8

In Vivo Analysis of Blood Clot Formation Using Near-Infrared Fluorescence Spectroscopy Blood clot formation may be monitored in vivo using near-infrared fluorescence spectroscopy. Platelets and other components associated with blood clot formation is labeled with a NIR fluorochrome as described above and administered to a subject. Blood clot formation is initiated in one or more blood vessels near the surface of the skin using one or more of the methods described herein. The formation of the blood clot in a specific vessel is monitored non-invasively using a fiber optic fluorescence probe (e.g., QF600-8-VIS/NIR 400-900 nm; Ocean Optics, FL) connected to a spectrofluorometer. Serial spectra of the blood vessel are captured before and after initiation of clot formation over the course of 20-30 minutes.

At least a portion of the devices and/or processes described herein is integrated into a data processing system. A data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact, many other architectures may be implemented that achieve the same functionality. In a conceptual sense, any arrangement of components to achieve the same functionality is effectively "associated" such that the desired functionality is achieved. Hence, any two components herein combined to achieve a particular functionality is seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably coupleable," to each other to achieve the desired functionality. Specific examples of operably coupleable include, but are not limited to, physically mateable and/or physically interacting components, and/or wirelessly interactable, and/or wirelessly interacting components, and/or logically interacting, and/or logically interactable components.

In an embodiment, one or more components may be referred to herein as "configured to," "configurable to," "operable/operative to," "adapted/adaptable," "able to," "conformable/conformed to," etc. Such terms (e.g., "configured to") can generally encompass active-state components and/or inactive-state components and/or standby-state components, unless context requires otherwise.

Although specific dependencies have been identified in the claims, it is to be noted that all possible combinations of the features of the claims are envisaged in the present application, and therefore the claims are to be interpreted to include all possible multiple dependencies.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by the reader that each function and/or operation within such block diagrams, flowcharts, or examples are implemented, individually and/or collectively, by a wide range of hardware, software, firmware, or virtually any combination thereof. Further, the use of "Start," "End" or "Stop" blocks in the block diagrams is not intended to indicate a limitation on the beginning or end of any functions in the diagram. Such flowcharts or diagrams may be incorporated into other flowcharts or diagrams where additional functions are performed before or after the functions shown in the diagrams of this application. In an embodiment, several portions of the subject matter described herein may be implemented via Application Specific Integrated Circuits (ASICs), Field Programmable Gate Arrays (FPGAs), digital signal processors (DSPs), or other integrated formats. However, some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the mechanisms of the subject matter described herein are capable of being distributed as a program product in a variety of forms, and that an illustrative embodiment of the subject matter described herein applies regardless of the particular type of signal-bearing medium used to actually carry out the distribution. Examples of a signal-bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

While particular aspects of the present subject matter described herein have been shown and described, it will be apparent to the reader that, based upon the teachings herein, changes and modifications may be made without departing from the subject matter described herein and its broader aspects and, therefore, the appended claims are to encompass within their scope all such changes and modifications as are within the true spirit and scope of the subject matter described herein. In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). Further, if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense of the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense of the convention (e.g., "a system having at least one of A, B, or C" would include but not be limited to systems that have A alone, B alone, C alone, A and B together, A and C together, B and C together, and/or A, B, and C together, etc.). Typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, the operations recited therein generally may be performed in any order. Also, although various operational flows are presented in a sequence(s), it should be understood that the various operations may be performed in orders other than those that are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

While various aspects and embodiments have been disclosed herein, other aspects and embodiments are contemplated. The various aspects and embodiments disclosed herein are for purposes of illustration and are not intended to be limiting, with the true scope and spirit being indicated by the following claims.

What is claimed is:

1. An occlusion monitoring device, comprising:
   an interrogation energy emitter component;
   a sensor component, the sensor component configured to detect at least one of an emitted energy or a remitted energy,
      determine at least one spatial dependence and at least one temporal dependence associated with an occlusion in an artery, a blood clot formation in a blood vessel, an embolus, or a blood clot formation in a deep vein within the biological subject under test,
      predict the onset of an obstruction in blood vessel, and
      generate a first response based on a detected at least one of the emitted energy or the remitted energy, the first response indicative of at least one physical parameter associated with the at least one spatial dependence and the at least one temporal dependence of the occlusion in an artery, the blood clot formation in a blood vessel, the embolus, or the blood clot formation in a deep vein within the biological subject under test; and
   one or more non-transitory computer-readable memory media having blood vessel spectral occlusion information configured as a data structure, the data structure including a spectral signature information section having at least one of
      embolus spectral information,
      arterial embolus spectral information,
      thrombus spectral information,
      deep vein thrombus spectral information, or
      blood component spectral information;
   the sensor component including one or more computing devices configured to determine the at least one spatial dependence and the at least one temporal dependence associated with the occlusion in an artery, the blood clot formation in a blood vessel, the embolus, or the blood clot formation in a deep vein within the biological subject under test based on the comparison of the detected emitted energy or a remitted energy and the blood vessel spectral occlusion information configured as the data structure.

2. The occlusion monitoring device of claim 1, wherein the interrogation energy emitter component is configured to deliver at least one of an electromagnetic interrogation energy, an electrical interrogation energy, an ultrasonic interrogation energy, or a thermal interrogation energy to at least one region within a biological subject.

3. The occlusion monitoring device of claim 1, wherein the interrogation energy emitter component is configured to deliver an electromagnetic interrogation energy to at least one region within a biological subject, the electromagnetic interrogation energy having at least a first peak emission wavelength ranging from about 600 nm to about 850 nm, and a second peak emission wavelength ranging from about 850 nm to about 1000 nm.

4. The occlusion monitoring device of claim 1, wherein the interrogation energy emitter component is configured to deliver an electromagnetic interrogation energy to at least one region within a biological subject, the electromagnetic interrogation energy having at least a first peak emission wavelength ranging from about 630 nm to about 660 nm, and a second peak emission wavelength ranging from about 660 nm to about 990 nm.

5. The occlusion monitoring device of claim 1, wherein the interrogation energy emitter component is configured to concurrently or sequentially deliver at least a first interrogation energy and a second interrogation energy, the second interrogation energy different than the first interrogation energy;

wherein the first interrogation energy comprises an electromagnetic interrogation energy, an electrical interrogation energy, an ultrasonic interrogation energy, or a thermal interrogation energy, and the second interrogation energy comprises a different one of an electromagnetic interrogation energy, an electrical interrogation energy, an ultrasonic interrogation energy, or a thermal interrogation energy.

6. The occlusion monitoring device of claim 1, wherein the interrogation energy emitter component is configured to deliver an illumination pattern comprising at least a first region and a second region, the second region having at least one of an illumination intensity, an energy-emitting pattern, a peak emission wavelength, an ON-pulse duration, an OFF-pulse duration, or a pulse frequency different than the first region.

7. The occlusion monitoring device of claim 1, wherein the interrogation energy emitter component is configured to concurrently or sequentially deliver one or more of an electromagnetic interrogation energy, an electrical interrogation energy, an ultrasonic interrogation energy, or a thermal interrogation energy.

8. The occlusion monitoring device of claim 1, wherein the interrogation energy emitter component is configured to deliver electromagnetic interrogation energy to a region with a biological subject.

9. The occlusion monitoring device of claim 1, wherein the interrogation energy emitter component is configured to deliver electrical interrogation energy to a region with a biological subject.

10. The occlusion monitoring device of claim 1, wherein the interrogation energy emitter component is configured to deliver ultrasonic interrogation energy to a region with a biological subject.

11. The occlusion monitoring device of claim 1, wherein the interrogation energy emitter component is configured to deliver thermal interrogation energy to a region with a biological subject.

12. The occlusion monitoring device of claim 1, further comprising:
one or more computer-readable memory media having inflammation marker spectral information configured as a data structure, the data structure including a spectral signature information section having at least one of infection marker spectral information, inflammation marker spectral information, infective stress marker spectral information, or sepsis marker spectral information.

13. The occlusion monitoring device of claim 1, wherein the sensor component is configured to detect at least one of an emitted electromagnetic energy, an emitted electrical energy, an emitted ultrasonic energy, or an emitted thermal energy.

14. The occlusion monitoring device of claim 1, wherein the sensor component is configured to detect at least one of a remitted electromagnetic energy, a remitted electrical energy, a remitted ultrasonic energy, or a remitted thermal energy.

15. The occlusion monitoring device of claim 1, wherein the blood vessel spectral occlusion information includes spectral information cluster according to one or more Fuzzy C-Means Clustering protocols, Graph-Theoretic protocols, Hierarchical Clustering protocols, K-Means Clustering protocols, Locality-Sensitive Hashing protocols, Mixture of Gaussians protocols, Model-Based Clustering protocols, a Cluster-Weighted Modeling protocol, an Expectations-Maximization protocol, a Principal Components Analysis protocol, or Partitional protocols.

16. The occlusion monitoring device of claim 1, wherein the blood vessel spectral occlusion information includes one or more heuristically determined parameters associated with at least one in vivo or in vitro determined metric.

17. The occlusion monitoring device of claim 16, wherein the one or more heuristically determined parameters include at least one of a threshold level or a target parameter.

18. The occlusion monitoring device of claim 16, wherein the one or more heuristically determined parameters include threshold information.

19. The occlusion monitoring device of claim 16, wherein the one or more heuristically determined parameters include at least one of threshold embolus spectral signature information, threshold arterial embolus spectral signature information, threshold thrombus spectral signature information, or threshold deep vein thrombus spectral signature information.

20. The occlusion monitoring device of claim 16, wherein the one or more heuristically determined parameters include at least one of a heuristic protocol determined parameter or a heuristic algorithm determined parameter.

21. The occlusion monitoring device of claim 16, wherein the one or more heuristically determined parameters include at least one occlusion formation model seed parameter.

22. The occlusion monitoring device of claim 16, wherein the one or more heuristically determined parameters include one or more seed parameters for at least one of an occlusion spectral model, a blood spectral model, a fat spectral model, a muscle spectral model, or a bone spectral model.

23. The occlusion monitoring device of claim 1, further comprising:
a controller configured to cluster at least one of a detected emitted energy or detected remitted energy, into two or more information subsets using one or more Fuzzy C-Means Clustering protocols, Graph-Theoretic protocols, Hierarchical Clustering protocols, K-Means Clustering protocols, Locality-Sensitive Hashing protocols, Mixture of Gaussians protocols, Model-Based Clustering protocols, Cluster-Weighted Modeling protocols, Expectations-Maximization protocols, Principal Components Analysis protocols, or Partitional protocols.

24. The occlusion monitoring device of claim 1, wherein the embolus spectral information includes at least one of an embolus absorption value indicative of an embolus absorption coefficient, an embolus extinction value indicative of an embolus extinction coefficient, or an embolus scattering value indicative of an embolus scattering coefficient.

25. The occlusion monitoring device of claim 1, wherein the embolus spectral information includes at least one of embolus absorption coefficient data, embolus extinction coefficient data, or embolus scattering coefficient data.

26. The occlusion monitoring device of claim 1, wherein the arterial embolus spectral information includes at least one of a arterial embolus absorption value indicative of an arterial embolus absorption coefficient, a arterial embolus extinction value indicative of an arterial embolus extinction coefficient, or a arterial embolus scattering value indicative of an arterial embolus scattering coefficient.

27. The occlusion monitoring device of claim 1, wherein arterial embolus spectral information includes at least one of arterial embolus absorption coefficient data, arterial embolus extinction coefficient data, or arterial embolus scattering coefficient data.

28. The occlusion monitoring device of claim 1, wherein the arterial embolus spectral information includes at least one spectral parameter associated with a peripheral artery occlusion.

29. The occlusion monitoring device of claim 1, wherein the thrombus spectral information includes at least one of a thrombus absorption value indicative of a thrombus absorption coefficient, a thrombus extinction value indicative of a thrombus extinction coefficient, or a thrombus scattering value indicative of a thrombus scattering coefficient.

30. The occlusion monitoring device of claim 1, wherein the thrombus spectral information includes at least one of thrombus absorption coefficient data, thrombus extinction coefficient data, or thrombus scattering coefficient data.

31. The occlusion monitoring device of claim 1, wherein the deep vein thrombus spectral information includes at least one of a deep vein thrombus absorption value indicative of a deep vein thrombus absorption coefficient, a deep vein thrombus extinction value indicative of a deep vein thrombus extinction coefficient, or a deep vein thrombus scattering value indicative of a deep vein thrombus scattering coefficient.

32. The occlusion-monitoring system of claim 1, wherein the deep vein thrombus spectral information includes at least one of deep vein thrombus absorption coefficient data, deep vein thrombus extinction coefficient data, or deep vein thrombus scattering coefficient data.

* * * * *